US012799532B2

(12) United States Patent
Lo et al.

(10) Patent No.: US 12,799,532 B2
(45) **Date of Patent: *Nov. 17, 2026**

(54) SEQUENCING ANALYSIS OF CIRCULATING DNA TO DETECT AND MONITOR AUTOIMMUNE DISEASES

(71) Applicant: The Chinese University of Hong Kong, Shatin (HK)

(72) Inventors: Yuk-Ming Dennis Lo, Homantin (CN); Rossa Wai Kwun Chiu, Shatin (CN); Rebecca Wing Yan Chan, Tai Po (CN); Lai Shan Tam, Shatin (CN)

(73) Assignee: The Chinese University of Hong Kong, Shatin (HK)

( * ) Notice: Subject to any disclaimer, the term of this patent is extended or adjusted under 35 U.S.C. 154(b) by 688 days.

This patent is subject to a terminal disclaimer.

(21) Appl. No.: 18/137,732

(22) Filed: Apr. 21, 2023

(65) Prior Publication Data

US 2024/0093298 A1 Mar. 21, 2024

Related U.S. Application Data

(63) Continuation of application No. 16/182,390, filed on Nov. 6, 2018, now abandoned, which is a (Continued)

(51) Int. Cl.

*C12Q 1/68* (2018.01)
*C12Q 1/6883* (2018.01)

(Continued)

(52) U.S. Cl.

CPC ........... *C12Q 1/6883* (2013.01); *G16B 20/00* (2019.02); *G16B 20/20* (2019.02); *G16B 25/00* (2019.02);

(Continued)

(58) Field of Classification Search

None

See application file for complete search history.

(56) References Cited

U.S. PATENT DOCUMENTS

| | | | |
|---|---|---|---|
| 5,700,641 | A | 12/1997 | Salonen |
| 10,174,375 | B2 | 1/2019 | Lo et al. |

(Continued)

FOREIGN PATENT DOCUMENTS

| | | | |
|---|---|---|---|
| CN | 101724691 A | 6/2010 | |
| CN | 102140511 A | 8/2011 | |

(Continued)

OTHER PUBLICATIONS

Galeazzi et al, Dosage and characterization of circulating DNA: present usage and possible applications in systemic autoimmune disorders, Feb. 2003Autoimmunity Reviews 2(1):50-5.*

(Continued)

*Primary Examiner* — Yung-Sheng M Tsui
*Assistant Examiner* — Melody Tsai
(74) *Attorney, Agent, or Firm* — Kilpatrick Townsend & Stockton LLP

(57) ABSTRACT

Systems, methods, and apparatuses are provided for diagnosing auto-immune diseases such as systemic lupus erythematosus (SLE) based on the sizes, methylation levels, and/or genomic characteristics of circulating DNA molecules. Patients provide blood or other tissue samples containing cell-free nucleic molecules for analysis. Massively parallel and/or methylation-aware sequencing can be used to determine the sizes and methylation levels of individual DNA molecules and identify the number of molecules originating from different genomic regions. A level of SLE can be estimated based on: the amount of molecules having sizes below a threshold value; the methylation level(s) of the entire genome or portions of the genome; correlations (Continued)

Size distribution of circulating DNA in plasma of SLE patients (sample size = 20)

between the sizes and methylation levels of DNA molecules; and/or comparing the representation of DNA molecules in each of a plurality of genomic regions with a reference value for that region, and determining an amount of genomic regions having increased or decreased measured genomic representation.

23 Claims, 41 Drawing Sheets

Related U.S. Application Data continuation of application No. 14/491,678, filed on Sep. 19, 2014, now Pat. No. 10,174,375.

(60) Provisional application No. 61/880,604, filed on Sep. 20, 2013.

(51) Int. Cl.

| | |
|---|---|
| ***G16B 20/00*** | (2019.01) |
| ***G16B 20/20*** | (2019.01) |
| ***G16B 25/00*** | (2019.01) |
| ***G16B 25/10*** | (2019.01) |
| ***G16B 30/00*** | (2019.01) |

(52) U.S. Cl.

CPC ............ *G16B 25/10* (2019.02); *G16B 30/00* (2019.02); *C12Q 2600/154* (2013.01)

(56) References Cited

U.S. PATENT DOCUMENTS

| | | | | |
|---|---|---|---|---|
| 2010/0297710 | A1* | 11/2010 | Hoyal-Wrightson | C12N 15/1003 536/25.41 |
| 2012/0178918 | A1* | 7/2012 | Wisniewski | C12N 15/1003 536/25.41 |
| 2013/0224740 | A1* | 8/2013 | Thierry | C12Q 1/686 435/6.12 |
| 2013/0237431 | A1 | 9/2013 | Lo et al. | |

FOREIGN PATENT DOCUMENTS

| | | | |
|---|---|---|---|
| WO | 2012028746 | A1 | 3/2012 |
| WO | 2013060762 | A1 | 5/2013 |
| WO | 2014008426 | A2 | 1/2014 |
| WO | 2014043763 | A1 | 3/2014 |

OTHER PUBLICATIONS

Rumore et al., Endogenous circulating DNA in systemic lupus erythematosus. Occurrence as multimeric complexes bound to histone, J Clin Invest. Jul. 1990;86(1):69-74. doi: 10.1172/JCI114716.*

U.S. Appl. No. 14/491,678, Final Office Action mailed on Apr. 11, 2018, 14 pages.

U.S. Appl. No. 14/491,678, Final Office Action mailed on May 16, 2017, 14 pages.

U.S. Appl. No. 14/491,678, Non-Final Office Action mailed on Jan. 20, 2017, 13 pages.

U.S. Appl. No. 14/491,678, Non-Final Office Action mailed on Nov. 29, 2017, 15 pages.

U.S. Appl. No. 16/182,390, Final Office Action mailed on Oct. 25, 2022, 14 pages.

U.S. Appl. No. 16/182,390, Non-Final Office Action mailed on May 10, 2022, 11 pages.

Anker et al., Spontaneous Extracellular Synthesis of DNA Released by Humanblood Lymphocytes, Cancer Research, vol. 36, Aug. 1976, pp. 2832-2839.

Arbuckle et al., Development of Autoantibodies Before the Clinical Onset of Systemic Lupus Erythematosus, The New England Journal of Medicine, vol. 349, Oct. 16, 2003, pp. 1526-1533.

Balada et al., Associations between the Expression of Epigenetically Regulated Genes and the Expression of DNMTs and MBDs in Systemic Lupus Erythematosus, PLOS One, vol. 7, No. 9, Sep. 21, 2012, 8 pages.

Balada et al., DNA Methylation and Systemic Lupus Erythematosus, Annals of the NY Academy of Sciences, vol. 1108, 2007, pp. 127-136.

Ballestar et al., The Epigenetic Face of Systemic Lupus Erythematosus, Journal of Immunology, vol. 176, 2006, pp. 7143-7147.

Bartoloni et al., Increased Levels of Circulating DNA in Patients With Systemic Autoimmune Diseases: A Possible Marker of Disease Activity in Sjogren's Syndrome, Lupus, vol. 20, May 2011, pp. 928-935.

Beck et al., Next Generation Sequencing of Serum Circulating Nucleic Acids from Patients with Invasive Ductal Breast Cancer Reveals Differences to Healthy and Nonmalignant Controls, Molecular Cancer Research, vol. 8, No. 3, Mar. 2010, pp. 335-342.

Bernknopf et al., A Review of Systemic Lupus Erythematosus and Current Treatment Options, ResearchGate, Formulary, vol. 46, Issue 5, May 2011, pp. 178-194.

Bombardier et al., Derivation of the Sledai. A Disease Activity Index for Lupus Patients, Arthritis and Rheumatism, vol. 35, No. 6, Jun. 1992, pp. 630-640.

Booth et al., Oxidative Bisulfite Sequencing of 5-Methylcytosine and 5-Hydroxyethylcytosine, Nature Protocols, vol. 8, No. 10, Oct. 2013, pp. 1841-1851.

Booth et al., Quantitative Sequencing of 5-Methycytosine and 5-Hydroxymethylcytosine at Single-Base Resolution, Science, vol. 336, Issue 6083, May 18, 2012, pp. 934-937.

Cepika et al., Decrease in Circulating DNA, Il-10 and Baff Levels in Newly-Diagnosed Sle Patients after Corticosteroid and Chloroquine Treatment, Cellular Immunology, Academic Press, vol. 276, No. 1, May 14, 2012, pp. 196-203.

Cervera et al., Morbidity and Mortality in Systemic Lupus Erythematosus During a 10-year Period. A Comparison of Early and Late Manifestations in a Cohort of 1,000 Patients, Medicine, vol. 82, No. 5, Sep. 2003, pp. 299-308.

Chan et al., Cancer Genome Scanning in Plasma: Detection of Tumor-Associated Copy Number Aberrations, Single-Nucleotide Variants, and Tumoral Heterogeneity by Massively Parallel Sequencing, Clinical Chemistry, vol. 59, No. 1, Jan. 2013, pp. 211-224.

Chan et al., Noninvasive Detection of Cancer-Associated Genome-Wide Hypomethylation and Copy Number Aberrations by Plasma DNA Bisulfite Sequencing, Proceedings of the National Academy of Sciences , vol. 110, No. 47, Nov. 19, 2013, pp. 18761-18768.

Chan et al., Plasma DNA Aberrations in Systemic Lupus Erythematosus Revealed by Genomic and Methylomic Sequencing, Proceedings of the National Academy of Sciences, vol. 111, No. 49, Nov. 26, 2014, pp. E5302-E5311.

Chan et al., Size Distributions of Maternal and Fetal DNA in Maternal Plasma, Clinical Chemistry, vol. 50, No. 1, Jan. 2004, pp. 88-92.

Chen et al., Sensitive Detection of Plasma/serum DNA in Patients With Systemic Lupus Erythematosus, Autoimmunity, vol. 40, No. 4, Jun. 2007, pp. 307-310.

Chiu et al., Effects of Blood-Processing Protocols on Fetal and Total DNA Quantification in Maternal Plasma, Clinical Chemistry, vol. 47, No. 9, Sep. 2001, pp. 1607-1613.

Chiu et al., Non-Invasive Prenatal Assessment of Trisomy 21 by Multiplexed Maternal Plasma DNA Sequencing: Large Scale Validity Study, British Medical Journal, vol. 342, Jan. 11, 2011, pp. 1-9.

Chiu et al., Noninvasive Prenatal Diagnosis of Fetal Chromosomal Aneuploidy by Massively Parallel Genomic Sequencing of DNA in Maternal Plasma, Proceedings of the National Academy of Sciences of the United States of America, vol. 105, No. 51, Dec. 23, 2008, pp. 20458-20463.

Cokus et al., Shotgun bisulphite sequencing of the *Arabidopsis* genome reveals DNA methylation patterning, Nature, vol. 452, Mar. 13, 2008, pp. 215-219.

(56) References Cited

OTHER PUBLICATIONS

D'Cruz et al., Systemic Lupus Erythematosus, Lancet, vol. 369, 2007, pp. 587-596.
Duarte et al., Epidemiology of Systemic Lupus Erythematosus, Systemic Lupus Erythematosus, 5th Edition, 2011, pp. 673-696.
Emlen et al., Accelerated in Vitro Apoptosis of Lymphocytes From Patients with Systemic Lupus Erythematosus, Journal of Immunology, vol. 152, Apr. 1994, pp. 3685-3692.
Fan et al., Analysis of the Size Distribution of Fetal and Maternal Cell-Free DNA by Paired-End Sequencing, Molecular Diagnostics and Genetics, Clinical Chemistry, vol. 56, No. 8, Aug. 2010, pp. 1279-1286.
Fan et al., Noninvasive Diagnosis of Fetal Aneuploidy by Shotgun Sequencing DNA from Maternal Blood, Proceedings National Academy of Sciences, vol. 105, No. 42, Oct. 21, 2008, pp. 16266-16271.
Flusberg et al., Direct Detection of DNA Methylation During Single-Molecule, Real-Time Sequencing, Nature Methods, vol. 7, No. 6, Available Online at: htt12s://12ubmed.ncbi.nlm.nih.gov/20453 866/, Jun. 2010, pp. 461-465.
Galeazzi et al., Dosage and Characterization of Circulating DNA: Present Usage and Possible Applications in Systemic Autoimmune Disorders, Autoimmunity Reviews, vol. 2, 2003, pp. 50-55.
Gladman et al., Prognosis, Mortality and Morbidity in Systemic Lupus Erythematosus, Dubois' Lupus Erythematosus, 7th Edition, Lippincott Williams & Wilkins, 2007, pp. 1333-1353.
Hedrich et al., Epigenetic Mechanisms in Systemic Lupus Erythematosus and Other Autoimmune Diseases, Trends in Molecular Medicine, vol. 17, No. 12, Dec. 2011, pp. 714-724.
Homer et al., BFast: an Alignment Tool for Large Scale Genome Resequencing, Public Library of Science One, vol. 4, No. 11, Nov. 11, 2009, pp. 1-10.
Huck et al., Abnormal DNA Methylation and Deoxycytosine-Deoxyguanine Content in Nucleosomes From Lymphocytes Undergoing Apoptosis, Faseb J., vol. 13, 1999, pp. 1415-1422.
Isenberg et al., Detection of Cross-reactive Anti-DNA Antibody Idiotypes in the Serum of Systemic Lupus Erythematosus Patients and of Their Relatives, Arthritis Rheum, vol. 28, No. 9, Sep. 1985, pp. 999-1007.
Isenberg et al., Fifty Years of Anti-ds DNA Antibodies: Are We Approaching Journey's End ?, Rheumatology (Oxford), vol. 46, Jul. 2007, pp. 1052-1056.
Jiang et al., Methy-Pipe: An Integrated Bioinformatics Data Analysis Pipeline for Whole Genome Methylome Analysis, Institute of Electrical and Electronics Engineers International Conference on Bioinformatics and Biomedicine Workshops, Dec. 2010, pp. 585-590.
Jiang et al., Methy-Pipe: An Integrated Bioinformatics Pipeline for Whole Genome Bisulfite Sequencing Data Analysis, Public Library of Science One, vol. 9, No. 6, e100360, Jun. 2014, pp. 1-11.
Kelly et al., Genome-wide Mapping of Nucleosome Positioning and DNA Methylation Within Individual DNA Molecules, Genome Research. vol. 22, Dec. 2012, pp. 2497-2506.
Kotzin , Systemic Lupus Erythematosus, Cell, vol. 85, May 3, 1996, pp. 303-306.
Krzywinski et al., Circos: An Information Aesthetic for Comparative Genomics, Genome Research, vol. 19, No. 9, Sep. 2009, pp. 1639-1645.
Leary et al., Detection of Chromosomal Alterations in the Circulation of Cancer Patients with Whole-Genome Sequencing, Science Translational Medicine, vol. 4, No. 162, Nov. 28, 2012, pp. 1-21.
Lei et al., Abnormal DNA Methylation in CD4+ T Cells From Patients With Systemic Lupus Erythematosus, Systemic Sclerosis, and Dermatomyositis, Scandinavian Journal of Rheumatology, vol. 38, Jun. 2009, pp. 369-374.
Li et al., A Survey of Sequence Alignment Algorithms for Next-Generation Sequencing Briefings in Bioinformatics, Briefings in Bioinformatics, vol. 11, No. 5, May 11, 2010, pp. 473-483.
Li et al., SOAP2: An Improved Ultrafast Tool for Short Read Alignment, Bioinformatics, vol. 25, No. 15, Aug. 1, 2009, pp. 1966-1967.
Lister et al., Human DNA Methylomes at Base Resolution Show Widespread Epigenomic Differences, Nature, vol. 462, No. 7271, Nov. 19, 2009, pp. 315-322.
Lo et al., Maternal Plasma DNA Sequencing Reveals the Genome-Wide Genetic and Mutational Profile of the Fetus, Science Translational Medicine, vol. 2, No. 61, Dec. 8, 2010, pp. 1-13.
Lui et al., Predominant Hematopoietic Origin of Cell-Free DNA in Plasma and Serum After Sex-Mismatched Bone Marrow Transplantation, Clinical Chemistry, vol. 48, No. 3, Mar. 2002, pp. 421-427.
Lun et al., Noninvasive Prenatal Methylomic Analysis by Genomewide Bisulfite Sequencing of Maternal Plasma DNA, Clinical Chemistry, vol. 59, No. 11, Nov. 2013, pp. 1583-1594.
Morimoto et al., Correlation Between Clinical Activity of Systemic Lupus Erythematosus and the Amounts of DNA in DNA /Anti-DNA Antibody Immune Complexes, Journal of Immunology, vol. 129, No. 5, Nov. 1982, pp. 1960-1965.
Munoz et al., SLE—A Disease of Clearance Deficiency, Rheumatology (Oxford), vol. 44, Sep. 2005, pp. 1101-1107.
Palomaki et al., DNA Sequencing of Maternal Plasma to Detect Down Syndrome: An International Clinical Validation Study, Genetics in Medicine, vol. 13, No. 11, Nov. 2011, pp. 913-920.
Papalian et al., Reaction of Systemic Lupus Erythematosus Antinative DNA Antibodies With Native DNA Fragments From 20 to 1,200 Base Pairs, Journal of Clinical Investigation, vol. 65, Feb. 1980, pp. 469-477.
International Application No. PCT/IB2014/064682, International Search Report and Written Opinion mailed on Feb. 4, 2015, 9 pages.
Pisetsky et al., The Blood Nucleome in the Pathogenesis of SLE, Autoimmunity Reviews, vol. 10, No. 1, Nov. 2010, pp. 35-37.
Pisetsky et al., The Generation of Extracellular DNA in SLE: The Role of Death and Sex, Scandinavian Journal of Immunology, vol. 64, Sep. 2006, pp. 200-204.
Pisetsky, The immune response to cell death in SLE, Autoimmunity Reviews, vol. 3, Nov. 2004, pp. 500-504.
Pons-Estel et al., Understanding the Epidemiology and Progression of Systemic Lupus Erythematosus., Semin Arthritis Rheum, vol. 39, No. 4, Feb. 2010, pp. 257-268.
Raptis et al., Quantitation and Characterization of Plasma DNA in Normals and Patients with Systemic Lupus Erythematosus, Journal of Clinical Investigation, vol. 66, No. 6, Dec. 1980, pp. 1391-1399.
Richardson et al., Evidence for Impaired T-Cell DNA Methylation in Systemic Lupus Erythematosus and Rheumatoid Arthritis, Arthritis Rheum, vol. 33, No. 11, Nov. 1990, pp. 1665-1673.
Rogers et al., Excretion of Deoxyribonucleic Acid by Lymphocytes Stimulated With Phytohemagglutinin or Antigen, Proceedings of the National Academy of Sciences of the United States of America, vol. 69, No. 7, Jul. 1972, pp. 1685-1689.
Rullo et al., Recent Insights Into the Genetic Basis of Systemic Lupus Erythematosus, Annals of the Rheumatic Diseases, vol. 72, No. 2, Apr. 2013, pp. 56-61.
Rumore, Endogenous circulating DNA in systemic lupus erythematosus. Occurrence as multimeric complexes bound to histone., The Journal of Clinical Investigation, vol. 86, Issue No. 1, Jul. 1990, pp. 69-74.
Sallai et al., Antinucleosome Antibodies and Decreased Deoxyribonuclease Activity in Sera of Patients With Systemic Lupus Erythematosus, Clinical and Diagnostic Laboratory Immunology, vol. 12, No. 1, Jan. 2005, pp. 56-59.
Schwarzenbach et al., Cell-Free Nucleic Acids as Biomarkers in Cancer Patients, Nature Reviews Cancer, vol. 11, No. 6, Jun. 2011, pp. 426-437.
Sekigawa et al., DNA Methylation: Its contribution to Systemic Lupus Erythematosus, Clinical and Experimental Medicine, vol. 6, No. 3, Oct. 2006, pp. 99-106.
Shim et al., Detection and Quantification of Methylation in DNA using Solid-State Nanopores, Scientific Reports, vol. 3, No. 1389, Mar. 11, 2013, pp. 1-8.
Shoshan et al., Accelerated Fas-mediated Apoptosis of Monocytes and Maturing Macrophages From Patients With Systemic Lupus Erythematosus: Relevance to in Vitro Impairment of Interaction With iC3b-opsonized Apoptotic Cells, Journal of Immunology, vol. 167, 2001, pp. 5963-5969.

(56) References Cited

OTHER PUBLICATIONS

Strickland et al., Epigenetics in Human Autoimmunity. Epigenetics in Autoimmunity—DNA Methylation in Systemic Lupus Erythematosus and Beyond, Autoimmunity, vol. 41, No. 4, May 2008, pp. 278-286.
Su et al., The Role of Extracellular DNA in Autoimmunity in SLE, Scandinavian Journal of Immunology, vol. 70, Sep. 2009, pp. 175-183.
Tan et al., Characteristics of a Soluble Nuclear Antigen Precipitating With Sera of Patients With Systemic Lupus Erythematosus, Journal of Immunology, vol. 96, Mar. 1966, pp. 464-471.
Tax et al., Apoptosis, Nucleosomes, and Nephritis in Systemic Lupus Erythematosus, Kidney International, vol. 48, 1995, pp. 666-673.
Termaat et al., Anti-DNA Antibodies Can Bind to the Glomerulus via Two Distinct Mechanisms, Kidney international, vol. 42, Issue 6, Dec. 1992, pp. 1363-1371.
Tsokos, Systemic Lupus Erythematosus, The New England Journal of Medicine, vol. 365, No. 22, Dec. 2011, pp. 2110-2121.
Tsui et al., High Resolution Size Analysis of Fetal DNA in the Urine of Pregnant Women by Paired-End Massively Parallel Sequencing, Public Library of Science One, vol. 7, No. 10, Oct. 2012, pp. 1-7.
Tsui et al., Systematic Micro-Array Based Identification of Placental mRNA in Maternal Plasma: Towards Non-Invasive Prenatal Gene Expression Profiling, Journal of Medical Genetics, vol. 41, Jun. 2004, pp. 461-467.
Uccellini et al., Autoreactive B Cells Discriminate CpG-rich and CpG-Poor DNA and This Response Is Modulated by IFN-alpha, Journal of Immunology, vol. 181, Nov. 2008, pp. 5875-5884.
Uccellini et al., Selective Binding of Anti-DNA Antibodies to Native dsDNA Fragments of Differing Sequence, Immunology Letters, vol. 143, Mar. 2012, pp. 85-91.
Valle et al., DNase 1 and Systemic Lupus Erythematosus, Autoimmun Rev., vol. 7, May 2008, pp. 359-363.
Wen et al., DNA Hypomethylation Is Crucial for Apoptotic DNA to Induce Systemic Lupus Erythematosus-like Autoimmune Disease in SLE-Non-Susceptible Mice, Rheumatology, vol. 46, Dec. 2007, pp. 1796-1803.
Winfield et al., Avidity of Anti-DNA Antibodies in Serum and IgG Glomerular Eluates from Patients with Systemic Lupus Erythematosus. Association of High Avidity Anti-Native DNA Antibody with Glomerulonephritis, Journal of Clinical Investigation, vol. 59, Jan. 1977, pp. 90-96.
Yang et al., Lupus Autoimmunity Altered by Cellular Methylation Metabolism, Autoimmunity, vol. 46, No. 1, Feb. 2013, pp. 21-31.
Yee et al., The Use of Systemic Lupus Erythematosus Disease Activity Lndex-2000 to Define Active Disease and Minimal Clinically Meaningful Change Based on Data From a Large Cohort of Systemic Lupus Erythematosus Patients, Rheumatology, vol. 50, Jan. 18, 2011, pp. 982-988.
Yu et al., Size-Based Molecular Diagnostics Using Plasma DNA for Noninvasive Prenatal Testing, Proceedings of the National Academy of Sciences, vol. 111, No. 23, Jun. 10, 2014, pp. 8583-8588.
Yu et al., Tet-Assisted Bisulfite Sequencing of 5-Hydroxymethylcytosine, Nature Protocols, vol. 7, No. 12, Dec. 2012, pp. 2159-2170.
Zhang et al., Impaired DNA Methylation and Its Mechanisms in CD4(+)t Cells of Systemic Lupus Erythematosus, Journal of Autoimmunity, vol. 41, Mar. 2013, pp. 92-99.
Zheng et al., Nonhematopoietically Derived DNA is Shorter than Hematopoietically Derived DNA in Plasma: A Transplantation Model, Clinical Chemistry, vol. 58, No. 3, Mar. 2012, pp. 549-558.

* cited by examiner

Relationship between proportion of bins with hypomethylation and SLE disease activity score (SLEDAI)

Genome-wide methylation profile of the plasma and buffy coat of two representative active SLE cases Methylation densities of circulating DNA at various sizes SLE Group III: Moderate / high activity Sample: TBR36
Tumor DNA fraction: 40%

From inside to outside:
1) CNA z-score
2) Methylation z-score

Sample: TBR36
Tumor DNA fraction: 40%

Sample: TBR34
Tumor DNA fraction: 30%
From inside to outside:
1) CNA z-score
2) Methylation z-score Sample: TBR34
Tumor DNA fraction: 30%

SEQUENCING ANALYSIS OF CIRCULATING DNA TO DETECT AND MONITOR AUTOIMMUNE DISEASES

CROSS-REFERENCES TO RELATED APPLICATIONS

This application is a continuation application of U.S. patent application Ser. No. 16/182,390, entitled "SEQUENCING ANALYSIS OF CIRCULATING DNA TO DETECT AND MONITOR AUTOIMMUNE DISEASES" and filed on Nov. 6, 2018, which is a continuation application of U.S. patent application Ser. No. 14/491,678, entitled "SEQUENCING ANALYSIS OF CIRCULATING DNA TO DETECT AND MONITOR AUTOIMMUNE DISEASES" and filed on Sep. 19, 2014, now U.S. Pat. No. 10,174,375, which claims the benefit of U.S. Provisional Application No. 61/880,604, entitled "SEQUENCING ANALYSIS OF CIRCULATING DNA TO DETECT AND MONITOR AUTOIMMUNE DISEASES" and filed Sep. 20, 2013, the entire contents of which are incorporated herein by reference. This application is related to International Patent Application No. PCT/AU2013/001088, entitled "NON-INVASIVE DETERMINATION OF METHYLOME OF FETUS OR TUMOR FROM PLASMA" and filed Sep. 20, 2013, as well as to U.S. patent application Ser. No. 13/842,209, entitled "NON-INVASIVE DETERMINATION OF METHYLOME OF FETUS OR TUMOR FROM PLASMA" and filed Mar. 15, 2013, now U.S. Pat. No. 9,732,390, the entire contents of which are incorporated herein by reference.

BACKGROUND

Systemic lupus erythematosus (SLE) is an autoimmune disease which is caused by the 'self-attack' by the immune system against the body and results in inflammation and tissue damage[1]. It has a strong predilection in women with a female to male ratio of around 9:1 and peak onset during child-bearing years 2. It can manifest in a chronic manner or be of a form that has recurrent relapses. Unlike other autoimmune diseases such as multiple sclerosis and type 1 diabetes mellitus, SLE is considered to be a prototypic systemic autoimmune disease[3,4]. It has the potential of affecting multiple organ systems including the skin, muscles, bones, lungs, kidneys, cardiovascular and central nervous systems. Renal complications, infections, myocardial infarction and central nervous system involvement are the major causes of morbidity and even death in SLE patients[5]. The 10-year survival rate is about 70%[6]. The extremely diverse and variable clinical manifestations present a challenge on the SLE management to clinicians.

SLE is characterized by the loss of immunologic self-tolerance and production of autoantibodies. Serum anti-double-stranded (ds) DNA antibody titer of SLE patients is used as a serologic means to assess the disease activity. However, about 30% SLE patients are negative for this test even during the active stage. On the other hand, positive anti-ds DNA antibody has been reported in patients with other diseases, such as rheumatoid arthritis and certain dermatologic disorders[7,8].

The etiology of SLE remains enigmatic[9]; however cell death has been regarded as an important event in the pathogenesis of SLE as it leads to the release of antigens, such as nucleic acids, for immune complex formation which may trigger a cascade of immune responses against the body of the SLE patients[10-14]. In fact, defects in the mechanism of cell death including accelerated apoptosis of lymphocytes and macrophages[15,16], impairment in the clearance of dead cells[17] and deficiency in DNase activity[18,19] have been implicated in SLE and suggested to result in the generation of extra-cellular auto-antigens[11-14].

SLE was one of the pathological conditions reported to be associated with the presence of circulating DNA[20]. Since then, studies using various methods have consistently demonstrated elevations of circulating DNA in SLE patients[21-23]. In addition, some early reports have highlighted that the circulating DNA that form immune complexes with auto-antibodies in SLE patients display a characteristic fragmentation pattern which resembles the DNA laddering pattern of apoptosis by gel electrophoresis[24-26]. These findings have implicated the association between the pathogenesis of SLE, apoptosis and circulating nucleic acids. However, further studies on the biological and pathophysiological characteristics of circulating nucleic acids in SLE were few.

BRIEF SUMMARY

Embodiments provide systems, methods, and apparatuses for diagnosing SLE based on the sizes and/or methylation levels and/or genomic representations and/or genomic characteristics of circulating DNA molecules. Examples are provided. In some embodiments, massively parallel sequencing or an alternative method is used to determine the sizes of DNA molecules, which can be compared with a threshhold value. Compared with a healthy patient, an SLE patient presents a higher percentage of DNA molecules with sizes less than the threshold value, or a higher ratio of shorter DNA molecules to longer DNA molecules. In other embodiments, bisulfite sequencing data are used to obtain the methylation density of the entire genome or portions thereof. Portions can include all repeat and/or non-repeat regions, or regions of equal size or different size for the regions. Decreased methylation (hypomethylation) in the genome, as detected in circulating DNA, correlates with the occurrence of SLE in patients or the exacerbation of disease activity.

In one embodiment, one can include additional steps that can distinguish 5-methylcytosine from 5-hydroxymethylcytosine. One such approach is oxidative bisulfite sequencing (oxBS-seq), which can elucidate the location of 5-methylcytosine and 5-hydroxymethylcytosine at single-base resolution[27,28]. In bisulfite sequencing, both 5-methylcytosine from 5-hydroxymethylcytosine are read as cytosines and thus cannot be discriminated. On the other hand, in oxB S-seq, specific oxidation of 5-hydroxymethylcytosine to 5-formylcytosine by treatment with potassium perruthenate (KRuO4), followed by the conversion of the newly formed 5-formylcytosine to uracil using bisulfite conversion can allow 5-hydroxymethylcytosine to be distinguished from 5-methylcytosine. Hence, a readout of 5-methylcytosine is obtained from a single oxBS-seq run, and 5-hydroxymethylcytosine levels are deduced by comparison with the bisulfite sequencing results. In another embodiment, 5-methylcytosine can be distinguished from 5-hydroxymethylcytosine using Tet-assisted bisulfite sequencing (TAB-seq)[29]. TAB-seq can identify 5-hydroxymethylcytosine at single-base resolution, as well as determine its abundance at each modification site. This method involves β-glucosyltransferase-mediated protection of 5-hydroxymethylcytosine (glucosylation) and recombinant mouse Tet1(mTet1)-mediated oxidation of 5-methylcytosine to 5-carboxylcytosine. After the subsequent bisulfite treatment and PCR amplification, both cytosine and 5-carboxylcytosine (derived from 5-methylcytosine) are converted to thymine (T), whereas 5-hydroxymethylcytosine will be read as C. In yet other embodiments, selected single molecule sequencing platforms allow the methylation status of DNA molecules to be elucidated directly without bisulfite conversion[30,31]. The use of such platforms allows the non-bisulfite converted plasma DNA to be used to determine the methylation levels of plasma DNA or to determine the plasma methylome. Such platforms can detect N6-methyladenine, 5-methylcytosine and 5-hydroxymethylcytosine.

In still other embodiments, the sizes and methylation levels of DNA molecules in a biological sample are both determined, and SLE is diagnosed when DNA molcules falling within a certain size range exhibit reduced methylation. In yet other embodiments, the genomic representation and/or other genomic characteristics are determined, either alone or in combination with the sizes and/or methylation levels of DNA molecules in the biological sample.

Accordingly, embodiments show that circulating nucleic acids of the SLE patients can exhibit characteristic molecular signatures. The dysregulation of apoptosis and production of autoantibodies against nucleic acids can lead to altered biological characteristics and clearance mechanisms of circulating nucleic acids. Furthermore, inflammation and apoptosis of cells from different organ systems can result in distinguishable characteristic profiles of circulating nucleic acids that can reveal the involvements and extents of damage of different organs in SLE patients.

The discussion below shows a delineation of the genome-wide characteristics of circulating nucleic acids in the plasma of SLE patients at an unprecedented high level of resolution with the use of massively parallel sequencing technology and hence develop new diagnostic and monitoring tools for SLE. In addition to plasma, serum can also be used in a similar fashion. The sequencing or other type of analyses can be performed using a range of methylation-aware platforms, including but not limited to massively parallel sequencing, single molecular sequencing, microarray (e.g. oligonucleotide arrays), or mass spectrometry (such as the Epityper, Sequenom, Inc., analysis). In some embodiments, such analyses may be preceded by procedures that are sensitive to the methylation status of DNA molecules, including, but not limited to, cytosine immunoprecipitation and methylation-aware restriction enzyme digestion.

Other embodiments are directed to systems and computer readable media associated with methods described herein.

A better understanding of the nature and advantages of embodiments of the present invention may be gained with reference to the following detailed description and the accompanying drawings.

DEFINITIONS

Figure 1:
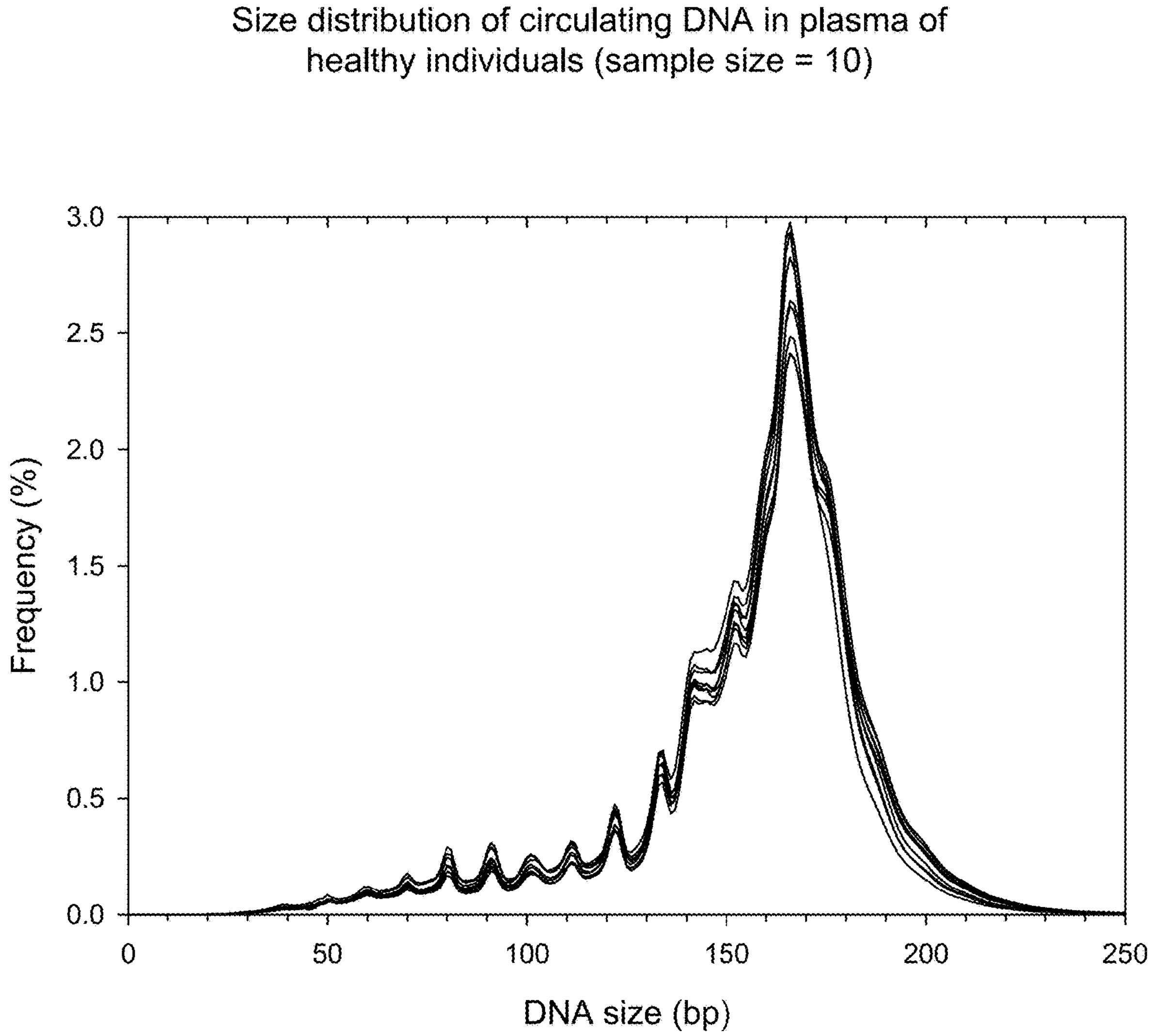
FIG. 1 shows the size profiles of circulating DNA molecules in the plasma of 10 healthy individuals.

A "site" corresponds to a single site, which may be a single base position or a group of correlated base positions, e.g., a CpG site. A "locus" may correspond to a region that includes multiple sites. A locus can include just one site, which would make the locus equivalent to a site in that context.

The "methylation index" for each genomic site (e.g., a CpG site) refers to the proportion of sequence reads showing methylation at the site over the total number of reads covering that site. The "methylation density" of a region is the number of reads at sites within the region showing methylation divided by the total number of reads covering the sites in the region. The sites may have specific characteristics, e.g., being CpG sites. Thus, the "CpG methylation density" of a region is the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" refers the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels."

A "methylation profile" (also called methylation status) includes information related to DNA methylation for a region. Information related to DNA methylation can include, but is not limited to, a methylation index of a CpG site, a methylation density of CpG sites in a region, a distribution of CpG sites over a contiguous region, a pattern or level of methylation for each individual CpG site within a region that contains more than one CpG site, and non-CpG methylation. The latter can involve the methylation of cytosine that precede a base other than G, including A, C or T. A methylation profile of a substantial part of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as N6-methyladenine, has also been reported.

A "tissue" corresponds to any cells. Different types of tissue may correspond to different types of cells (e.g., liver, lung, or blood), but also may correspond to tissue from different organisms (mother versus fetus) or to healthy cells versus tumor cells. A "biological sample" refers to any sample that is taken from a subject (e.g., a human, such as a person with SLE, or a person suspected of having SLE, an organ transplant recipient or a subject suspected of having a disease process involving an organ (e.g. the heart in myocardial infarction, or the brain in stroke)) and contains one or more nucleic acid molecule(s) of interest. The biological sample can be a bodily fluid, such as blood, plasma, serum, urine, vaginal fluid, uterine or vaginal flushing fluids, pleural fluid, ascitic fluid, cerebrospinal fluid, saliva, sweat, tears, sputum, bronchoalveolar lavage fluid, etc. Stool samples can also be used.

The term "level of SLE" can refer to whether a patient (or organism) has SLE, the extent of symptoms presented by the patient, or the progress of SLE in particular organs of the patient or overall. The level of SLE can be quantitative (i.e., be represented by a number or fall on a numerical scale) or qualitative. The level of SLE can correlate with or be represented by established metrics of the disease, for example the Systemic Lupus Erythematosus Disease Activity Index (SLEDAI) or the anti-DNA antibody titer in a particular tissue. SLEDAI is an example of a score. The level of SLE can also correspond to the groups into which patients are sorted or triaged, as discussed below (i.e., quiescent, mild activity, and moderate/high activity).

"Methylation-aware sequencing" refers to sequencing that identifies whether one or more sites of a nucleic acid molecule are methylated. One embodiment of methylation-aware sequencing includes treating DNA with sodium bisulfite and then performing DNA sequencing. In other embodiments, methylation-aware sequencing can be performed without using sodium bisulfite, but rather using a single molecule sequencing platform that allows the methylation status of DNA molecules (including N6-methyladenine, 5-methylcytosine and 5-hydroxymethylcytosine) to be elucidated directly without bisulfite conversion[30,31]; or through the immunoprecipitation of methylated cytosine (e.g. by using an antibody against methylcytosine or by using a methylated DNA binding protein) followed by sequencing; or through the use of methylation-sensitive restriction enzymes followed by sequencing. In still another embodiment, non-sequencing techniques are used, such as arrays, digital PCR and mass spectrometry.

DETAILED DESCRIPTION

It has now been discovered that SLE and other autoimmune diseases can be diagnosed by analyzing patient samples containing cell-free nucleic acid molecules. The samples can be of blood or plasma and contain circulating DNA fragments. In some embodiments, the level of an auto-immune disease is estimated by examining the distribution of sizes of nucleic acid molecules in the sample. Samples with higher abundances of short molecules, as indicated by the portion of molecules having sizes within a range or below a threshold value, can indicate a higher level of the disease. In other embodiments, the level of a disease is estimated by determining methylation levels of the nucleic acid molecules. This can be done using methylation-aware sequencing, and if desired the sequence of each nucleic acid molecule can be aligned with a reference genome sequence. Reduced methylation (i.e., hypomethylation) in select regions or portions of the genome, or in the genome as a whole, as manifested by nucleic acid molecules of the sample, can indicate a higher level of the auto-immune disease. Methylation levels can be determined for, e.g., individual sites in the genome, individual chromosomes or portions thereof, repeat or non-repeat regions, coding or non-coding regions, or non-overlapping and/or contiguous bins. In addition, in some embodiments the level of the disease is estimated based on correlations between the sizes and methylation levels of nucleic acid molecules in the sample. Reduced or aberrant methylation of nucleic acid molecules having a particular size or range of sizes, as compared with a threshold methylation level or with the methylation levels of molecules having different sizes, can indicate a higher level of the auto-immune disease. In still other embodiments, the level of an auto-immune disease is estimated based on the measured genomic representations of nucleic acid molecules in a plurality of genomic regions. The number of molecules localizing or aligning to each genomic region, or another measure of the representation of molecules in the region, is compared with a reference value to determine whether the genomic region exhibits increased or decreased (e.g., aberrant) genomic representation. The level of the auto-immune disease is then estimated by comparing the amount (e.g., number) of genomic regions exhibiting increased or decreased genomic representation with a threshold amount (e.g., threshold number). Methods, systems, and apparatus are provided for analyzing biological samples and diagnosing auto-immune diseases.

I. RELATIONSHIP BETWEEN SIZE OF CIRCULATING DNA AND SLE

The acceleration of cell death and impairment of clearance of the by-products of the dead cells associated with SLE may generate extra-cellular DNA and change the characteristics of DNA in the circulation of SLE patients. In addition, other mechanisms involved in the pathogenesis of SLE, such as the deficiency of DNase activity and overproduction of autoantibodies against DNA, can also alter the integrity of circulating DNA. It follows that the immune dysregulation of SLE can change the size of circulating DNA in the plasma of SLE patients. However, due to the paucity of studies in this area, one could not predict if plasma DNA is subjected to more or less enzymatic degradation or whether the anti-ds DNA antibodies would impair the clearance of the long or short plasma DNA molecules. The relative contributions of these phenomena, if in existence, are not known either. Based on these unpredictable factors, one could not estimate if there would be more or less of the shorter or longer DNA molecules in plasma of SLE patients when compared with healthy individuals.

A. Results

Figure 2:
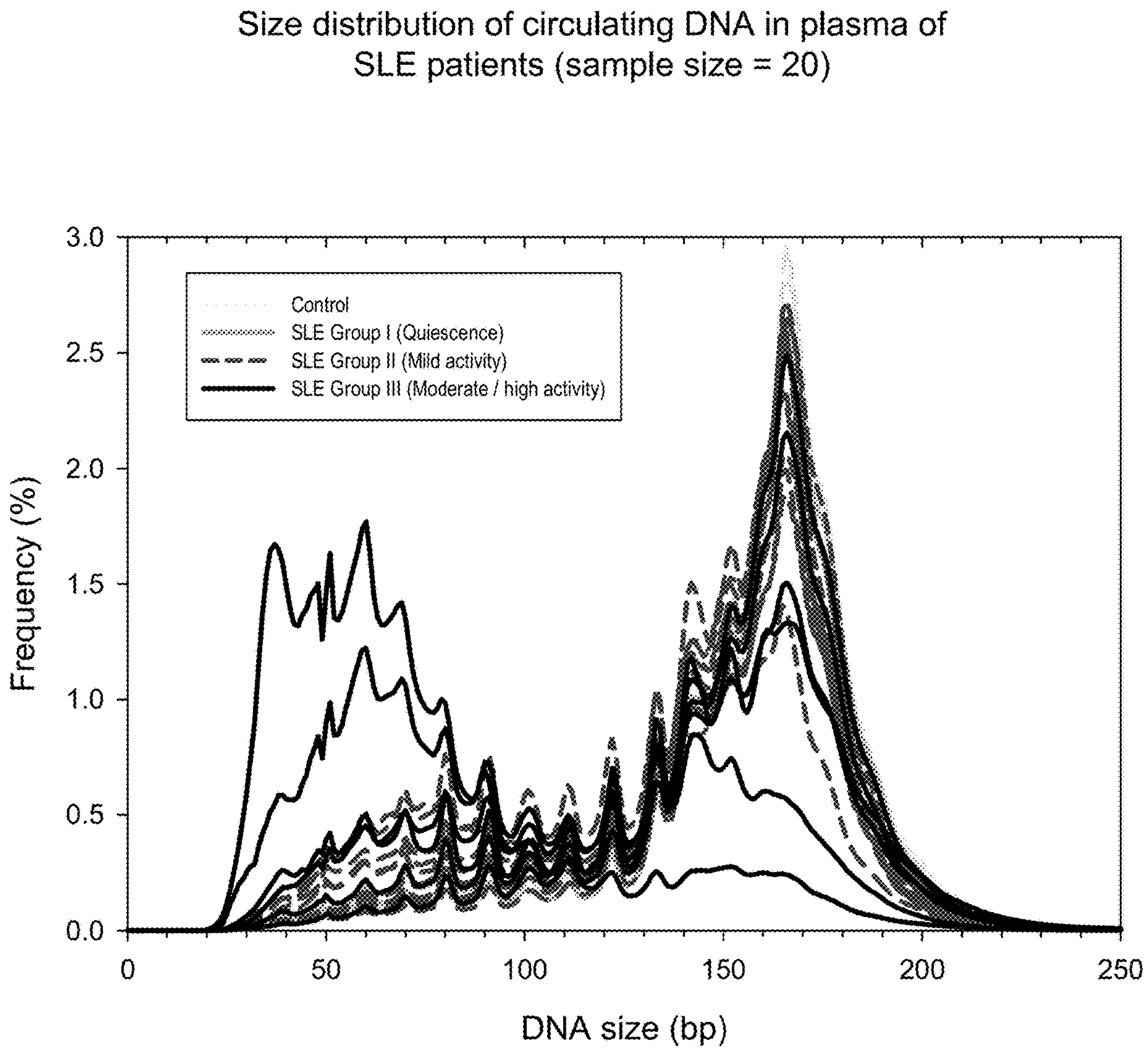
FIG. 2 shows the size profiles of circulating DNA molecules in the plasma of 20 SLE patients.
Figure 3:
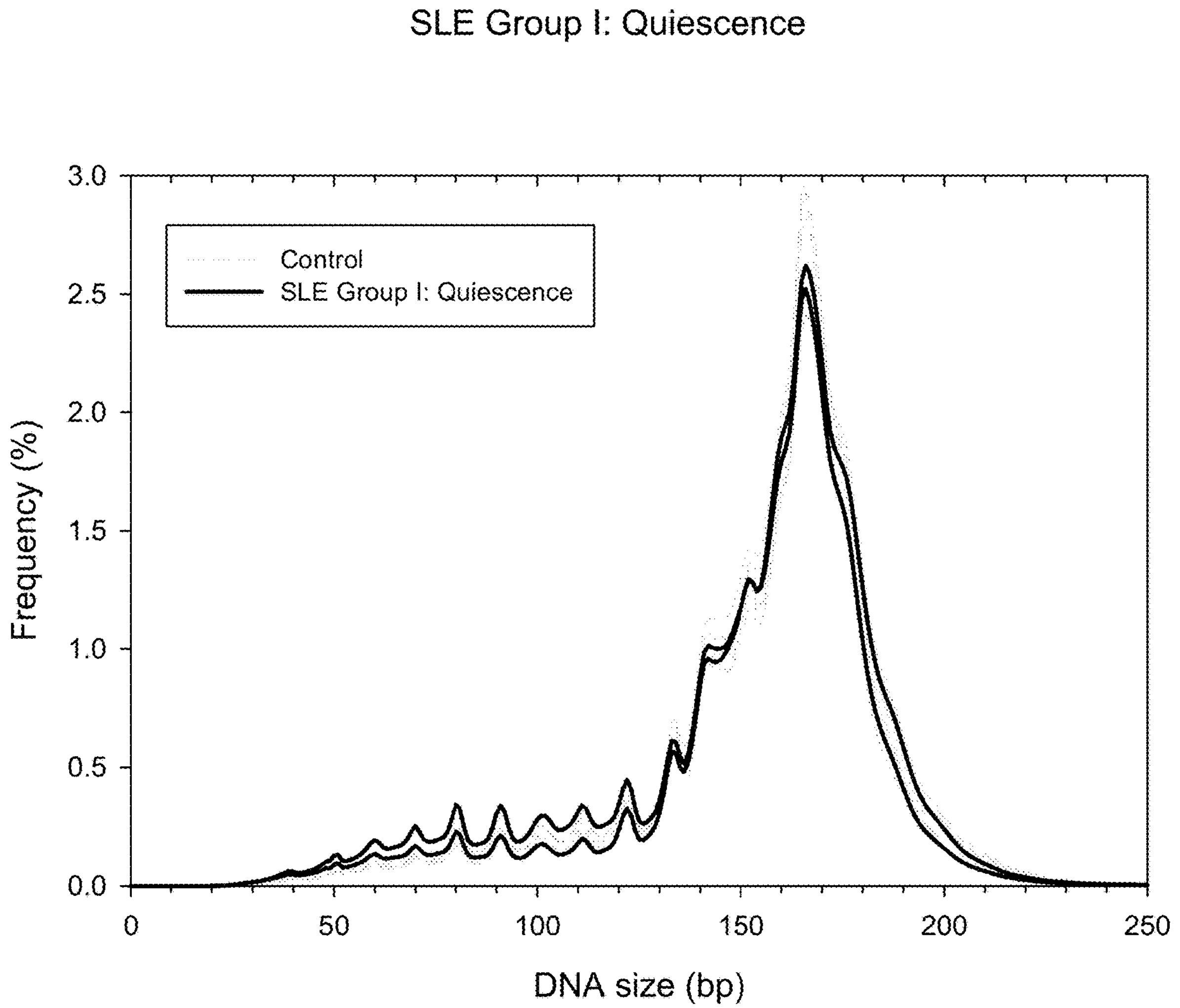
FIG. 3 shows the size profiles of circulating DNA molecules in the plasma of group I (quiescent) SLE patients, who have Systemic Lupus Erythematosus Disease Activity Index (SLEDAI) less than 4.
Figure 4:
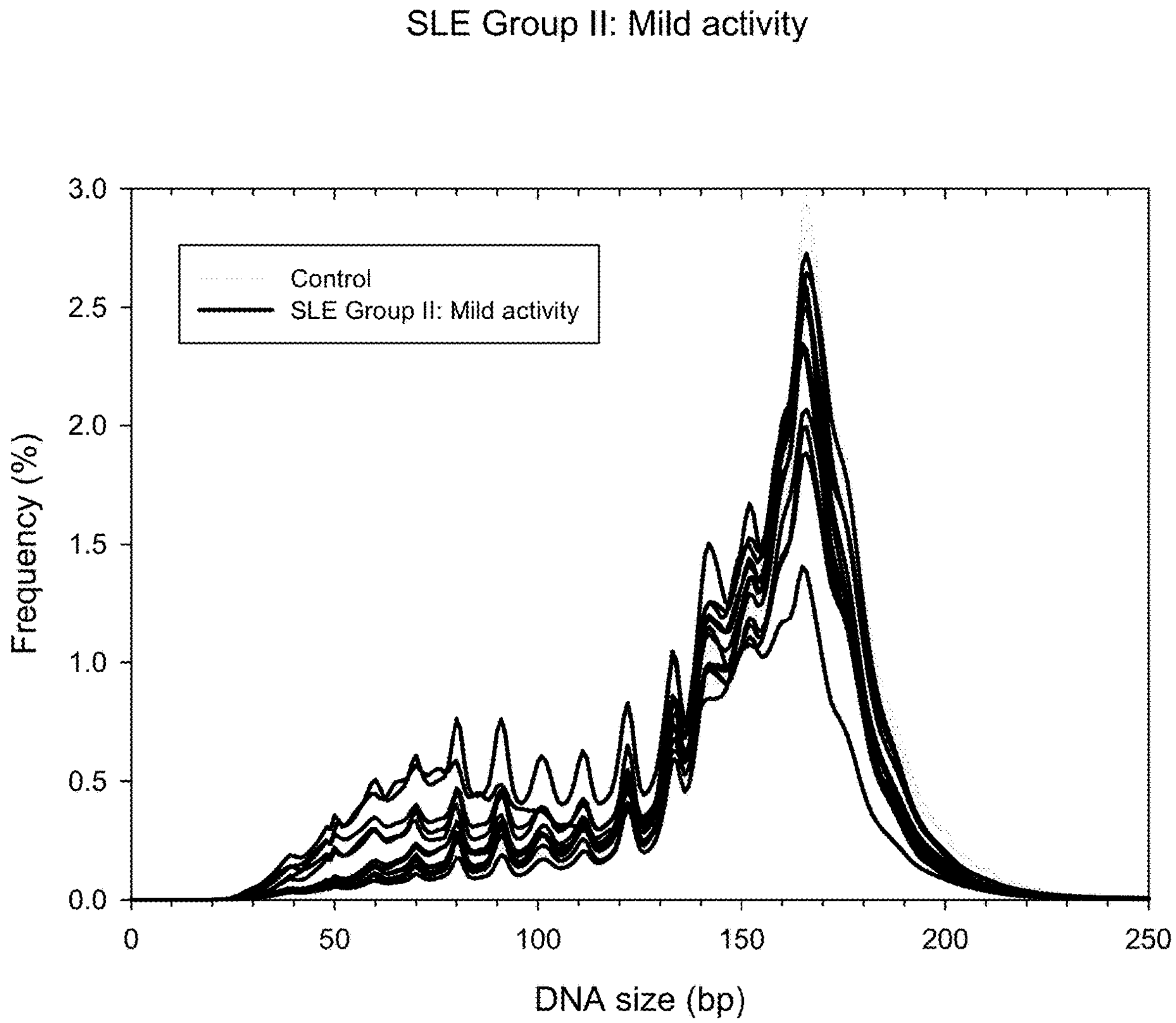
FIG. 4 shows the size profiles of circulating DNA molecules in the plasma of group II SLE patients, who have mild disease activity and SLEDAI between 4 and 6.
Figure 5:
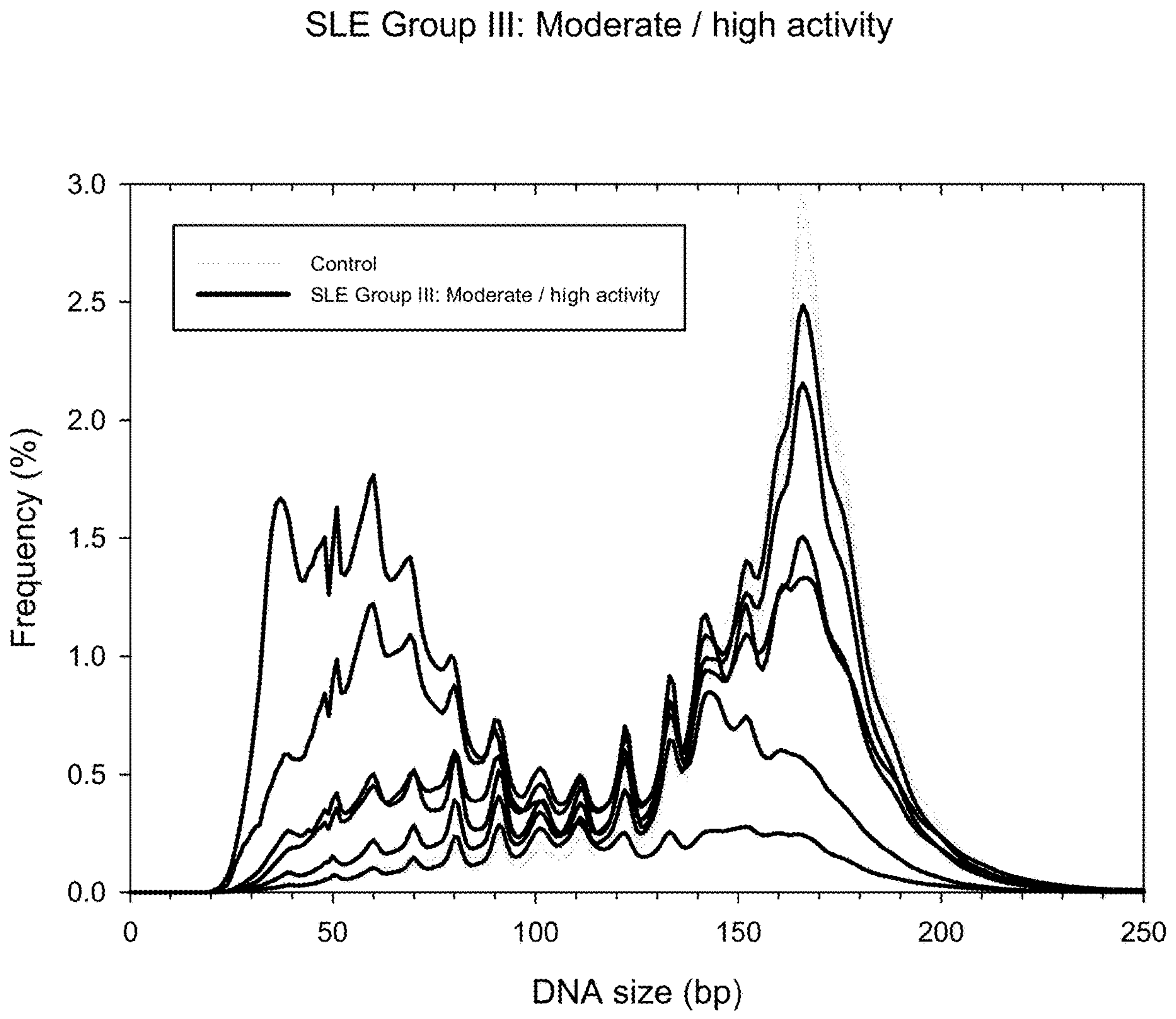
FIG. 5 shows the size profiles of circulating DNA molecules in the plasma of group III SLE patients, who have moderate or high disease activity and SLEDAI over 6.

We used massively parallel paired-end DNA sequencing analysis to determine the molecular size distribution of circulating DNA in the plasma of 10 healthy individuals and 20 SLE patients with disease activities ranging from inactive to active. As shown in FIG. 1, the size profile of each of the healthy individuals showed a major peak at 166 base pairs (bp) and with smaller peaks occurring at a 10-bp periodicity from approximately 143 bp and smaller. However, the size profiles of the SLE patients were altered as illustrated in FIG. 2. We categorized the SLE patients into 3 groups (I, II and III) according to their disease activities and compared the size profiles between the groups. SLE patients with a higher disease activity can have more short DNA. Group I included the quiescent patients with SLEDAI less than 4. Their size profiles were similar to those of the healthy individuals (FIG. 3). Group II included the patients with mild disease activity and SLEDAI between 4 and 6. Their size profiles showed that the 166-bp peaks appeared to be shorter while other peaks (<=143 bp) were higher (FIG. 4). Group III included the patients with moderate or high disease activity and SLEDAI over 6. As shown in FIG. 5, their size profiles exhibited the most aberrant size distribution with the greatest extent of reduction of the 166-bp peak but elevation of other peaks. This indicated that circulating DNA in plasma of SLE patients appeared to be more fragmented and had a lower integrity when compared with healthy individuals.

Figure 6A:
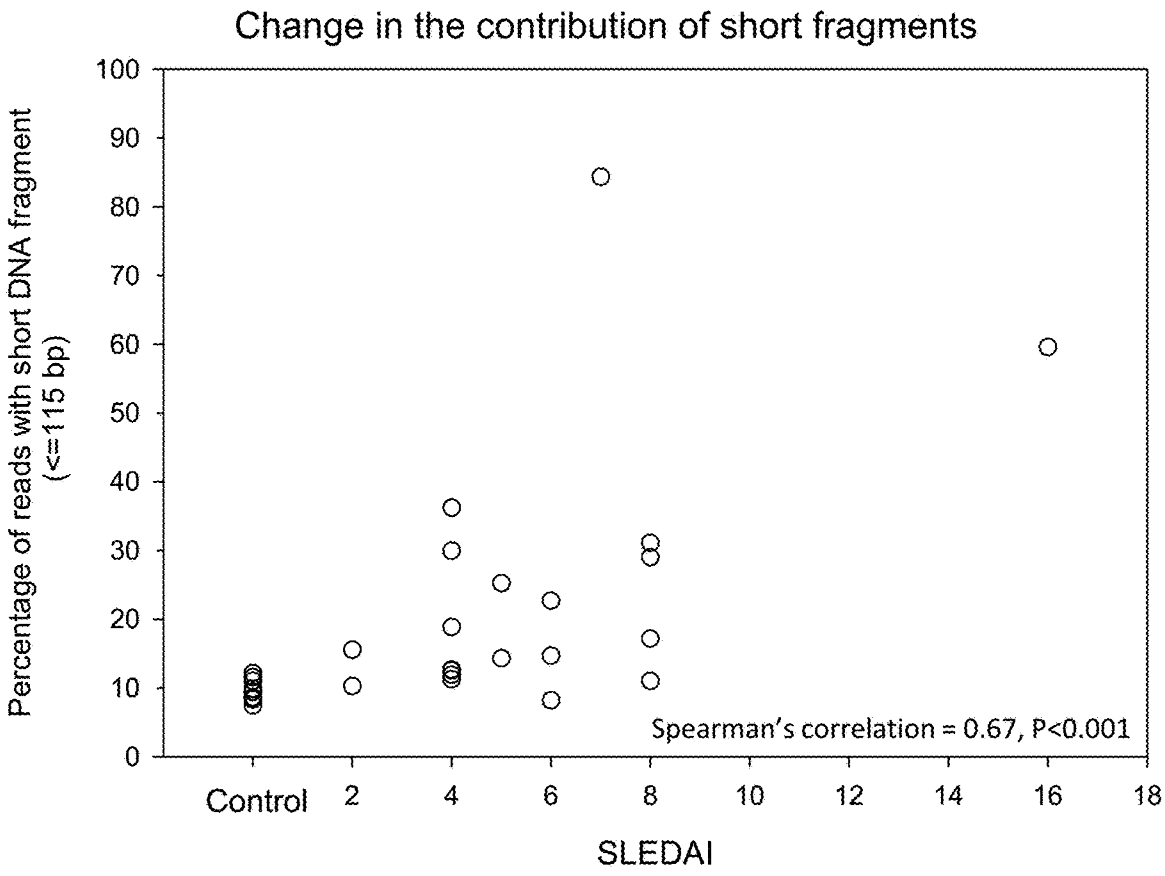
FIGS. 6A-B show a correlation between the percentage of DNA molecules having sizes less than or equal to 115 bp in the plasma of a patient, and the level of SLE disease activity as reflected by SLEDAI in the patient for a group of SLE patients.
Figure 6B:
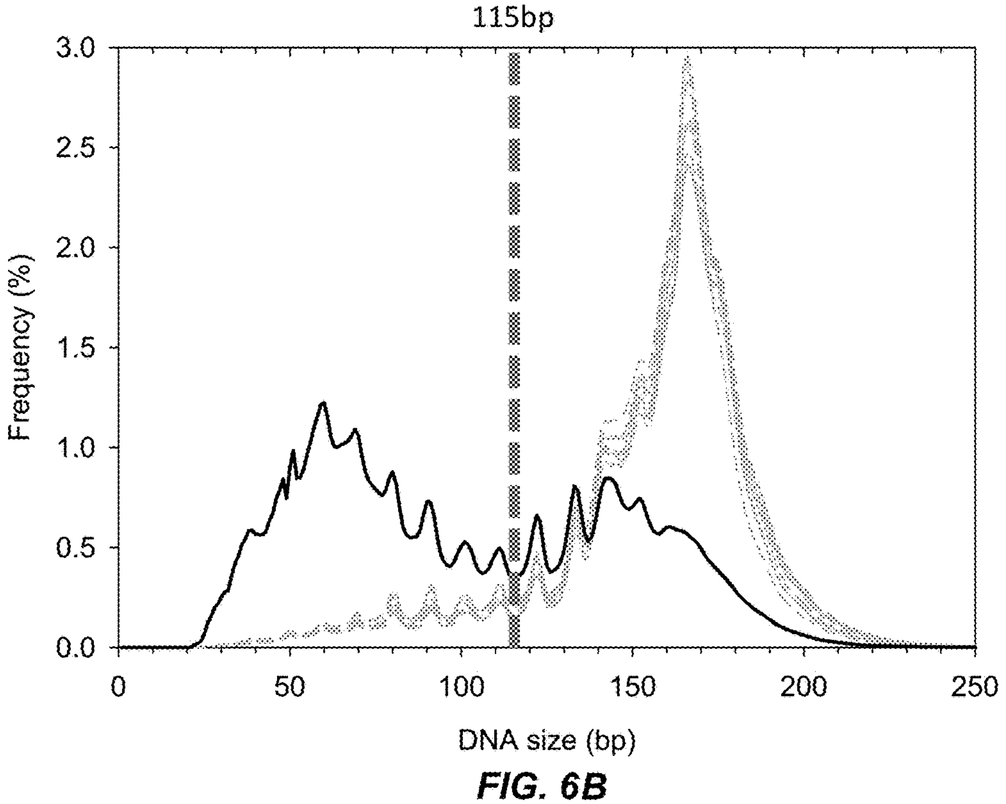
Figure 7A:
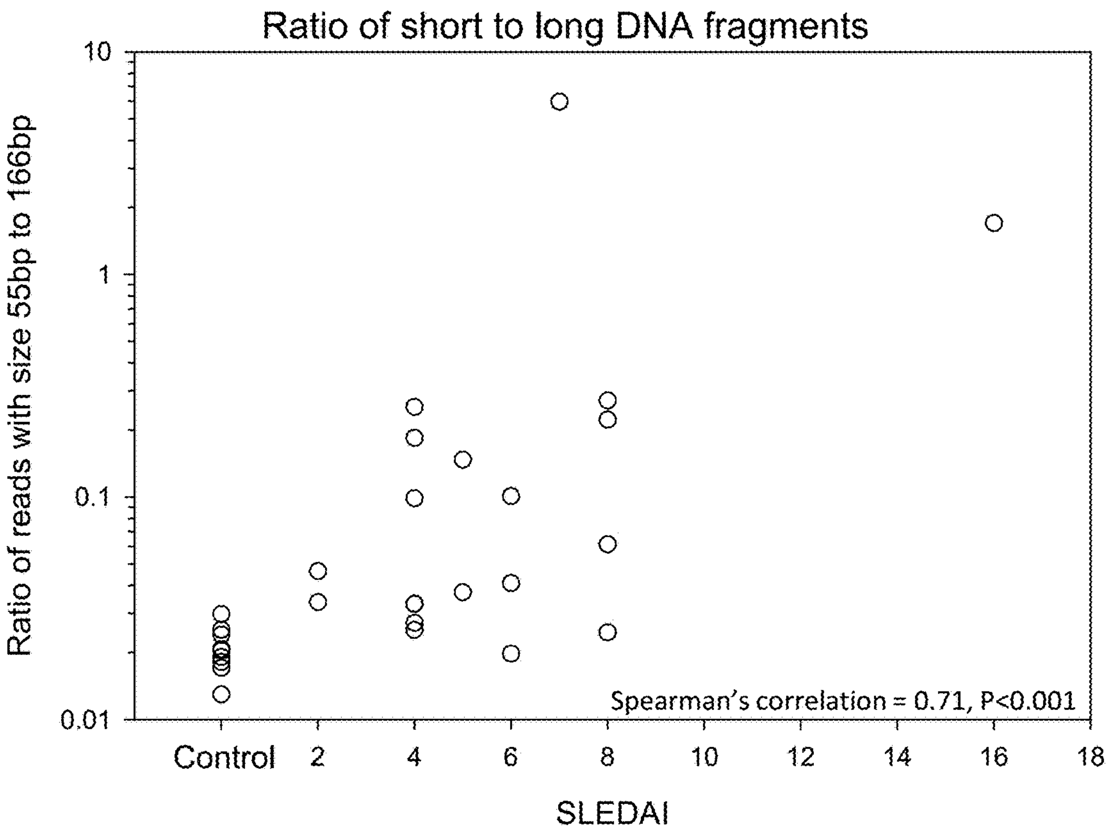
FIGS. 7A-B show a correlation between the ratio of the amounts of short (55 bp) DNA molecules to long (166 bp) DNA molecules in the plasma of a patient on the one hand, and the level of SLE disease activity as reflected by SLEDAI in the patient on the other hand for a group of SLE patients.
Figure 7B:
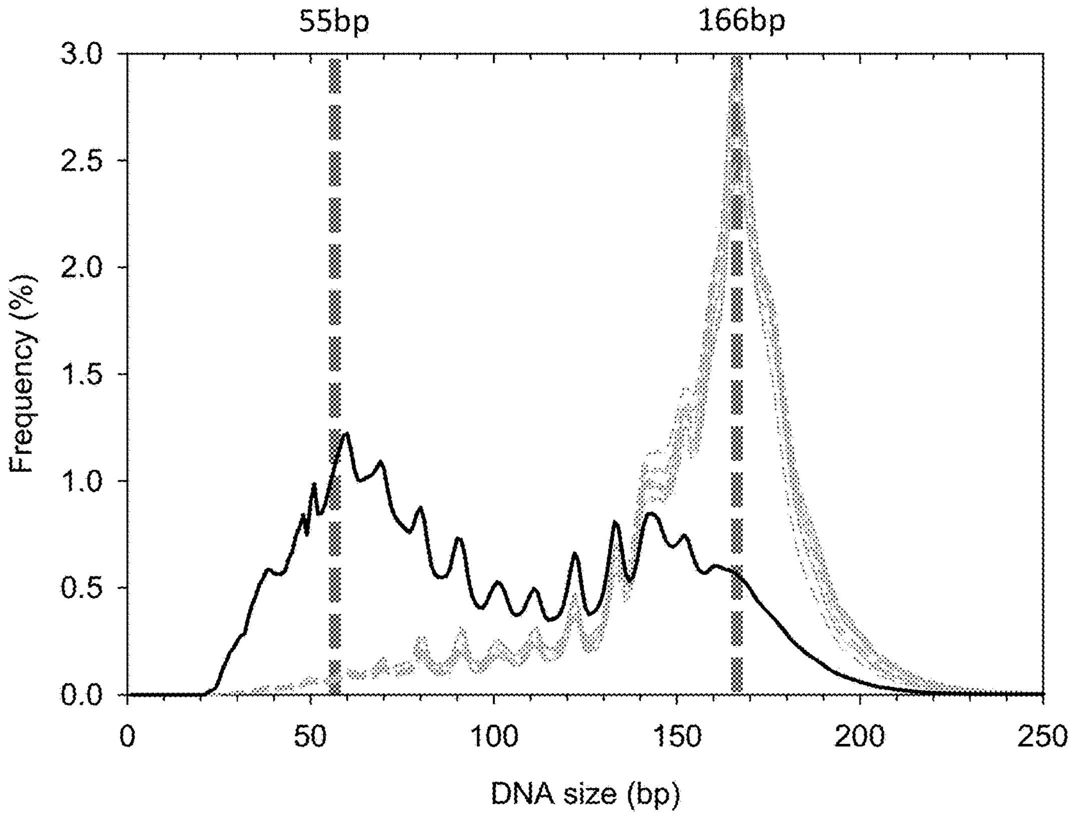
Figure 8:
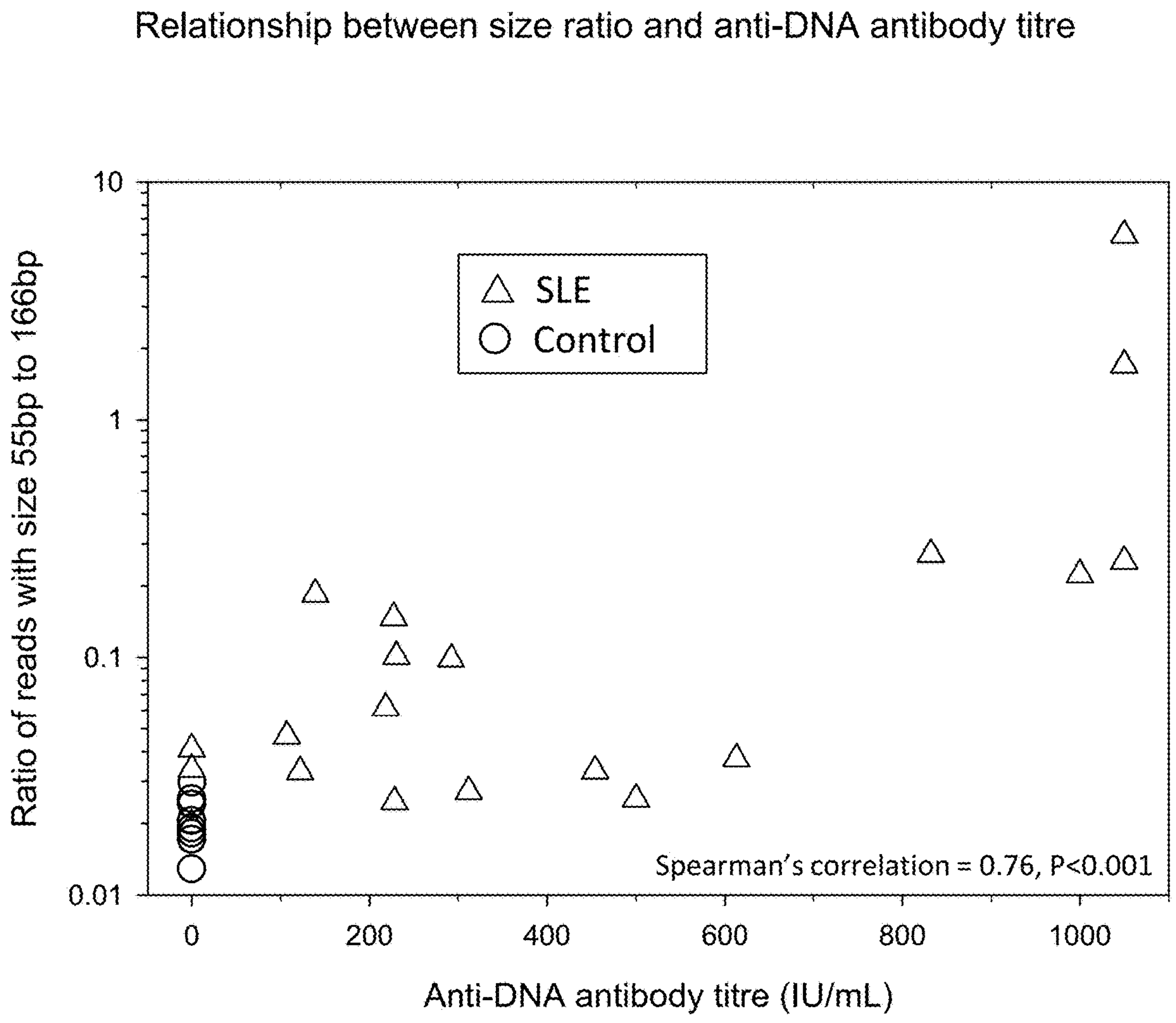
FIG. 8 shows a correlation between the ratio of the amounts of short (55 bp) DNA molecules to long (166 bp) DNA molecules in the plasma of a patient on the one hand, and the anti-DNA antibody titer in the plasma of the patient on the other hand for a group of SLE patients.

To further study this phenomenon, we objectively compared the contribution of short plasma DNA fragments between healthy controls and SLE patients as well as among the SLE patients. For this analysis, we considered plasma DNA molecules smaller than 115 bp as short DNA. However, other cutoffs less than 166 bp could be used. As shown in FIGS. 6A-B, about 10% (mean: 9.7%) of the plasma DNA molecules in healthy individuals were short DNA; however, the percentages of short DNA in SLE patients were generally higher with a mean of 23.8%. This percentage can be over 80% during active disease. Workers in the field have defined active disease or active SLE to correspond to a SLEDAI above 4 to 6. Others have defined active disease by a worsening in the disease, when the SLEDAI increases by 3 to 8 (Ref 32). Furthermore, our analysis showed a statistically significant correlation between the percentage of short DNA and the SLEDAI of SLE patients (Spearman's correlation=0.67, P<0.001). This finding implicated that the increased generation of short DNA may be associated with the augmentation of immune dysregulation in SLE patients with higher disease activity. Therefore, we also determined the ratio of short DNA (55 bp) (other cutoffs could be used) to long DNA (166 bp) and investigated its relationship with the disease activity of the patients. As shown in FIGS. 7A-B, SLE patients had higher ratios when compared to healthy individuals and their ratios significantly correlated to SLEDAI (Spearman's correlation=0.71, P<0.001). As the elevation of anti-ds DNA antibody level is an important serological parameter to indicate SLE exacerbation in current clinical practice, we further studied its relationship with the size ratio of plasma DNA. As shown in FIG. 8, the size ratios also significantly correlated with the antibody levels of SLE patients (Spearman's correlation=0.76, P<0.001).

Figure 9:
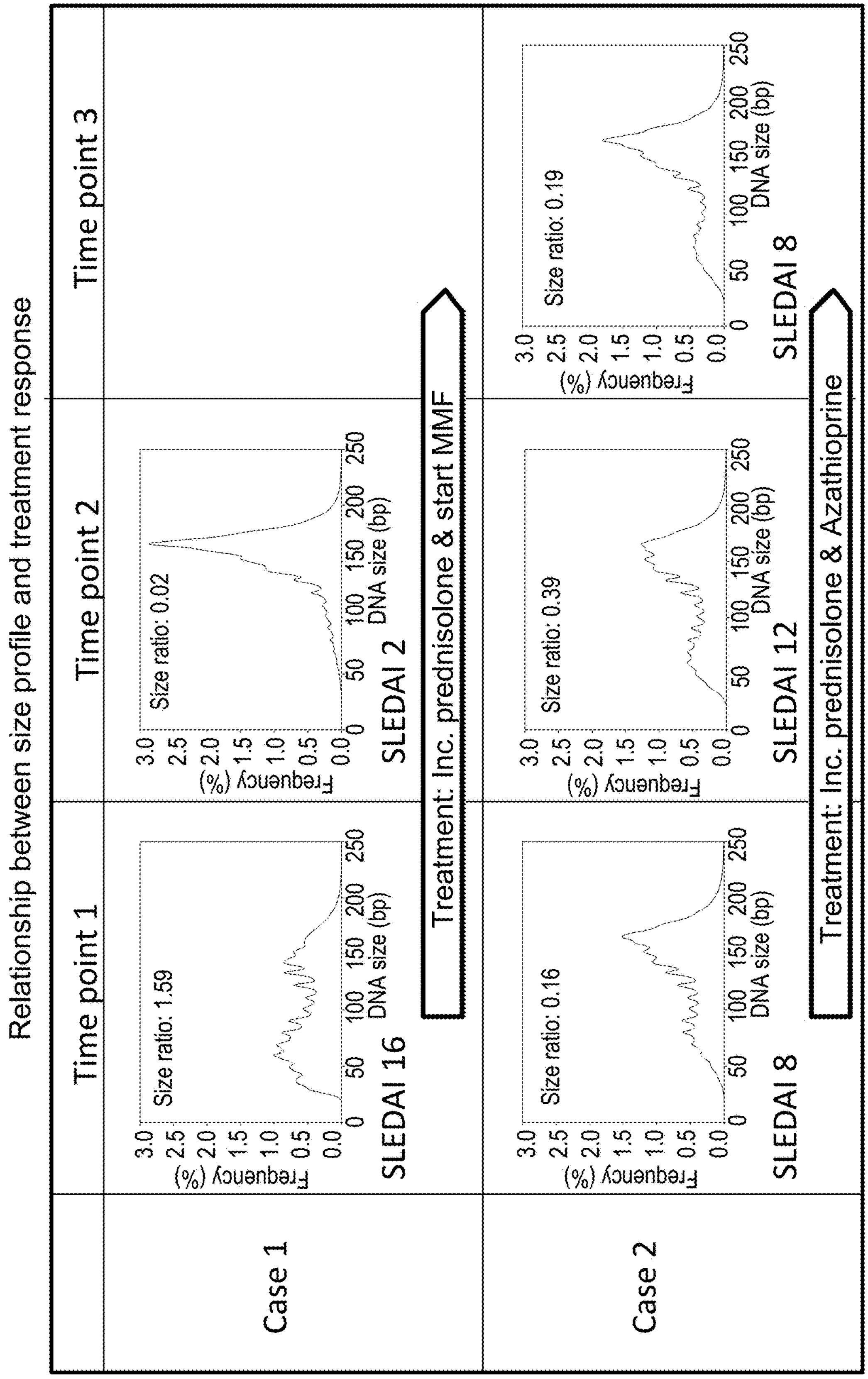
FIG. 9 shows the effects over time of treatments on the size profiles of circulating DNA molecules in the plasma of SLE patients.

Furthermore, we studied the effect of treatment response of two active SLE patients on their plasma DNA size profiles. As shown in FIG. 9, Case #1 had a good treatment response and showed a significant decrease in disease activities from SLEDAI 16 at time-point 1 to SLEDAI 2 at time-point 2. The size profiles clearly exhibited a change from an abnormal to a normal distribution similar to that of healthy individuals. In contrast, Case #2 did not respond well to the treatment and the disease activity remained high in the three time-points. The size profiles of this case showed a consistently abnormal distribution throughout the three time-points. Our data suggest that the change in size profile of circulating DNA in plasma of SLE patients correlates with disease activity and is useful for developing new tools for prognostication, monitoring and assessment of treatment response of SLE patients.

B. Method Based on Size

Figure 10:
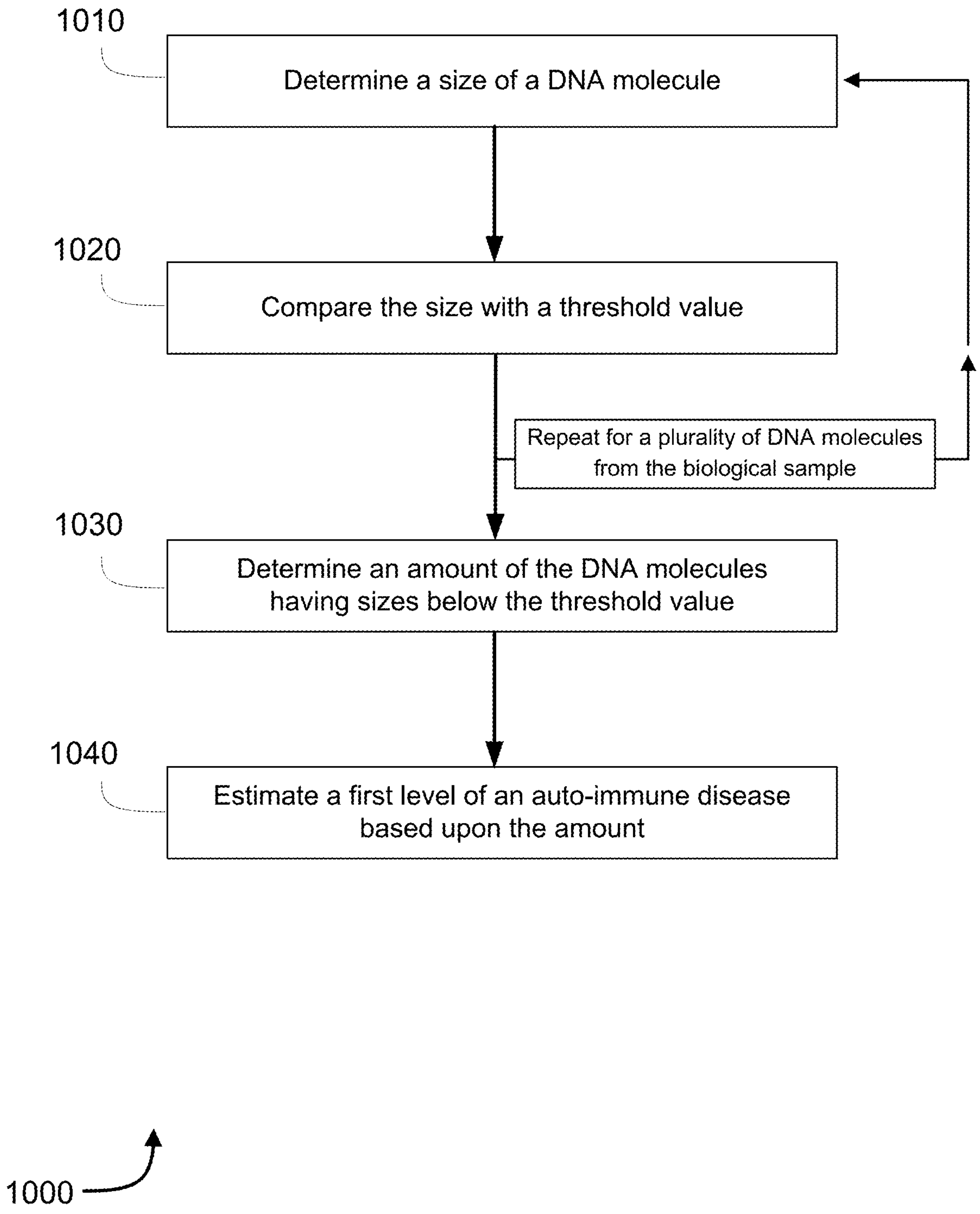
FIG. 10 is a flowchart illustrating a method 1000 for diagnosing an auto-immune disease based on the sizes of circulating DNA molecules according to embodiments of the present invention.

FIG. 10 shows a method 1000 for diagnosing an auto-immune disease based on the sizes of circulating DNA molecules according to embodiments of the present invention. Method 1000 involves analyzing a biological sample of an organism, the biological sample including nucleic acid molecules, wherein at least some of the nucleic acid molecules are cell-free. The method includes analyzing a plurality of DNA molecules from the biological sample, wherein analyzing a DNA molecule comprises: determining a size of the DNA molecule (block 1010), and comparing the size of the DNA molecule with a threshold value (block 1020); determining an amount of the DNA molecules having sizes below the threshold value (block 1030); and estimating a first level of an auto-immune disease in the organism based upon the amount (block 1040).

The biological sample can be obtained as desired from the organism and can originate from any kind of tissue. In some embodiments, the biological sample is a bodily fluid such as blood or plasma. Any processing steps, such as fractionation or purification, can be applied to the biological sample to obtain a plurality of DNA molecules for subsequent analysis.

At block 1010, the sizes of DNA molecules are determined. In some embodiments, the sequencing methods (e.g. massively parallel paired-end sequencing) outlined herein are used in this step. In other embodiments, the sizes are determined in the absence of sequencing. For example, the sizes of one or more molecules can be determined using chromatography or gel electrophoresis. Sizes of DNA molecules can generally be determined as desired, using any available techniques or apparatus. The techniques need not provide the sizes of individual DNA molecules, but preferably provide information about the distribution of sizes of molecules from the biological sample, and the relative abundances of various sizes.

At block 1020, the sizes of DNA molecules in the plurality are compared with a threshold value. The threshold value can be chosen as desired and is 115 bp in some embodiments, as discussed above. Other possible threshold values include, but are not limited to, 90, 95, 100, 105, 110, 120, and 125 bp. The threshold value can be based on data or models concerning the sizes of DNA molecules, for example proposed mechanisms of circulating DNA fragmentation, or reported distributions of cell-free DNA fragment sizes in different tissue types, patient groups, or disease states. Alternatively or in addition, the threshold value can be set empirically, based on the sizes of DNA molecules as determined in the current analysis or previous similar analyses. For example, the threshold value can reflect periodicity observed in the sizes of DNA molecules. If distributions of these sizes are peaked, then the threshold can be chosen relative to one or more peaks. For example, the threshold can be placed a certain number of base-pairs (e.g., 5, 10, 15, 20, 25, 30, 35, 40, 45, 50, 51, 55, or 60) away from one peak, halfway between two peaks, or at a low point between two peaks in the distribution of sizes.

At block 1030, after comparing the sizes of DNA molecules with the threshold value, an amount of DNA molecules having sizes below the threshold value is determined. In some embodiments, the amount is a percentage or fraction. For example, the amount can be the number of DNA molecules having sizes below the threshold, expressed as a percentage of all DNA molecules from the biological sample for which sizes are determined. Alternatively, the amount can be the number of sequence reads having lengths below the threshold value, as a percentage of the number of all sequence reads. If desired, a subset of DNA molecules and/or sequence reads can be selected for determining the amount. For example, the amount can be based on DNA molecules or sequence reads aligning to only a certain portion of the genome, such as one or more chromosomes, or the portion corresponding to coding regions, non-coding regions, repeat regions, or non-repeat regions. As desired, the amount can be relative to a larger total or absolute. For example, the amount can be simply the mass or molar quantity of DNA molecules determined to have sizes below the threshold. The amount can also be the number of such molecules sequenced, or the corresponding number of sequence reads.

At block 1040, the first level of the auto-immune disease in the organism is then estimated based upon the amount. In some embodiments, the first level is a binary prognosis and the disease is considered to be present in the organism if the amount exceeds a pre-determined cutoff. Such a cutoff can be determined as desired, and can correspond a detection limit or a particular level of severity for the disease, for example. Alternatively or in addition, the first level can correlate to degrees of severity for the disease. In this case, multiple cutoffs can be determined, and the level of the disease is calculated based on how the amount of DNA molecules compares with these cutoffs. For example, a cutoff of 10% can correspond to a mild form of the disease, while a cutoff of 20% can correspond to a severe form. The organism would be estimated to have the mild form if the amount (percentage) of DNA molecules having sizes below the threshold value falls between ~10 and 20%. The organism would be estimated to have the severe form if the amount exceeds 20%. Without limitation, the auto-immune disease can be SLE, and the first level can be a level of SLE. The first level of the disease can be estimated in terms of the Systemic Lupus Erythematosus Disease Activity Index (SLEDAI), or the group I-III designations discussed above. The first level of the auto-immune disease can be used as appropriate, for example to design a treatment regimen for the organism or determine a dose of a medication.

In some embodiments, method 1000 further includes estimating a second level of an auto-immune disease in the organism. The auto-immune diseases for which the first level and second level are estimated can be the same disease or different diseases. The second level is generally estimated by identifying two peaks in the sizes of DNA molecules from the biological samples; determining the number of molecules associated with each peak; and calculating the ratio of these numbers.

As used herein, "peak" can have the conventional meaning, i.e. a local or absolute maximum of frequency in a distribution, such as the distribution of sizes for a collection of DNA molecules. "Peak" can also mean a statistic that summarizes or is representative of the distribution, irrespective of the shape of the distribution. A peak can be identified using all DNA molecules from a biological sample or a subset of these molecules. A "peak size" is the size of DNA molecules where a peak in the distribution of sizes is located (for example, where the peak is centered). A "peak number" is the number of DNA molecules associated with a peak (for example, the number of molecules having sizes within a certain range of the peak size).

In some embodiments, the method includes the following additional steps. A first peak size of DNA molecules is designated, wherein the first peak size is less than the threshold value, and a second peak size of DNA molecules is designated, wherein the second peak size is greater than the threshold value. A first peak number is then determined, wherein the first peak number is the number of the DNA molecules having sizes within a specified range of the first peak size. Similarly, a second peak number is determined, wherein the second peak number is the number of the DNA molecules having sizes within a specified range of the second peak size. A ratio of the first peak number to the second peak number is calculated, and a second level of an auto-immune disease in the organism is estimated based upon the ratio.

The first peak size and second peak size can be designated as desired. For example, each peak size can be calculated based on some or all molecules having sizes below or above the threshold value. In some embodiments, the first peak size is equal to the mean, median, or mode size of the DNA molecules having sizes less than the threshold value, and the second peak size is equal to the mean, median, or mode size of the DNA molecules having sizes greater than the threshold value. (As used herein, "mode size" refers to the most frequently occurring size in a population or subpopulation of DNA molecules.) The peak sizes can also be calculated by examining a histogram of sizes determined for DNA molecules from the sample and finding maxima or other high points in this histogram below and above the threshold value. If desired, this histogram can be smoothed prior to calculating one or both peak sizes. The peak sizes can be designated algorithmically or manually. An example of the latter would be setting the second peak size to be 166 bp, as discussed above, or another value based on previously measured distributions of sizes for circulating DNA molecules.

The specified range of sizes for each peak, and in turn the peak number, can also be determined as desired. In embodiments, the first peak number is determined as the number of DNA molecules from the biological sample having sizes within 5, 10, 15, 20, 25, 30, 35, 40, 45, or 50 bp of the first peak size. Likewise, in some embodiments, the second peak number is determined as the number of DNA molecules from the biological sample having sizes within 5, 10, 15, 20, 25, 30, 35, 40, 45, or 50 bp of the second peak size. A peak number can also be determined based on a statistical analysis of the sizes of DNA molecules that are smaller or larger than the threshold value. For example, the range of sizes for the first peak can be equal to the standard deviation of sizes for DNA molecules smaller than the threshold value, or a multiple (e.g., 0.5, 1.5, 2, or 3) of the standard deviation. In addition, a peak number can be simply the number of DNA molecules having sizes below or above the threshold value, as appropriate. Other methods of calculating the peak numbers will be apparent to those of skill in the art.

Once the first peak number and second peak number have been determined, the ratio of these numbers can be calculated, and the second level of an auto-immune disease in the organism can be estimated based upon the ratio. A higher ratio of the first peak number to the second peak number generally indicates a greater relative abundance of small DNA molecules and a higher disease activity. The ratio can be compared with one or more cutoffs to identify whether the disease is present in the organism, or the severity of the disease. If the auto-immune disease is SLE, for example, the cutoffs can distinguish between different SLEDAI levels or patient groupings (i.e., group I, II, or III). Thus, the second level can be a SLEDAI level or patient grouping.

C. Evaluating a Treatment

A method is also provided herein for evaluating a treatment for an auto-immune disease in an organism. A pre-treatment biological sample is obtained from the organism prior to treatment, and is analyzed as discussed above. A pre-treatment level of the auto-immune disease in the organism is then estimated. Subsequent to treatment, a post-treatment biological sample is obtained from the organism and analyzed as discussed above, and a post-treatment level of the auto-immune disease in the organism is estimated. The pre-treatment level of the auto-immune disease is then compared with the post-treatment level of the auto-immune disease to determine a prognosis of the treatment.

The pre-treatment level can be estimated as the first level of the auto-immune disease, or the second level. Similarly, the post-treatment level can be estimated as the first level of the auto-immune disease, or the second level. Preferably, the pre-treatment level and post-treatment level are estimated in the same way (either both first level or both second level) to ensure that these levels are comparable.

When the level of the auto-immune disease falls during the treatment, then the post-treatment biological sample generally has a lower abundance of small DNA molecules than the pre-treatment sample, indicating less disease activity. Accordingly, in some embodiments, the treatment is considered to be effective if the post-treatment level of the auto-immune disease is lower than the pre-treatment level of the auto-immune disease.

The effectiveness of the treatment can also be quantified based on how much the level of the auto-immune disease falls. In some embodiments, the method of evaluating the treatment also includes determining a change between the pre-treatment level and the post-treatment level; and determining a degree of effectiveness based on the change. The change can be expressed as desired, for example as a fraction or percentage of the pre-treatment level, a ratio of the post-treatment level to the pre-treatment level, or a number of SLEDAI levels. The degree of effectiveness can be any appropriate function of this change.

II. RELATIONSHIP BETWEEN METHYLATION DENSITY OF CIRCULATING DNA AND SLE DISEASE ACTIVITY

DNA methylation plays an important role in the regulation of gene expression and cell death. It has been reported that changes in the methylation of DNA in apoptotic cells may provoke lymphocyte activation in SLE[33,34]. In some embodiments, the methylation profile of DNA detected in plasma of SLE patients can be altered and be associated with disease activity.

A. Example Results

Figure 11:
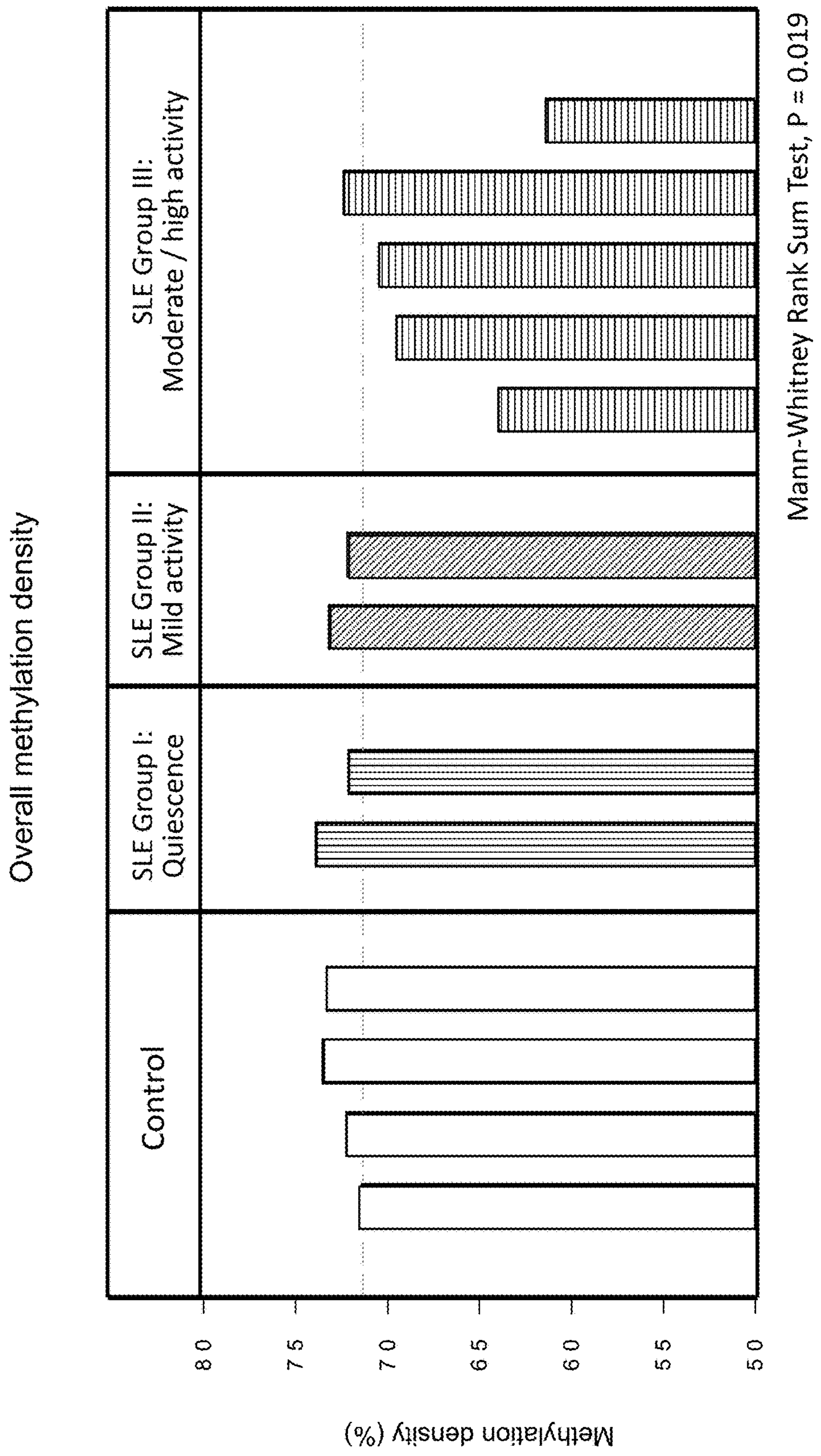
FIG. 11 shows the overall methylation densities for circulating DNA molecules in plasma samples obtained from four healthy individuals and nine SLE patients. Each bar represents one individual or patient.
Figure 12:
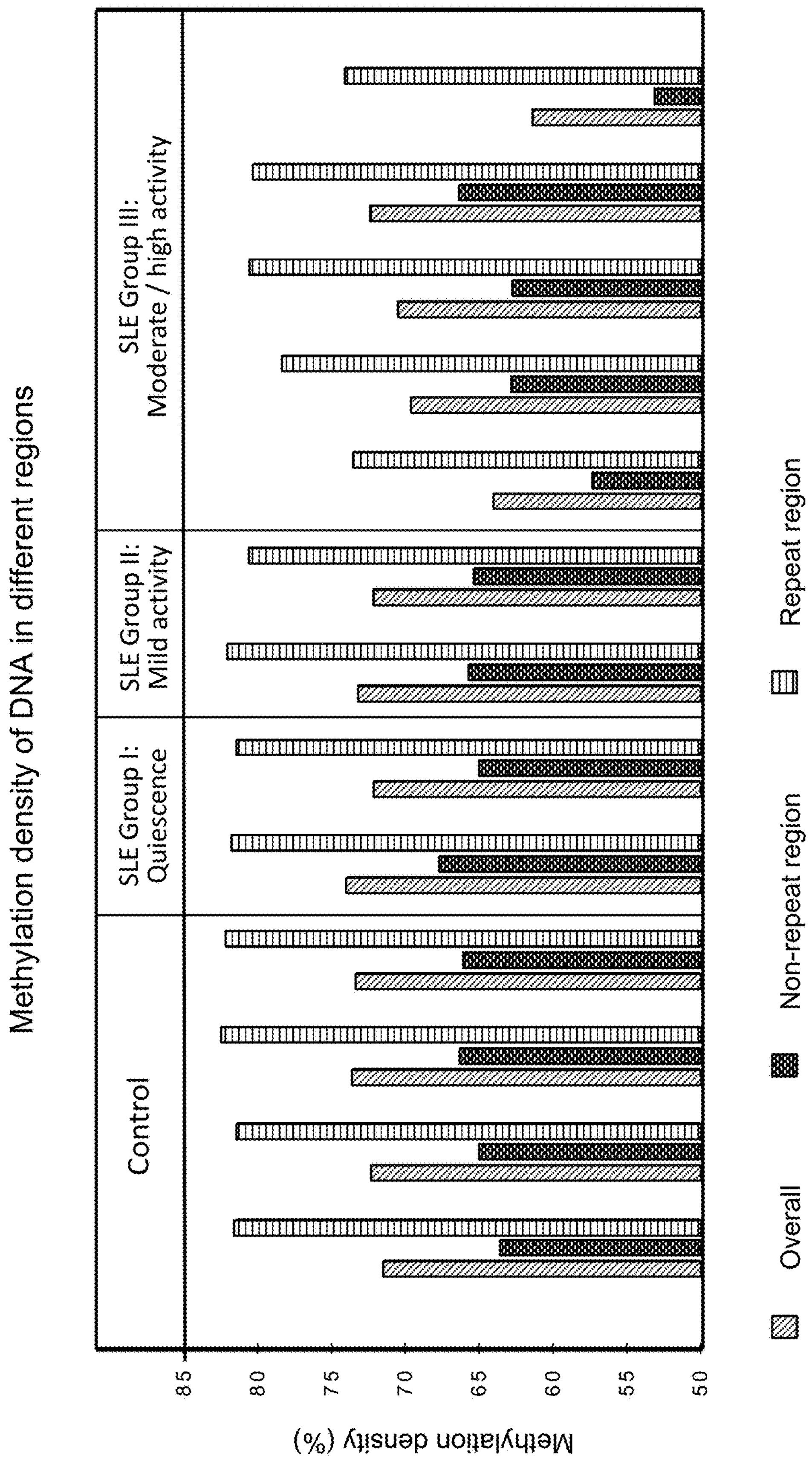
FIG. 12 shows the overall methylation densities, and methylation densities in repeat and non-repeat regions of the genome, for circulating DNA molecules in plasma samples obtained from four healthy individuals and nine SLE patients.

As examples, embodiments used massively parallel paired-end bisulfite sequencing analysis to determine the genome-wide methylation profiles of circulating DNA in the plasma of 4 healthy individuals and 9 SLE patients. First, we quantified the overall methylation density. As shown in FIG. 11, we found that the SLE patients with higher disease activities had statistically significantly reduced overall methylation densities when compared to the healthy individuals as well as SLE patients with mild or in the inactive state (Mann-Whitney Rank Sum Test, P=0.019). Such a reduction in the overall methylation density was observed across the genome as well as in the repeat or non-repeat regions of the genome as illustrated in FIG. 12.

In this example, we next determined the methylation status of smaller segments of the genome. In this analysis, we divided the genome into regions of 1 Mb, termed bins. Other bin sizes smaller or larger than 1 Mb could also be adopted for this analysis. We determined the methylation density of each 1 Mb bin and for all bins in the genome for the healthy controls and SLE patients. We then compared the methylation density of each SLE patient against the mean methylation density of the corresponding bin in the healthy controls. We expressed the difference in the methylation density of a bin between any SLE case and the controls in terms of the number of standard deviations (SDs) determined from the spread of the methylation density values observed among the controls, namely expressed as z-scores. We then assessed the proportion of 1-Mb bins showing similar, lower or higher methylation densities when compared with controls. Bins with z-scores within 3 and −3 are considered showing similar methylation as the controls. Bins with z-scores <−3 are considered to show statistically significant hypomethylation when compared with controls. Bins with z-scores >3 are considered to show statistically significant hypermethylation when compared with controls.

Figure 13:
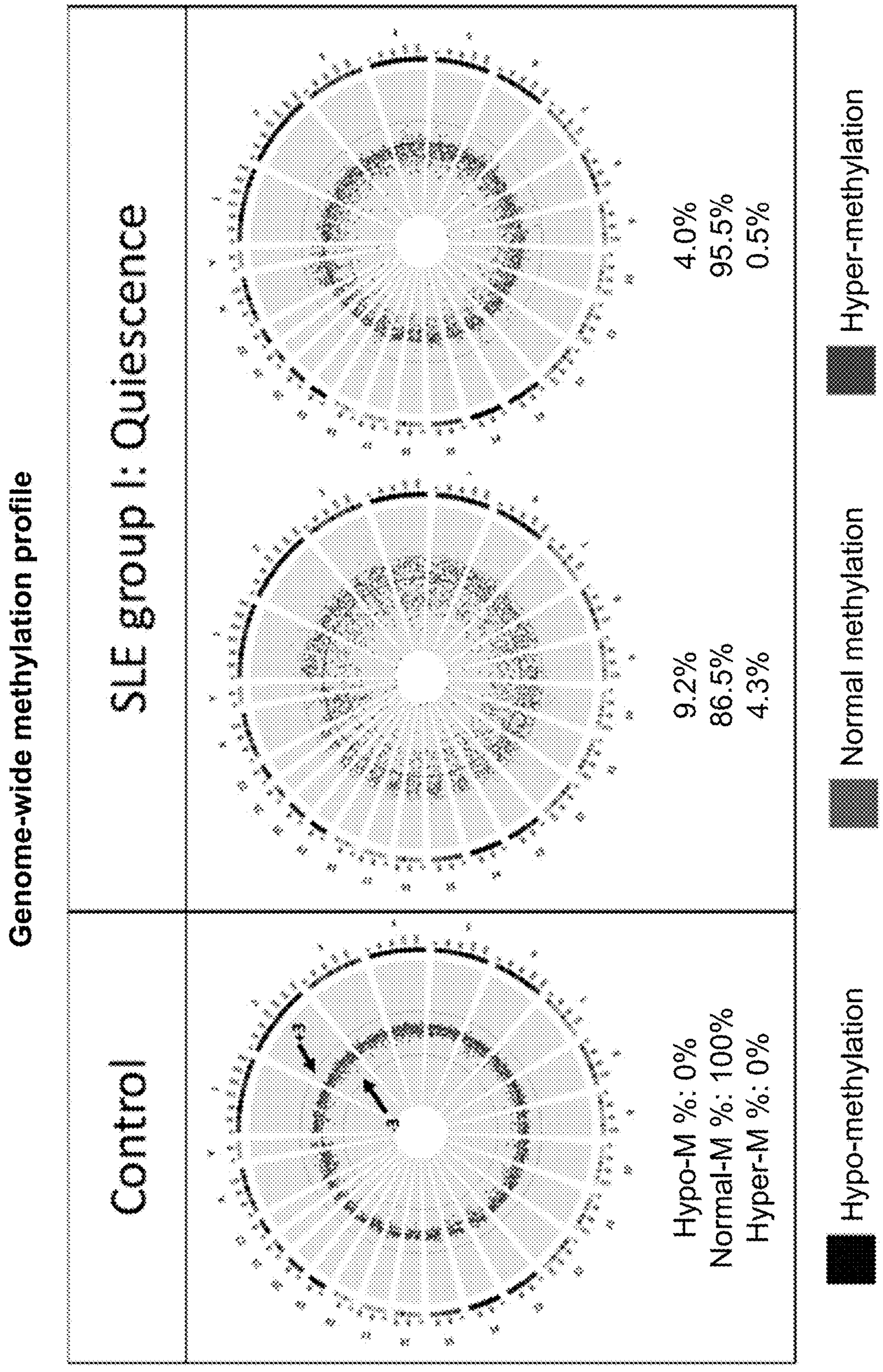
FIG. 13 provides Circos plots illustrating the levels of methylation in 1 Mb regions of the plasma genomes of healthy individuals and group I SLE patients. The radial axis in each plot represents methylation density. The left-most plot shows methylation densities averaged over multiple healthy (control) individuals. The green lines in this plot labeled "+3" and "−3" represent z-scores of +3 and −3, respectively, i.e. methylation densities +3 or −3 standard deviations away from the mean of the methylation densities of corresponding 1 Mb regions. Each remaining plot shows the methylation densities in the genome of a group I SLE patient. A 1-Mb region in which the methylation density has a z-score greater than 3 is considered hypermethylated and is labeled green. A 1-Mb region in which the methylation density has a z-score less than −3 is considered hypomethylated and is labeled red. The percentages of genomic regions considered hypermethylated and hypomethylated for each patient are indicated (M denotes methylation).
Figure 14:
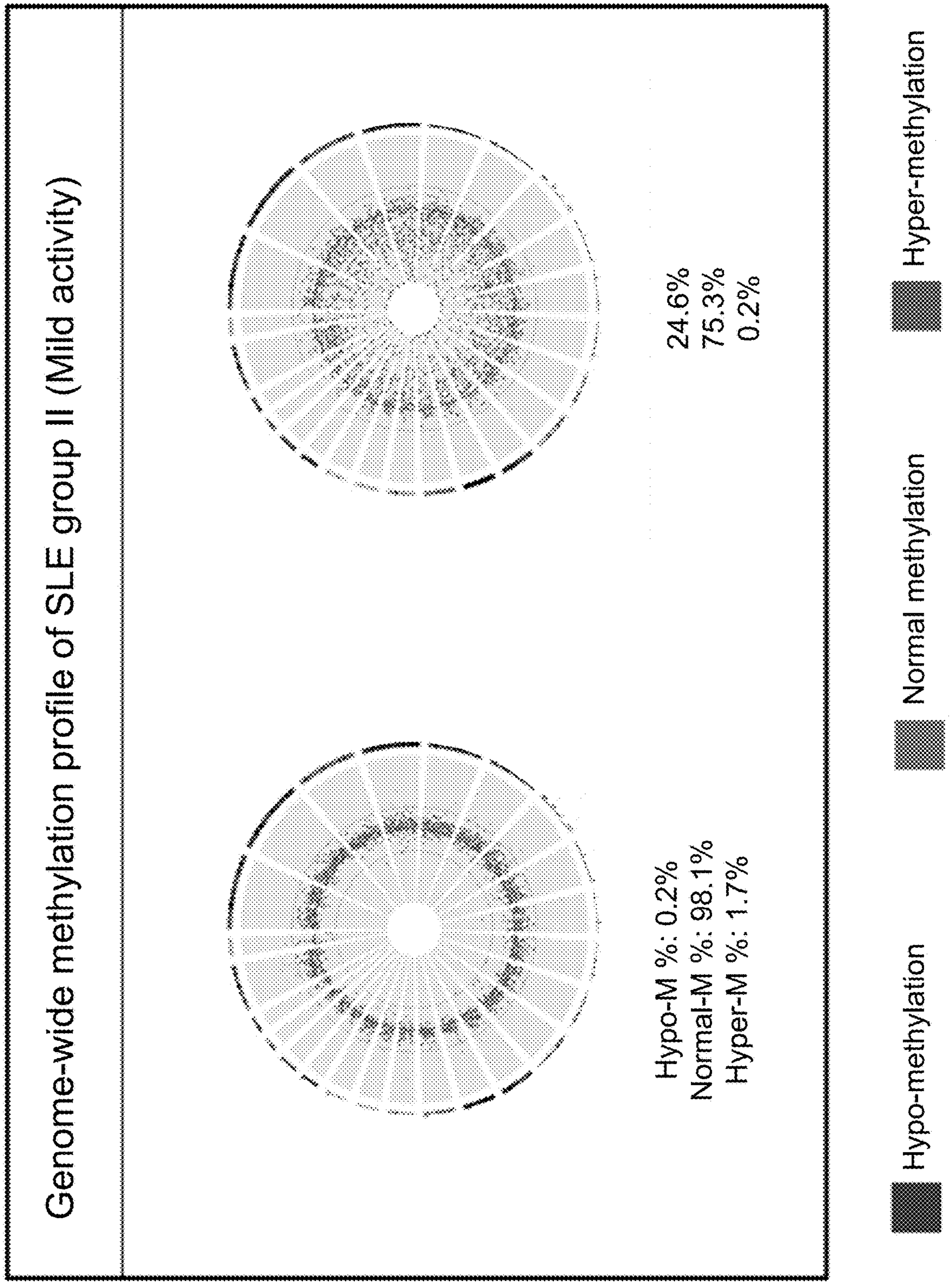
FIG. 14 provides Circos plots illustrating the levels of methylation in 1-Mb regions of the plasma genomes of group II SLE patients. Each plot corresponds to one patient. The 1 Mb regions are labeled as in FIG. 12.
Figure 15:
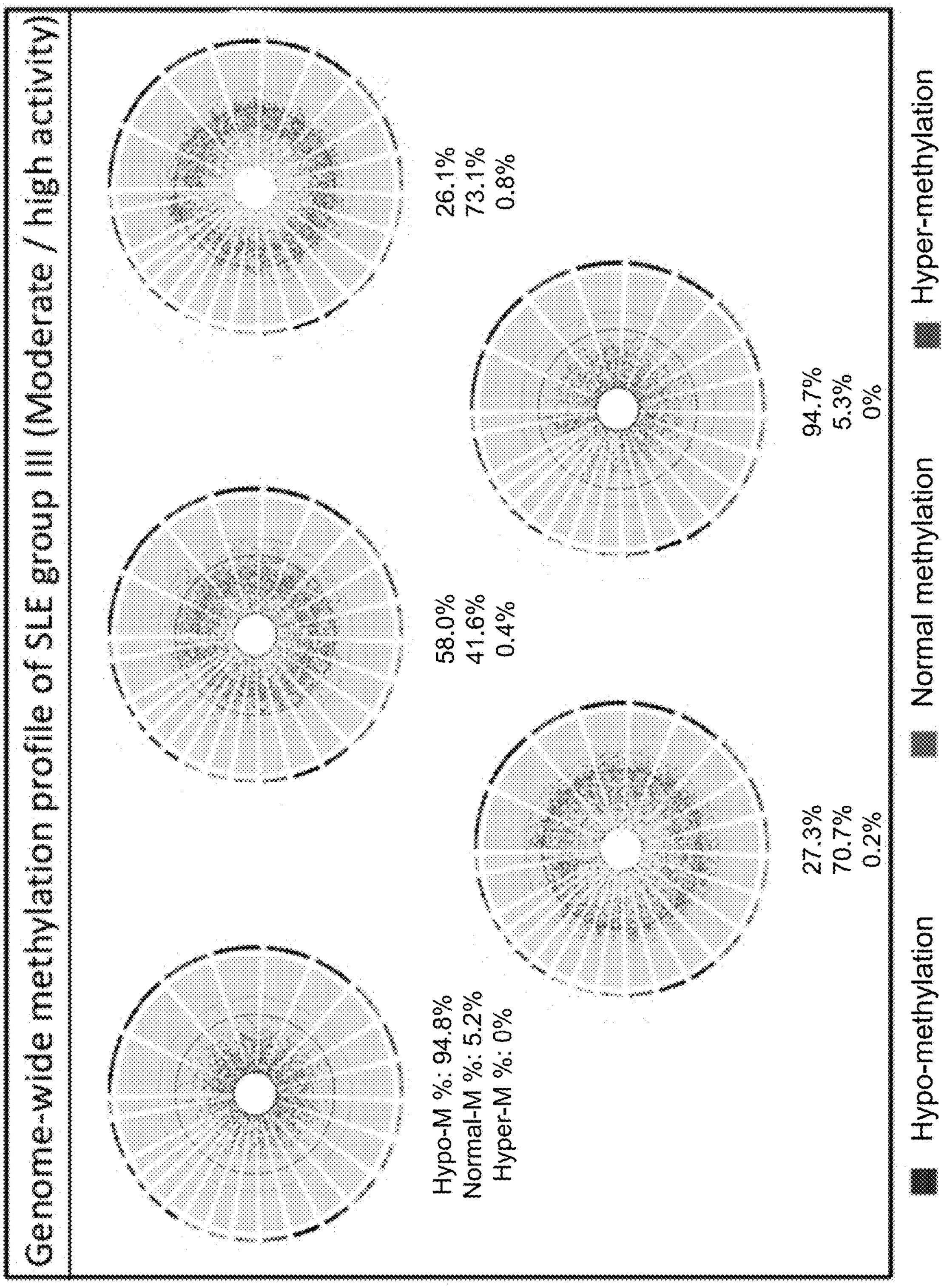
FIG. 15 provides Circos plots illustrating the levels of methylation in 1-Mb regions of the plasma genomes of group III SLE patients. Each plot corresponds to one patient. The 1 Mb regions are labeled as in FIG. 12.
Figure 16:
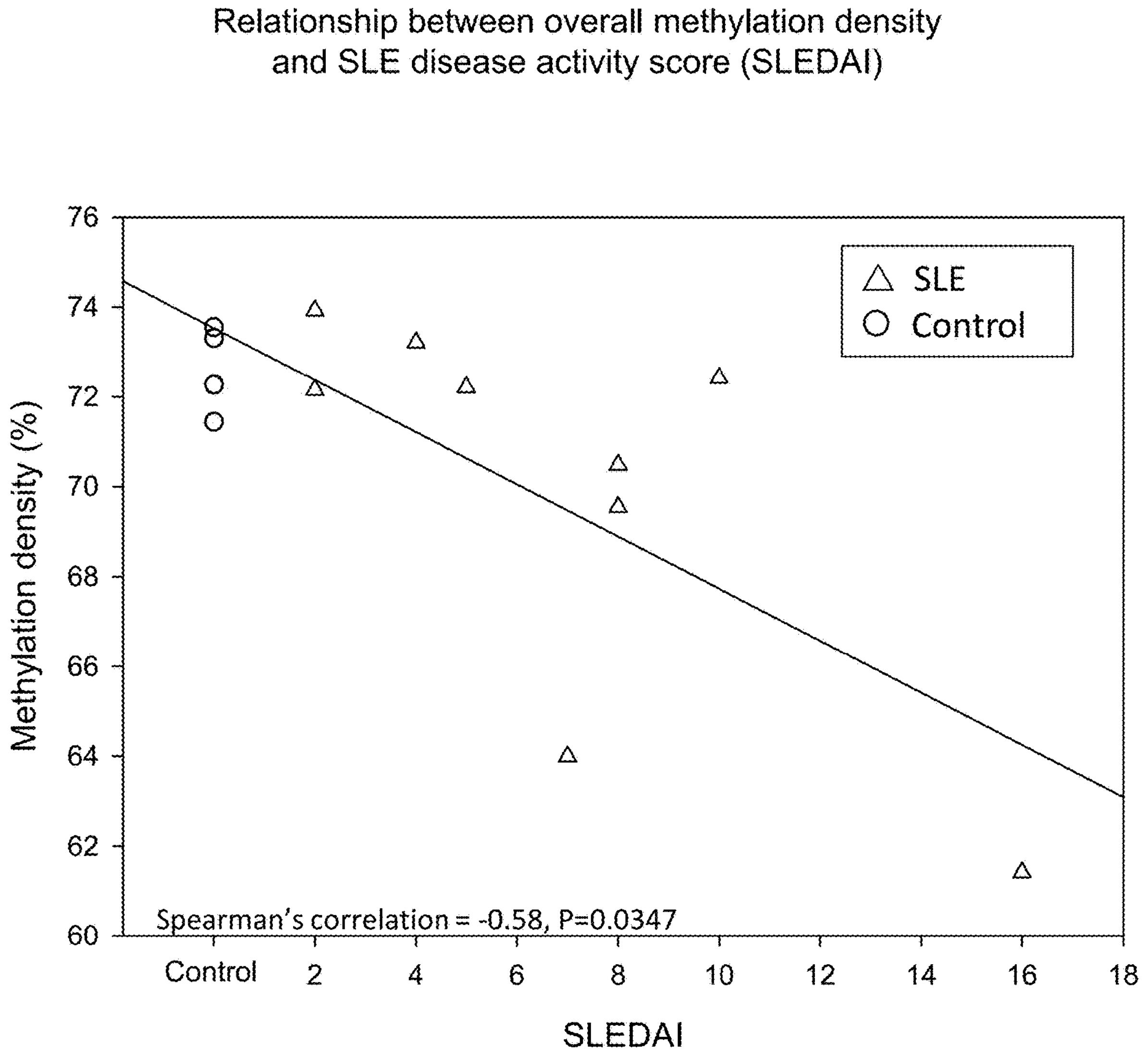
FIG. 16 shows a correlation between the overall methylation density in the plasma genome of a patient (as determined by analyzing circulating DNA in a plasma sample obtained from the patient), and the level of SLE in that patient.
Figure 17:
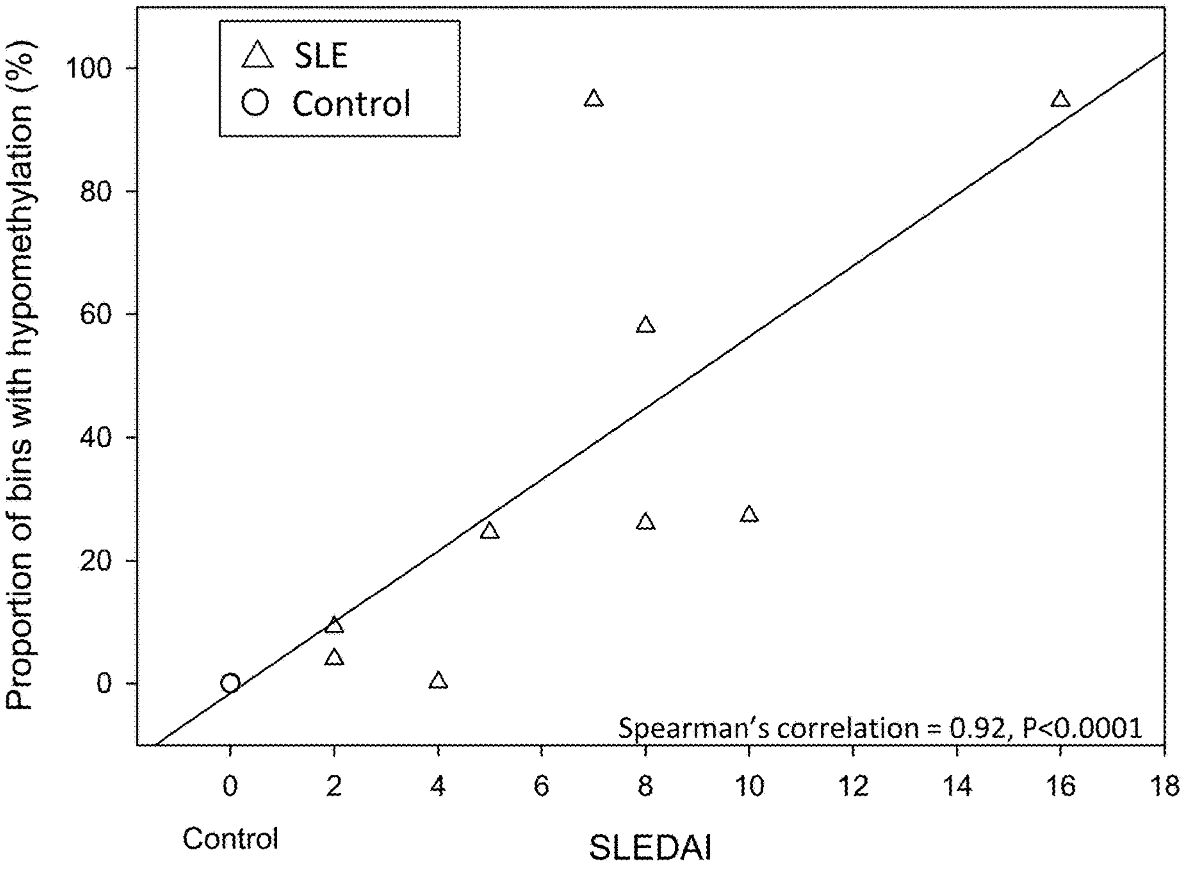
FIG. 17 shows a correlation between the percentage of regions considered hypomethylated in the plasma genome of a patient (as determined by analyzing circulating DNA in a plasma sample obtained from the patient), and the level of SLE in the patient.
Figure 18:
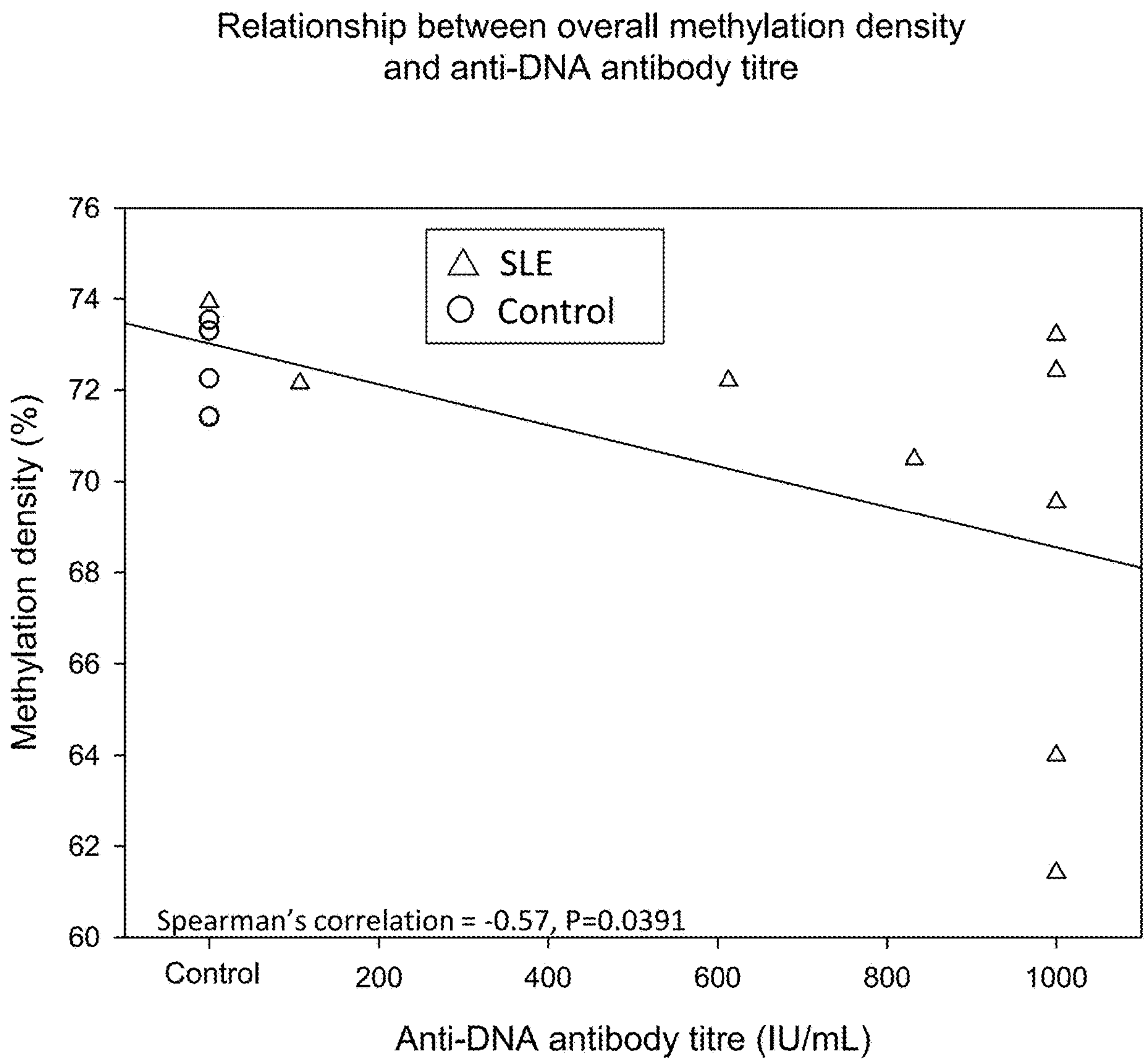
FIG. 18 shows a correlation between the overall methylation density in the plasma genome of a patient (as determined by analyzing circulating DNA in a plasma sample obtained from the patient), and the anti-DNA antibody titer in the plasma of the patient.
Figure 19:
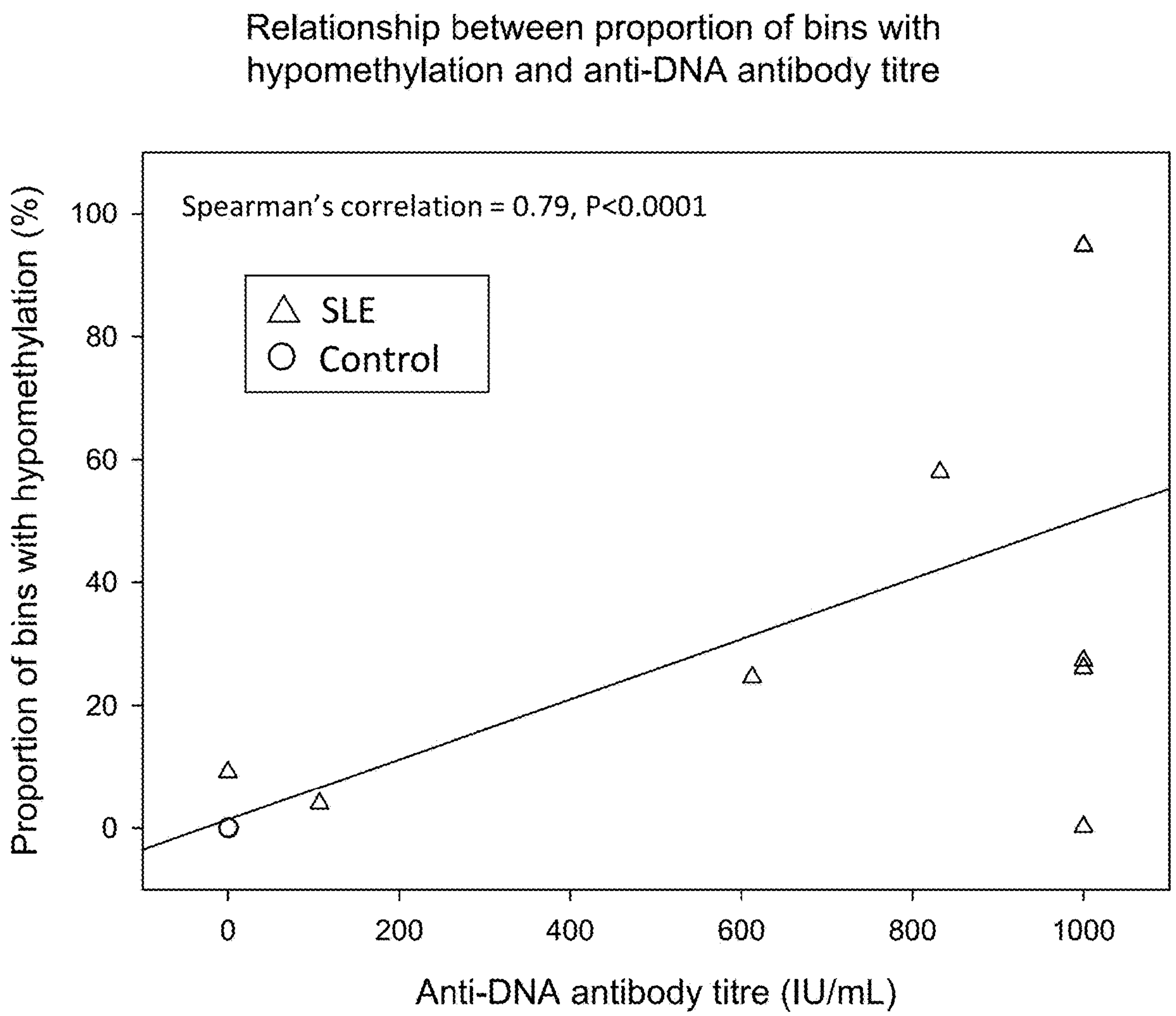
FIG. 19 shows a correlation between the percentage of regions considered hypomethylated in the plasma genome of a patient (as determined by analyzing circulating DNA in a plasma sample obtained from the patient), and the anti-DNA antibody titer in the plasma of the patient.

The data are shown in the Circos plots in FIGS. 13-15. We found that the plasma DNA of all SLE patients showed hypomethylation when compared with controls. The number, proportion or percentage of bins with hypomethylation was increased in SLE patients. The proportions of hypomethylated bins were highest in the SLE patients with higher disease activities (up to 94.8%) when compared to patients with mild or inactive SLE. In addition, our analysis demonstrated that the overall methylation densities and proportion of bins with hypomethylation of plasma DNA of SLE patients had a statistically significant correlation with SLEDAI (FIGS. 16 and 17), Spearman's correlation for the overall methylation densities=−0.58, P=0.0347, Spearman's correlation for the proportion of bins with hypomethylation=0.92, P<0.0001) and anti-ds DNA antibody levels (FIGS. 18 and 19), Spearman's correlation for the overall methylation densities=−0.57, P=0.0391, Spearman's correlation for the proportion of bins with hypomethylation=0.79, P<0.0001). Other z-score cutoffs can be used to adjust the sensitivity and specificity of the analysis.

Figure 20:
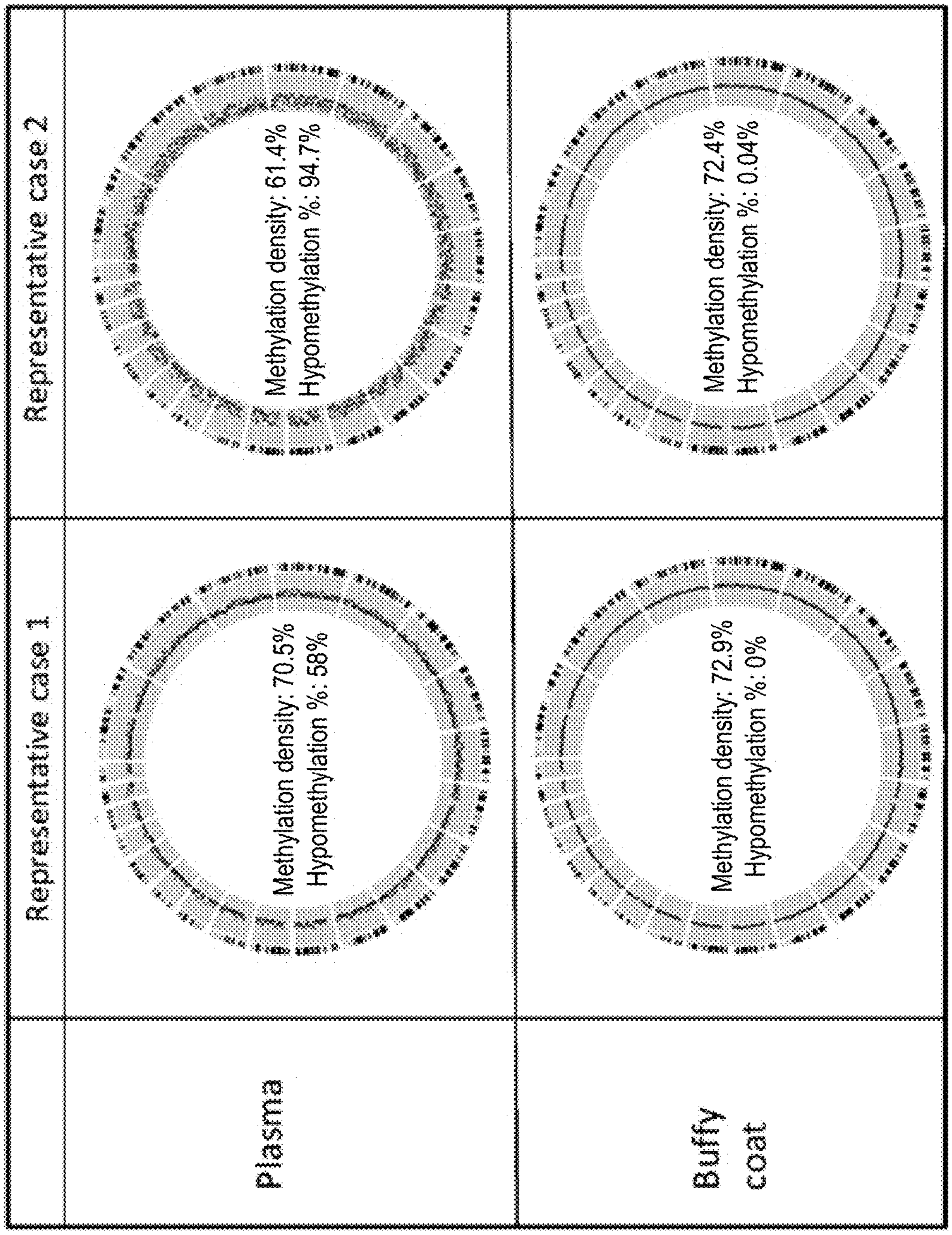
FIG. 20 shows the methylation profiles of plasma DNA and corresponding buffy coat DNA observed for two representative SLE patients.

Our data showed that there is more hypomethylated DNA in the plasma of SLE patients. The degree of hypomethylation correlates with disease activity. Interestingly, when we applied the same analysis to the corresponding blood cell DNA, namely buffy coat, of patients with active SLE, no hypomethylation was detected in the blood cells despite the presence of substantial degree of hypomethylation in plasma (FIG. 20). These data suggest that while the pathogenesis of SLE is related to a heightened immune response in affected individuals, the hypomethylated plasma DNA molecules do not seem to be contributed solely by immune blood cells. This is a surprising finding because previous studies showed that hematological cells are the predominant contributor of plasma DNA in bone marrow transplant recipients[35] and pregnant women[36]. The analysis of methylation profile of plasma DNA is useful for developing new tools for diagnosis, prognosis and monitoring of SLE.

B. Method Based on Methylation

Figure 21:
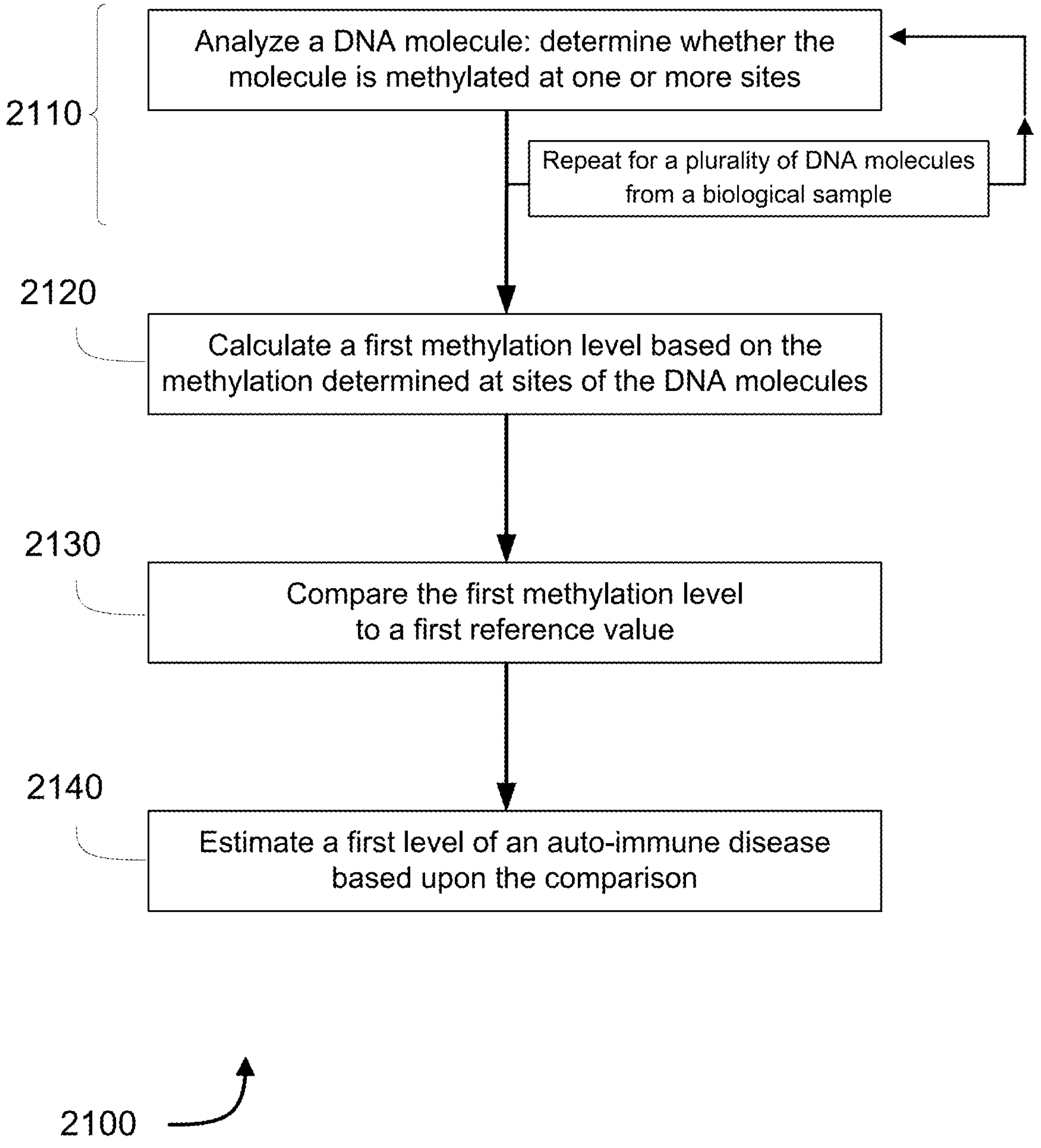
FIG. 21 shows a method 2100 for diagnosing an autoimmune disease based on the methylation of circulating DNA molecules according to embodiments of the present invention

FIG. 21 shows a method 2100 for diagnosing an autoimmune disease based on the methylation of circulating DNA molecules according to embodiments of the present invention. Method 2100 involves analyzing a biological sample of an organism, the biological sample including nucleic acid molecules, wherein at least some of the nucleic acid molecules are cell-free. The biological sample can be obtained from the organism as desired and processed prior to analysis, as described above.

At block 2110, a plurality of DNA molecules from the sample is analyzed. Analyzing a DNA molecule includes determining whether the DNA molecule is methylated at one or more sites. The analysis can be performed using massively-parallel or single-molecule sequencing, preferably methylation-aware sequencing. Any sequencing or other technique can be used to analyze each DNA molecule of the plurality. If desired, sequence reads can be aligned to a reference genome sequence and the locations of individual methylated or non-methylated sites in the reference genome sequence can be determined. The analysis can include or exclude DNA molecules having certain characteristics, for example DNA molecules aligning to certain genomic regions, so that data from only a selected subset of DNA molecules in the biological sample are used in subsequent method steps. In some embodiments, the DNA molecules included in the analysis, and in turn used to calculate the first methylation level, have a specified size or range of sizes. In some embodiments, no DNA molecules are excluded from the analysis.

At block 2120, a first methylation level is calculated based on the methylation determined at sites of the DNA molecules. The first methylation level can be a methylation index or a methylation density as defined above. The sites for which the first methylation level is calculated can be selected as desired to have specific characteristics. For example, the sites can be CpG sites or can occur within certain genomic regions, for example chromosomes or portions thereof, repeat regions, non-repeat regions, coding regions, non-coding regions, or CpG islands. In some embodiments, the first methylation level is calculated for all informative sites in the DNA molecules analyzed.

In some embodiments of method 2100, calculating the first methylation level includes normalization. For each DNA molecule analyzed, an amount of the one or more sites that are methylated is calculated. The amounts for the plurality of DNA molecules are summed to obtain a total amount, and the total amount is normalized to obtain the first methylation level. The normalization can be carried out as desired or as described below. For example, the total amount of methylated sites can be divided by the number of DNA molecules in the plurality or by the total length of DNA represented by these molecules. The total amount of methylated sites can also be transformed by a function that reflects variation in the sizes of the DNA molecules, and corrects for the tendency of shorter DNA molecules to have lower methylation densities.

At block 2130, the first methylation level is compared to a first reference value. The first reference value can be a methylation level calculated using one or more control biological samples, e.g. samples obtained from organisms known or assumed to lack the auto-immune disease. Preferably, the first reference value and first methylation level are calculated in a similar fashion and reflect the same set of sites, or an overlapping set of sites. The first reference value can be based on previous data and/or theoretical considerations. In some embodiments, the first reference value is a methylation density.

Comparing the first methylation level to the first reference value can include determining whether first methylation level is greater than or less than the first reference value, and by how much. For example, the comparison can involve calculating a difference in percent methylation densities. A first methylation level that exceeds the first reference value indicates hypermethylation, while a first methylation level that falls below the first reference value indicates hypomethylation. Instead or in addition, the comparison can involve calculating a ratio of the two quantities. The comparison can also include calculating a statistical measure, such as a confidence interval or uncertainty, to characterize the difference or ratio of the first methylation level and first reference value.

At block 2140, the first level of the auto-immune disease is estimated based on the comparison at block 2130. The first level can be a level of SLE or a patient grouping, for example, and can reflect the magnitude of observed hypermethylation or hypomethylation. Greater hypomethylation can reflect higher disease activity. The first level of the auto-immune disease can be used as appropriate, for example to design a treatment regimen for the organism or determine a dose of a medication.

In some embodiments of method 2100, the methylation at specific sites in the genome of the organism is examined. Calculating the first methylation level can include, for each of a plurality of first sites, determining a respective number of DNA molecules that are methylated at the first site. The calculation can also include determining the number of DNA molecules containing each first site that are unmethylated, and thus the fraction of DNA molecules (or reads) containing each first site that are methylated. Thus, a methylation index can be calculated at one or more of the first sites. Instead or in addition, one or more methylation densities can be calculated for the region or regions containing the first sites. The first methylation level can be calculated as desired based on the respective number of DNA molecules methylated at the plurality of first sites. To estimate the first level of the auto-immune disease, this first methylation level is then compared to a first reference value as discussed above, for example a reference value calculated using data for the first sites in a healthy organism.

In these embodiments, any number of first sites can be examined, and the first sites can be chosen using any appropriate criteria. For example, the first sites can be chosen on the basis of how many analyzed DNA molecules contain each site, and thus how much certainty can be placed on a methylation index for that site or a methylation density for a region containing that site. Alternatively, the first sites can be chosen to represent portions of the genome having common characteristics, such as sites within the same chromosome, sites all within coding or non-coding regions, or sites all within repeat or non-repeat regions. Another possibility is that the first sites are chosen to represent disparate regions of the genome. For example, a plurality of sites can be chosen to evenly represent all the chromosomes. The first sites can also be chosen based on whether they fall within genes implicated in the auto-immune disease or related phenomena (e.g., apoptosis), or fall within regions of the genome involved in regulating these genes.

Method 2100 can also include examining methylation at a plurality of second sites. Data for the first sites and second sites can be analyzed in the same or similar ways. For each of a plurality of second sites, a respective number of DNA molecules that are methylated at the second site is determined. A second methylation level is then calculated based on the respective numbers of DNA molecules methylated at the plurality of second sites. The second methylation level is compared to a second reference value, and a second level of the auto-immune disease in the organism is estimated based upon the comparison of the second methylation level to the second reference value.

The first sites and second sites can be chosen using similar criteria. In some embodiments, the first sites and second sites are chosen to provide complementary information about the methylation of DNA molecules in the biological sample. For example, the first sites can occur in repeat regions of the genome of the organism, and the second sites can occur in the non-repeat regions of the genome of the organism. Alternatively, the first sites can represent coding regions, while the second sites represent non-coding regions. Another alternative is for the first sites to occur within one chromosome or region of the genome, while the second sites occur within a different chromosome or region. Thus, the first sites and second sites can be in non-overlapping regions. The first and second sites can also be chosen in order to compare methylation in one region of the genome with methylation in the genome as a whole. For example, the first sites can be concentrated in one region of the genome, while the second sites can be distributed throughout the genome.

After estimating first and second levels of the auto-immune disease, based on the methylation levels calculated for the plurality of first sites and the plurality of second sites, respectively, the first and second levels can be compared with each other. In some embodiments of the present methods, the first level of the auto-immune disease is compared with the second level of the auto-immune disease to determine a classification of whether the organism has the auto-immune disease. For example, if the first and second levels, respectively representing hypomethylation in repeat and non-repeat regions of the organism's genome, are both high, then the organism can be placed into a classification for having the disease. In another example, if one level is much higher than the other, then hypomethylation in the organism's genome may be non-uniform, and an appropriate classification for the organism can be determined. It will be recognized that the meaning of the comparison between the first level and second level depends on what criteria are used to select the first sites and second sites. Comparing the first level with the second level can include determining a parameter between the first level and the second level, and comparing the parameter to a cutoff value. This parameter can include a difference or ratio of the first level and second level, or other function of the first level and second level. For example, if the ratio of the first level to the second level exceeds a cutoff value, then the organism can be classified as having the auto-immune disease.

C. Multiple Regions

Figure 22:
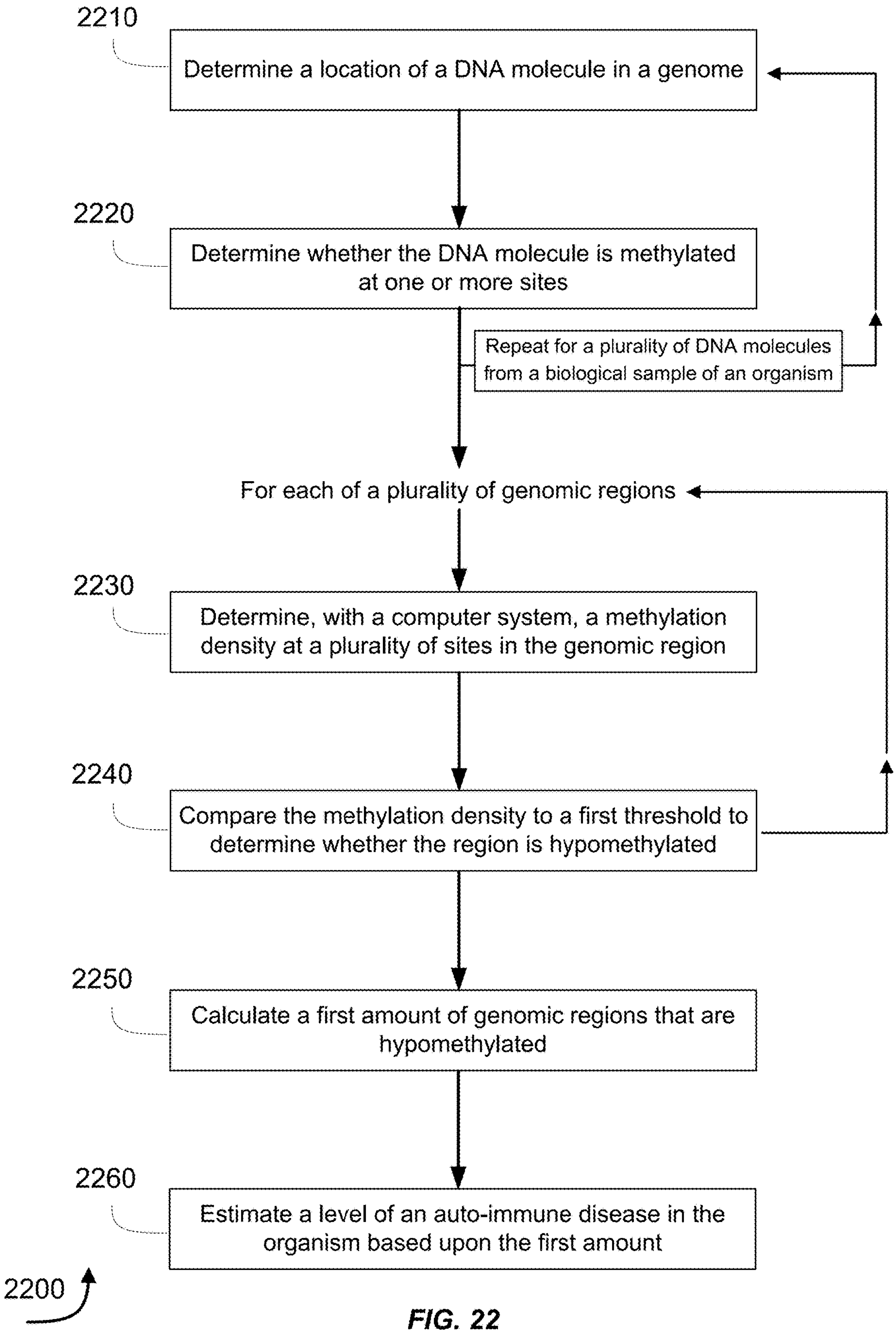
FIG. 22 shows a method 2200 of identifying hypomethylation or hypermethylation in multiple regions of the genome of an organism according to embodiments of the present invention.

FIG. 22 shows a method 2200 of identifying hypomethylation or hypermethylation in multiple regions of the genome of an organism according to embodiments of the present invention. The method is for analyzing a biological sample of an organism, the biological sample including nucleic acid molecules, wherein at least some of the nucleic acid molecules are cell-free.

At blocks 2210 and 2200, the plurality of DNA molecules from the biological sample are analyzed. These blocks are repeated for each DNA molecule analyzed. At block 2210, the location of a DNA molecule in a genome of the organism is determined. The location can be determined by sequencing the DNA molecule using a single-molecule or massively parallel sequencing technique, as discussed above, and aligning the sequence with a reference genome sequence. The alignment can be performed as desired. The reference genome sequence can be a consensus (e.g., published)

sequence or the sequence of one or more individual organisms. If feasible, the reference genome sequence can be the sequence of the organism from which the biological sample is obtained.

At block 2220, it is determined whether the DNA molecule is methylated at one or more sites. Methylation, or the absence thereof, can be detected at specific sites using methylation-aware sequencing, such as bisulfate sequencing. Preferably, an appropriate sequencing method is chosen such that blocks 2210 and 2220 can be carried out in a single sequencing step for each molecule. The sites interrogated for methylation at block 2220 can be all possible sites in the reference genome sequence, all sites encountered during sequencing of the plurality of DNA molecules, or a subset thereof. These sites can be pre-selected, as discussed above, or can be identified during the analysis.

Blocks 2230 and 2240 are carried out for each of a first plurality of genomic regions. Each genomic region is a region of the genome of the organism from which the biological sample was obtained. A genomic region can be a chromosome or portion thereof. If desired, the genomic regions can be delineated in terms of the reference genome sequence. In some embodiments, the genomic regions are non-overlapping and/or contiguous. In some embodiments, the genomic regions are bins of equal size. The size of each genomic region or bin can be from about 100 kb to about 10 Mb. In some embodiments, each genomic region or bin is about 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, or 10 Mb in size.

At block 2230, for each genomic region, a methylation density at a plurality of sites in the genomic region is determined with a computer system, based on the analysis of DNA molecules in the genomic region. The methylation density can be determined as desired and/or as described above. The methylation density can take into account all possible methylation sites within the genomic region, all sites analyzed, or a subset thereof. In some embodiments, the methylation density is expressed as a percentage.

At block 2240, the methylation density determined for each genomic region is then compared to a first threshold to determine whether the region is hypomethylated. In some embodiments, a reference value is calculated and the first threshold is set with respect to the reference value. For example, the reference value can be a statistical value, such as the median or mean, of a set of control methylation densities, which are determined for a plurality of genomic regions of one or more other organisms. The other organisms can be known or assumed to not suffer from the auto-immune disease, or to have an appropriately low level of the auto-immune disease.

A measure of spread (for example, standard deviation, standard error, variance, or statistical uncertainty) can be calculated for these control methylation densities, and the first threshold can be the measure of spread (or a multiple thereof) subtracted from the reference value. For example, the first threshold can represent a z-score, as calculated with respect to the distribution of control methylation densities, of −1, −2, or −3. In other words, the first threshold can be the mean of the control methylation densities minus three times (for a z-score of −3) the standard deviation of the control methylation densities. In general, the first threshold for a genomic region can reflect statistical variation in the methylation densities determined for a plurality of genomic regions. In some embodiments, a genomic region is considered to be hypomethylated if the methylation density for the genomic region is less than the first threshold.

At block 2250, a first amount of genomic regions that are hypomethylated is calculated. The first amount can be the number of genomic regions in the organism that are hypomethylated, or the fraction or percentage of all genomic regions that are hypomethylated. Alternatively or in addition, the first amount can be the total amount of sequence space spanned by the hypomethylated genomic regions, or the fraction of the total length of the organism's genome that these regions span.

At block 2260, a level of an auto-immune disease in the organism is estimated based upon the first amount. The level can be a level of SLE, and can be stated in terms of SLEDAI or a patient grouping. Higher first amounts can be associated with higher levels of the auto-immune disease, or greater disease activity. The estimated level of the auto-immune disease can be used as appropriate, for example to design a treatment regimen for the organism or determine a dose of a medication.

In embodiments of method 2200, genomic regions can also be identified as hypermethylated. In some embodiments, a second plurality of genomic regions is identified in the genome of the organism from which the biological sample was obtained. The second plurality of genomic regions can be the same as the first plurality of genomic regions, or can be different. For example, the second plurality of genomic regions can have different sizes from the first plurality of genomic regions, be different in number, and/or have boundaries in different locations within a reference genome sequence.

For each of the second plurality of genomic regions, the methylation density is compared to a second threshold to determine whether the region is hypermethylated. In some embodiments, a region is considered hypermethylated if the methylation density exceeds the second threshold. The second threshold can be set as desired, and in some embodiments is set in analogy to the first threshold discussed above. For example, a set of control methylation densities can be determined for a plurality of genomic regions of one or more other organisms, and the mean and standard deviation of these control methylation densities can be calculated. The second threshold can then be set as the mean plus a multiple (for example, 3) of the standard deviation. The mean of the control methylation densities thus serves as a reference value. Other statistical values (e.g., median) calculated from the control methylation densities can serve as the reference value instead.

In some embodiments, a difference between the second threshold and a reference value equals the difference between the reference value and the first threshold. Thus, the first and second thresholds are equally spaced from the reference value. Generally, the first and second threshold for a genomic region can be determined based on a statistical variation in the methylation densities determined for a plurality of genomic regions.

Once the methylation density of each genomic region in the second plurality of genomic regions has been compared to a second threshold, a second amount of genomic regions that are hypermethylated is calculated. The second amount can be calculated in analogy to the first amount discussed above. For example, the second amount can be the number of genomic regions that are hypermethylated, or the fraction or percentage of all genomic regions in the second plurality that are hypermethylated. The level of the auto-immune disease in the organism can then be estimated, and this estimate can be based on the second amount as well as the first amount. In some cases, a higher second amount (i.e., more hypermethylation) can indicate a higher level of the auto-immune disease, whereas in other cases this indicates a lower level. It will be recognized that any comparisons between the first amount and second amount should take into account how the first and second pluralities of genomic regions are designated.

III. RELATIONSHIP BETWEEN METHYLATION DENSITY AND SIZE OF CIRCULATING DNA IN SLE PATIENTS

The change in methylation profile of plasma DNA can be associated with an altered size distribution of plasma DNA in SLE patients. By using the data generated from the massively parallel paired-end bisulfite sequencing analysis of plasma DNA of the 4 healthy individuals and 9 SLE patients, we determined the methylation densities of DNA in a range of sizes (20-250 bp). This analysis also indicates that the characteristic plasma DNA size profiles associated with SLE could be observed from both the data obtained by massively parallel paired-end sequencing without bisulfite conversion as well as by massively parallel paired-end bisulfite sequencing.

Figure 23:
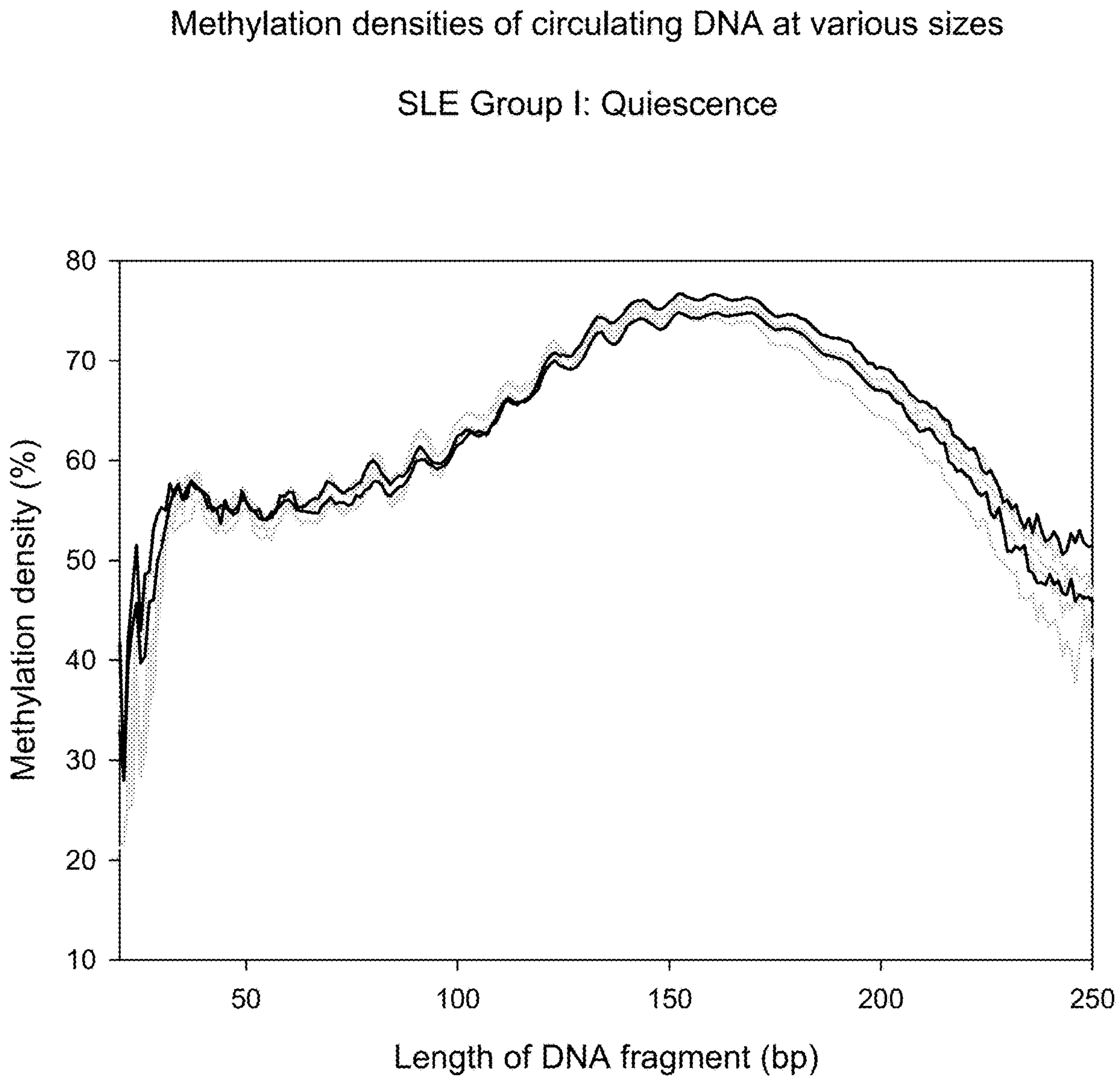
FIG. 23 shows the methylation densities of circulating DNA molecules, obtained from plasma samples of group I SLE patients, as a function of the sizes of those molecules.
Figure 24:
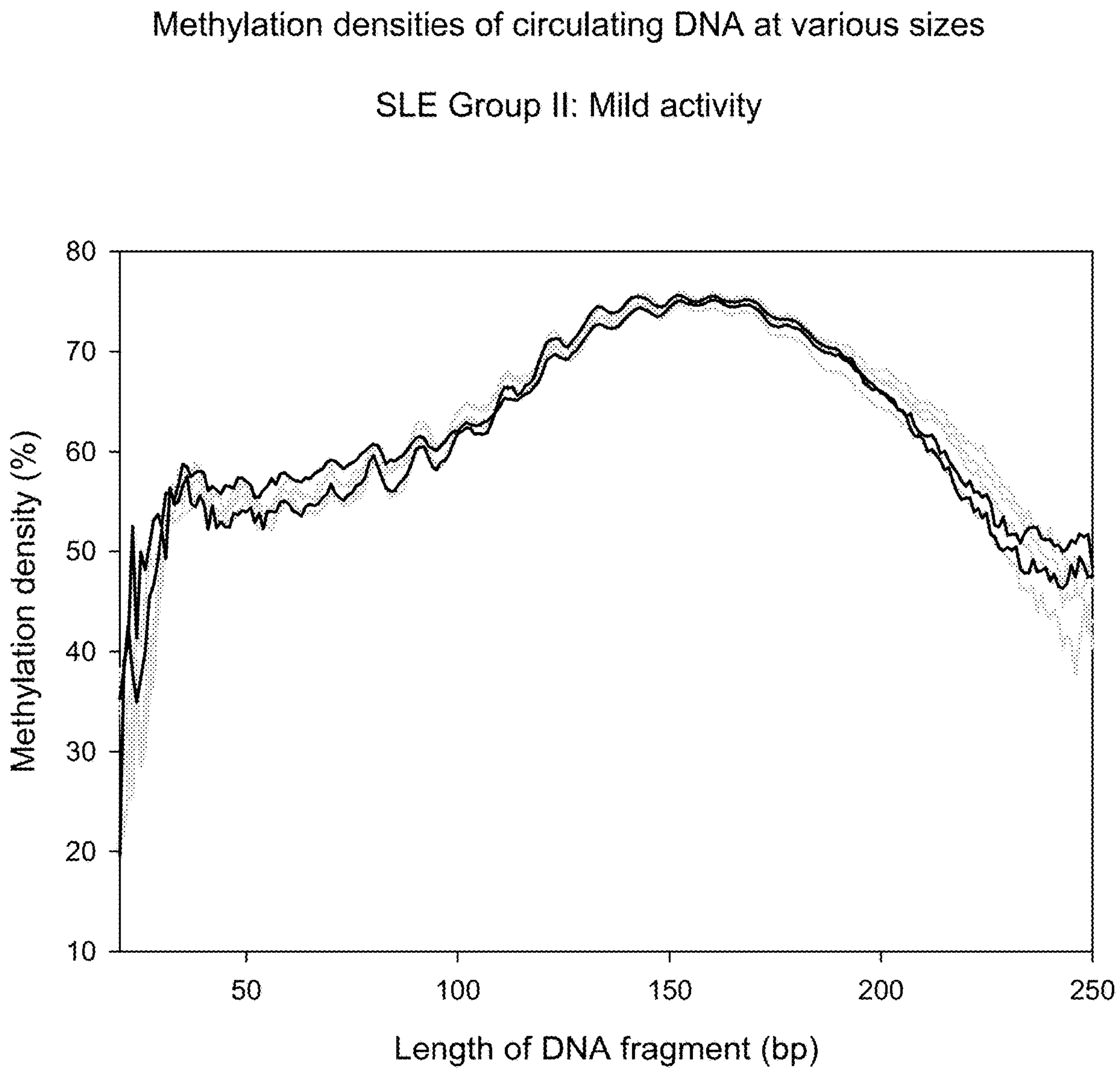
FIG. 24 shows the methylation densities of circulating DNA molecules, obtained from plasma samples of group II SLE patients, as a function of the sizes of those molecules.
Figure 25:
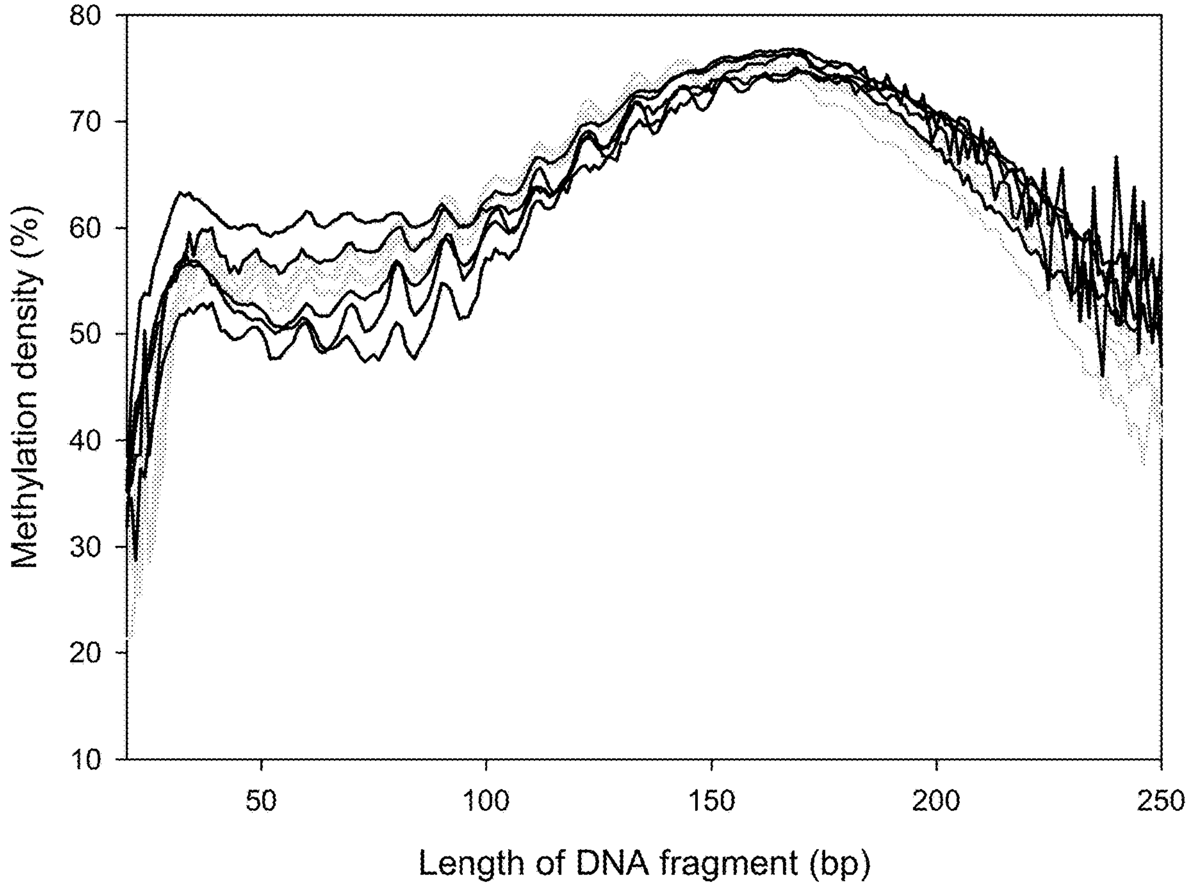
FIG. 25 shows the methylation densities of circulating DNA molecules, obtained from plasma samples of group III SLE patients, as a function of the sizes of those molecules.

As shown in FIGS. 23 and 24, we found that SLE patients with mild or no disease activity had a similar pattern of methylation densities at various sizes as the healthy individuals. However, the SLE patients with a higher disease activity exhibited abnormal methylation density-DNA size relationships as shown on FIG. 25. It indicated that methylation densities of the short DNA of active SLE patients were deranged.

These data suggest that there exists an association between the altered methylation and size profiles of plasma DNA of SLE patients. The plasma DNA profile characteristic of SLE patients may result from the relative increase in short hypomethylated DNA molecules in the plasma of those patients. Possibly, there is delayed clearance or degradation of the short unmethylated plasma DNA in SLE patients. These derangements appeared more marked in SLE patients with higher disease activities. The data also suggest that the assessments of the size and methylation profiles of DNA in plasma of SLE patients could be used synergistically for developing new tools for the diagnosis, prognostication and treatment monitoring of SLE.

Figure 26:
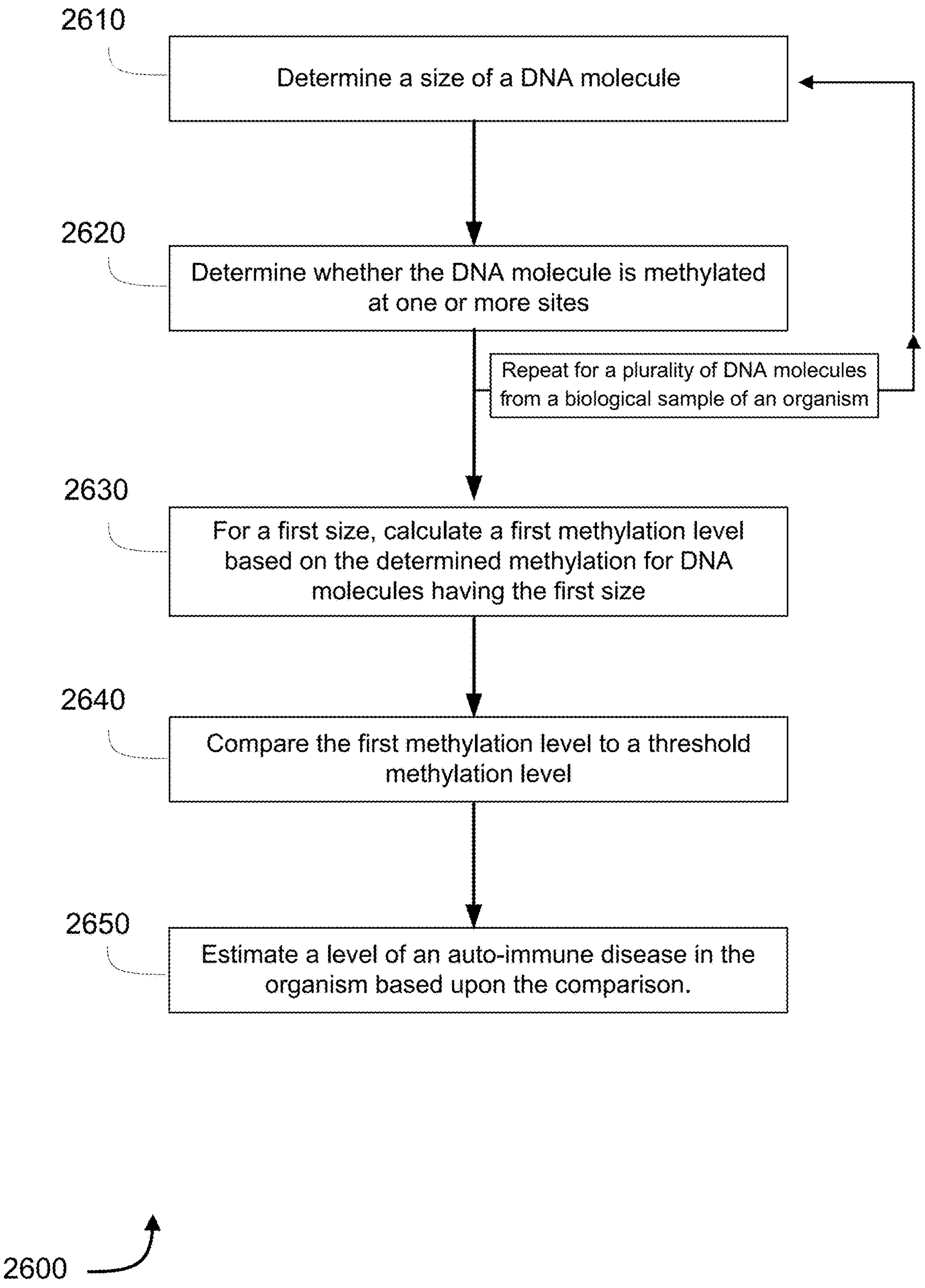
FIG. 26 shows a method 2600 for detecting an autoimmune disease in an organism, e.g. a human patient, based on the methylation levels of DNA molecules having one or more sizes, according to embodiments of the present invention.

Method 2600 (shown in FIG. 26) is provided for detecting an auto-immune disease in an organism, e.g. a human patient, based on the methylation levels of DNA molecules having one or more sizes. The method involves analyzing a biological sample of an organism, the biological sample including nucleic acid molecules, wherein at least some of the nucleic acid molecules are cell-free. The biological sample can be obtained from the organism and prepared for analysis as discussed above.

At blocks 2610 and 2620, a DNA molecule is analyzed. These blocks are repeated for each molecule analyzed of the plurality of molecules. Analyzing a DNA molecule includes determining a size of the DNA molecule, and determining whether the DNA molecule is methylated at one or more sites. The size and methylation status of each DNA molecule can be determined as desired, for example using massively parallel sequencing or single-molecule sequencing. In preferred embodiments, each molecule is analyzed using methylation-aware sequencing. If desired, data from the analysis of the DNA molecules can be filtered on the basis of the sequences of these molecules. For example, the sequences of individual DNA molecules can be aligned with a reference genome sequence, and the molecules can be queried for methylation (or lack of methylation) at selected sites in the reference genome sequence. These sites can correspond to coding regions, non-coding regions, repeat regions, non-repeat regions, or specific chromosomes or genes, for example. Thus, only data for molecules that include the selected sites are passed to subsequent steps of the method. Alternatively, methylation data can be obtained and further analyzed at all possible sites, or without regard to the sequences of the DNA molecules.

At block 2630, a first methylation level is calculated based on the determined methylation for DNA molecules having a first size. In some embodiments, the first methylation level is a methylation density. The first size can be selected as desired and can represent relatively short or long molecules, or molecules having sizes within a range. In some embodiments, the first size is a range of sizes having a minimum and maximum, and the maximum is 10, 20, 30, 40, 50, 60, 70, 80, 90, 100, 110, 120, 130, 140, or 150 bp. In some embodiments, the first size is a range of sizes having a minimum and maximum, and the difference between the minimum and maximum is 10, 20, 30, 40, 50, 60, 70, 80, 90, 100, 110, 120, 130, 140, or 150 bp. The first size can also be defined in terms of a cutoff value. For example, molecules having the first size can be shorter or longer than the cutoff value. The cutoff value can be, for example, 10, 20, 30, 40, 50, 60, 70, 80, 90, 100, 110, 120, 130, 140, or 150 bp.

At block 2640, the first methylation level is compared to a threshold methylation level. In some embodiments, the threshold methylation level is calculated using one or more control biological samples, e.g. samples obtained from organisms known or assumed to lack the auto-immune disease. The threshold methylation level can be calculated for DNA molecules from the control biological samples also having the first size, or a comparable size or range of sizes. In some embodiments, the threshold methylation level is a methylation density.

Comparing the first methylation level to the threshold methylation level can involve determining whether the first methylation level is greater than or less than the threshold methylation level, and by how much. For example, the comparison can involve calculating a difference in percent methylation densities. A first methylation level that exceeds the threshold methylation level can indicate hypermethylation, while a first methylation level that falls below the threshold methylation level can indicate hypomethylation. Instead or in addition, the comparison can involve calculating a ratio of the two quantities. The comparison can also include calculating a statistical measure, such as a confidence interval or uncertainty, to characterize the difference or ratio of the first methylation level and threshold methylation level.

At block 2650, a level of the auto-immune disease is estimated based on the comparison at block 2640. The first level can be a level of SLE or a patient grouping, for example, and can reflect agreement or disparity between the first methylation level and threshold methylation level. The first level can also reflect the magnitude of any observed hypermethylation or hypomethylation. Greater hypomethylation can indicate higher disease activity, particularly when the first size represents relatively short DNA molecules such as those less than 50, 60, 70, 80, 90, 100, 110, 120, 130, 140, or 150 bp in length. In some embodiments, the auto-immune disease is detected if the first methylation level is less than the threshold methylation level. The estimated level of the auto-immune disease can be used as appropriate, for example to design a treatment regimen for the organism or determine a dose of a medication.

Some embodiments of method 2600 also include designating a second size of DNA molecules and examining the methylation of these molecules. The second size is greater than the first size and represents longer DNA molecules. Like the first size, the second size can be a single size or range of sizes, and can be selected as desired. In some embodiments, when the first size and second size are both ranges of sizes, the ranges do not overlap, or the maximum of the range for the first size is the minimum of the range for the second size. In some embodiments, molecules having the first size can be shorter than a cutoff value, whereas molecules having the second size can be longer than the cutoff value. In some embodiments, the second size includes DNA molecules longer than about 50, 60, 70, 80, 90, 100, 110, 120, 130, 140, or 150 bp.

Once the second size is selected, a second methylation level can be calculated based on the determined methylation for DNA molecules having the second size. The second methylation level is preferably directly comparable to the first methylation level and is calculated in the same way or a similar way. In some embodiments, the second methylation level is a methylation density.

Estimating the level of the auto-immune disease in the organism can then be further based on a ratio of the first methylation level to the second methylation level. This ratio indicates the extent of methylation in smaller DNA molecules of the biological sample as compared with larger molecules. A ratio less than 1 indicates that the smaller molecules are less methylated than the larger molecules on average, and an unusually low or high ratio can indicate hypomethylation or hypermethylation of the smaller molecules. The ratio can be compared with a reference value, for example a ratio obtained from analysis of control biological samples, to determine whether the ratio is aberrant. The ratio can be incorporated into the estimation of the level of the auto-immune disease as desired.

IV. METHYLATION AND SIZE

Plasma DNA molecules are known to exist in circulation in the form of short molecules, with the majority of molecules about 160 bp in length[37,38]. Interestingly, our data revealed a relationship between the methylation status and the size of plasma DNA molecules. Thus, plasma DNA fragment length is linked to DNA methylation level. The characteristic size profiles of plasma DNA molecules suggest that the majority are associated with mononucleosomes, possibly derived from enzymatic degradation during apoptosis.

Circulating DNA is fragmented in nature. In particular, circulating fetal DNA is shorter than maternally-derived DNA in maternal plasma samples[39]. As paired-end alignment enables the size analysis of bisulfite-treated DNA, one could assess directly if any correlation exists between the size of plasma DNA molecules and their respective methylation levels. We explored this in the maternal plasma as well as a non-pregnant adult female control plasma sample.

Paired-end sequencing (which includes sequencing an entire molecule) for both ends of each DNA molecule was used to analyze each sample in this study. By aligning the pair of end sequences of each DNA molecule to the reference human genome and noting the genome coordinates of the extreme ends of the sequenced reads, one can determine the lengths of the sequenced DNA molecules. Plasma DNA molecules are naturally fragmented into small molecules and the sequencing libraries for plasma DNA are typically prepared without any fragmentation steps. Hence, the lengths deduced by the sequencing represented the sizes of the original plasma DNA molecules.

In a previous study, we determined the size profiles of the fetal and maternal DNA molecules in maternal plasma[37]. We showed that the plasma DNA molecules had sizes that resembled mononucleosomes and fetal DNA molecules were shorter than the maternal ones. In this study, we have determined the relationship of the methylation status of plasma DNA molecules to their sizes.

A. Estimating Methylation Based on Size

Accordingly, a size distribution can be used to estimate a total methylation percentage of a plasma sample. This methylation measurement can then be tracked during pregnancy, during monitoring of an auto-immune disease (e.g., SLE) or other disease (e.g., cancer), or during treatment by serial measurement of the size distributions of the plasma DNA. The methylation measurement can also be used to look for increased or decreased release of DNA from an organ or a tissue of interest. For example, one can specifically look for DNA methylation signatures specific to a specific organ (e.g. the liver) and to measure the concentrations of these signatures in plasma. As DNA is released into plasma when cells die, an increase in levels could mean an increase in cell death or damage in that particular organ or tissue. A decrease in level from a particular organ can mean that treatment to counter damage or pathological processes in that organ is under control.

Figure 27:
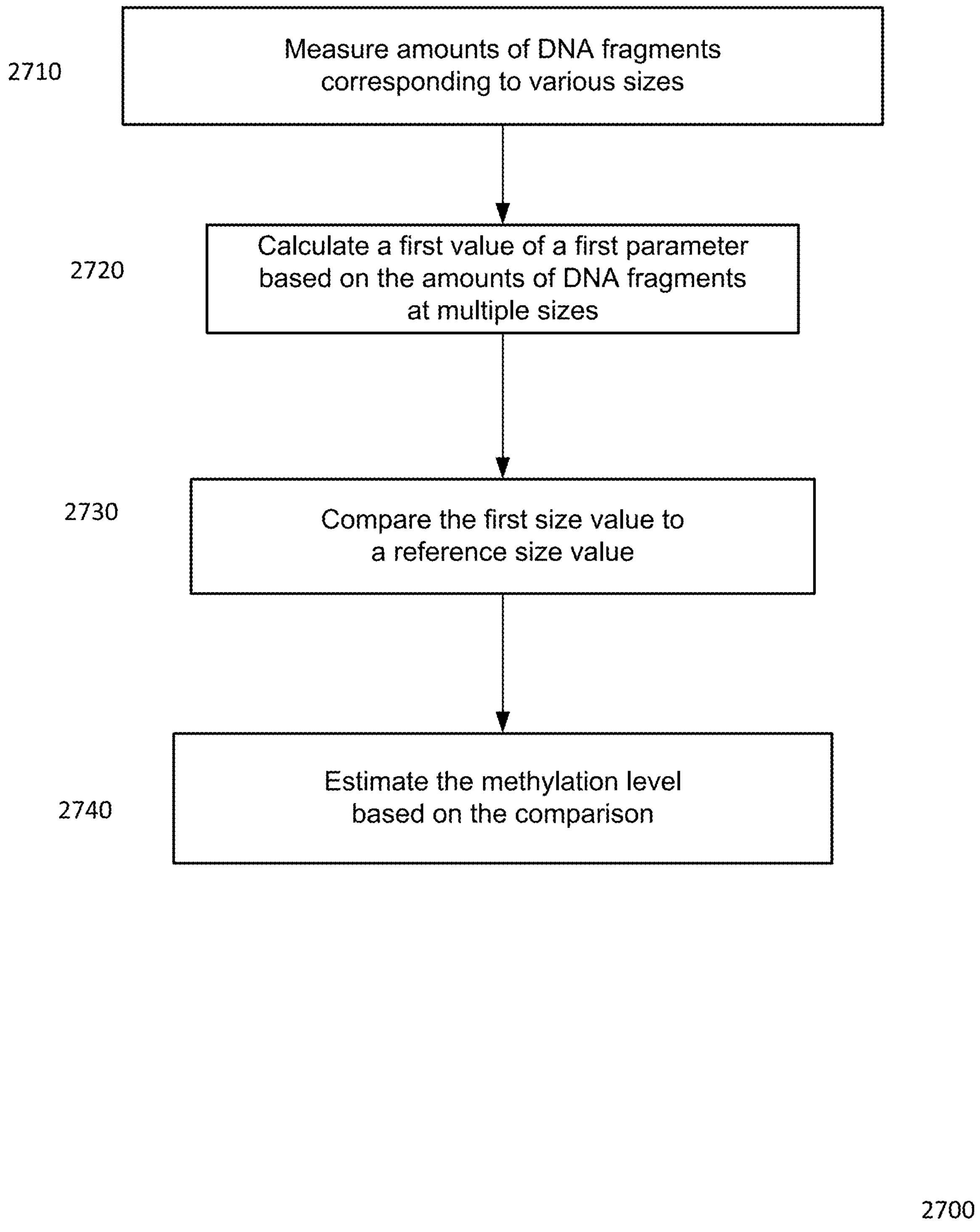
FIG. 27 shows a method 2700 for estimating a methylation level of DNA in a biological sample of an organism according to embodiments of the present invention.

A method 2700 is provided for estimating a methylation level of DNA in a biological sample of an organism according to embodiments of the present invention. Method 2700 is shown in FIG. 27. The methylation level can be estimated for a particular region of a genome or the entire genome. If a specific region is desired, then DNA fragments only from that specific region may be used.

At block 2710, amounts of DNA fragments corresponding to various sizes are measured. For each size of a plurality of sizes, an amount of a plurality of DNA fragments from the biological sample corresponding to the size can be measured. For instance, the number of DNA fragments having a length of 140 bases may be measured. The amounts may be saved as a histogram. In one embodiment, a size of each of the plurality of nucleic acids from the biological sample is measured, which may be done on an individual basis (e.g., by single molecule sequencing of a whole molecule or just ends of the molecule) or on a group basis (e.g., via electrophoresis). The sizes may correspond to a range. Thus, an amount can be for DNA fragments that have a size within a particular range. When paired-end sequencing is performed, the DNA fragments (as determined by the paired sequence reads) mapping (aligning) to a particular region may be used to determine the methylation level of the region.

At block 2720, a first value of a first parameter is calculated based on the amounts of DNA fragments at multiple sizes. In one aspect, the first parameter provides a statistical measure of a size profile (e.g., a histogram) of DNA fragments in the biological sample. The parameter may be referred to as a size parameter since it is determined from the sizes of the plurality of DNA fragments.

The first parameter can be of various forms. One parameter is the percentage of DNA fragment of a particular size or range of sizes relative to all DNA fragments or relative to DNA fragments of another size or range. Such a parameter is a number of DNA fragments at a particular size divided by the total number of fragments, which may be obtained from a histogram (any data structure providing absolute or relative counts of fragments at particular sizes). As another example, a parameter could be a number of fragments at a particular size or within a particular range divided by a number of fragments of another size or range. The division can act as a normalization to account for a different number of DNA fragments being analyzed for different samples. A normalization can be accomplished by analyzing a same number of DNA fragments for each sample, which effectively provides a same result as dividing by a total number fragments analyzed. Additional examples of parameters and about size analysis can be found in U.S. patent application Ser. No. 13/789,553, which is incorporated by reference for all purposes.

At block 2730, the first size value is compared to a reference size value. The reference size value can be calculated from DNA fragments of a reference sample. To determine the reference size values, the methylation profile can be calculated and quantified for a reference sample, as well as a value of the first size parameter. Thus, when the first size value is compared to the reference size value, a methylation level can be determined.

At block 2740, the methylation level is estimated based on the comparison. In one embodiment, one can determine if the first value of the first parameter is above or below the reference size value, and thereby determine if the methylation level of the instant sample is above or below the methylation level to the reference size value. In another embodiment, the comparison is accomplished by inputting the first value into a calibration function. The calibration function can effectively compare the first value to calibration values (a set of reference size values) by identifying the point on a curve corresponding to the first value. The estimated methylation level is then provided as the output value of the calibration function.

Accordingly, one can calibrate a size parameter to a methylation level. For example, a methylation level can be measured and associated with a particular size parameter for that sample. Then data points from various samples can be fit a calibration function. In one implementation, different calibration functions can be used for different subsets of DNA. Thus, there may be some form of calibration based on prior knowledge about the relationship between methylation and size for a particular subset of DNA. For example, the calibration for fetal and maternal DNA could be different.

As shown above, the placenta is more hypomethylated when compared with maternal blood, and thus the fetal DNA is smaller due to the lower methylation. Accordingly, an average size of the fragments of a sample (or other statistical value) can be used to estimate the methylation density. As the fragment sizes can be measured using paired-end sequencing, rather than the potentially technically more complex methylation-aware sequencing, this approach would potentially be cost-effective if used clinically. This approach can be used for monitoring the methylation changes associated with the progress of pregnancy, or with pregnancy-associated disorders such as preeclampsia, preterm labor and fetal disorders (such as those caused by chromosomal or genetic abnormalities or intrauterine growth retardation).

In another embodiment, this approach can be used for detecting and monitoring cancer or SLE. For example, with the successful treatment of cancer, the methylation profile in plasma or another bodily fluid as measured using this size-based approach would change towards that of healthy individuals without cancer. Conversely, in the event that the cancer is progressing, then the methylation profile in plasma or another bodily fluid would diverge from that of healthy individuals without cancer.

In summary, the hypomethylated molecules were shorter than the hypermethylated ones in plasma. The same trend was observed in both the fetal and maternal DNA molecules. Since DNA methylation is known to influence nucleosome packing, our data suggest that perhaps the hypomethylated DNA molecules were less densely packed with histones and were therefore more susceptible to enzymatic degradation. On the other hand, our data also showed that despite the fetal DNA being much more hypomethylated than the maternal reads, the size distribution of the fetal and maternal DNA does not separate from one another completely. Even for the same size category, the methylation level of fetal- and maternal-specific reads differ from one another. This observation suggests that the hypomethylated state of fetal DNA is not the only factor that accounted for its relative shortness with reference to the maternal DNA.

B. Normalizing Methylation Based on Size

As described above and by Lun et al.[40], the methylation density (e.g., of plasma DNA) is correlated with the size of the DNA fragments. Methylation densities for shorter plasma DNA fragments can be significantly lower than those for longer fragments. We propose that some non-cancer conditions (e.g., SLE) with abnormal fragmentation patterns of plasma DNA may exhibit an apparent hypomethylation of plasma DNA due to the presence of more abundant short plasma DNA fragments, which are less methylated. In other words, the size distribution of plasma DNA can be a confounding factor for the methylation density for plasma DNA.

In some embodiments, a measured methylation level can be normalized to reduce the confounding effect of size distribution on plasma DNA methylation analysis. For example, a size of DNA molecules at the plurality of sites can be measured. In various implementations, the measurement can provide a specific size (e.g., length) to a DNA molecule or simply determine that the size falls within a specific range, which can also correspond to a size. The normalized methylation level can then be compared to a cutoff value. There are several ways to perform the normalization to reduce the confounding effect of size distribution on plasma DNA methylation analysis.

In one embodiment, size fractionation of DNA (e.g., plasma DNA) can be performed. The size fractionation can ensure that DNA fragments of a similar size are used to determine the methylation level in a manner consistent with the cutoff value. As part of the size fractionation, DNA fragments having a first size (e.g., a first range of lengths) can be selected, where the first cutoff value corresponds to the first size. The normalization can be achieved by calculating the methylation level using only the selected DNA fragments.

The size fractionation can be achieved in various ways, e.g., either by physical separation of different sized DNA molecules (e.g. by electrophoresis or microfluidics-based technologies, or centrifugation-based technologies) or by in silico analysis. For in silico analysis, in one embodiment, one can perform paired-end massively parallel sequencing of the plasma DNA molecules. One can then deduce the size of the sequenced molecules by comparison with the location of each of two ends of a plasma DNA molecule to a reference human genome. Then, one can perform subsequent analysis by the selection of sequenced DNA molecules that match one or more size selection criteria (e.g., the criteria of the size being within a specified range). Thus, in one embodiment, the methylation density can be analyzed for fragments with a similar size (e.g., within a specified range). The cutoff value can be determined based on fragments within the same size range. For instance, methylation levels can be determined from samples that are known to have a disease (e.g., cancer or SLE) or not have the disease, and the cutoff values can be determined from these methylation levels.

In another embodiment, a functional relationship between methylation density and size of circulating DNA can be determined. The functional relationship can be defined by data point or coefficients of a function. The functional relationship can provide scaling values corresponding to respective sizes (e.g., shorter sizes can have corresponding increases to the methylation). In various implementations, the scaling value can be between 0 and 1 or greater than 1.

The normalization can be made based on an average size. For example, an average size corresponding to DNA molecules used to calculate the first methylation level can be computed, and the first methylation level can be multiplied by the corresponding scaling value (i.e., corresponding to the average size). As another example, the methylation density of each DNA molecule can be normalized according to the size of the DNA molecule and relationship between DNA size and methylation.

In another implementation, the normalization can be done on a per molecule basis. For example, a respective size of a DNA molecule at a particular site can be obtained (e.g., as described above), and a scaling value corresponding to the respective size can be identified from the functional relationship. For a non-normalized calculation, each molecule would be counted equally in determining a methylation index at the site. For the normalized calculation, the contribution of a molecule to the methylation index can be weighted by the scaling factor that corresponds to the size of the molecule.

In one embodiment, the results for the analyses with and without size fractionation can be compared to indicate if there is any confounding effect of size on the methylation results. Thus, in addition or instead of normalization, the calculation of a methylation level at a particular size can be used to determine whether there is a likelihood of a false positive when the percentage of bins above a cutoff value differs with and without size fractionation, or whether just a particular methylation level differs. For example, the presence of a significant difference between the results for samples with and without size fractionation can be used to indicate the possibility of a false-positive result due to an abnormal fragmentation pattern. The threshold for determining if the difference is significant can be established via the analysis of a cohort of disease patients and a cohort of control subjects.

V. METHYLATION VS. CNA

As mentioned above, methylation analysis approaches described herein can be used in combination with other methods that are based on the genetic changes of tumor-derived DNA in plasma. Examples of such methods include the analysis for cancer-associated chromosomal aberrations[41,42]. Aspects of copy number aberrations (CNA), also referred to herein as measured genomic representation (MGR), are described in U.S. U.S. patent application Ser. No. 13/308,473.

A. CNA

Copy number aberrations can be detected by counting DNA fragments that align to a particular part of the genome, normalizing the count, and comparing the count to a cutoff value. In various embodiments, the normalization can be performed by a count of DNA fragments aligned to another haplotype of the same part of the genome (relative haplotype dosage (RHDO)) or by a count of DNA fragments aligned to another part of the genome.

The RHDO method relies on using heterozygous loci. Embodiments described in this section can also be used for loci that are homozygous by comparing two regions and not two haplotypes of the same region, and thus are non-haplotype specific. In a relative chromosomal region dosage method, the number of fragments from one chromosomal region (e.g., as determined by counting the sequence reads aligned to that region) is compared to an expected value (which may be from a reference chromosome region or from the same region in another sample that is known to be healthy). In this manner, a fragment would be counted for a chromosomal region regardless of which haplotype the sequenced tag is from. Thus, sequence reads that contain no heterozygous loci could still be used. To perform the comparison, an embodiment can normalize the tag count before the comparison. Each region is defined by at least two loci (which are separated from each other), and fragments at these loci can be used to obtain a collective value about the region.

A normalized value for the sequenced reads (tags) for a particular region can be calculated by dividing the number of sequenced reads aligning to that region by the total number of sequenced reads alignable to the whole genome. This normalized tag count allows results from one sample to be compared to the results of another sample. For example, the normalized value can be the proportion (e.g., percentage or fraction) of sequenced reads expected to be from the particular region, as is stated above. In other embodiments, other methods for normalization are possible. For example, one can normalize by dividing the number of counts for one region by the number of counts for a reference region (in the case above, the reference region is just the whole genome). This normalized tag count can then be compared against a threshold value, which may be determined from one or more reference samples not exhibiting cancer, SLE, or another disease.

The normalized tag count of the tested case would then be compared with the normalized tag count of one or more reference subjects, e.g. those without cancer. In one embodiment, the comparison is made by calculating the z-score of the case for the particular chromosomal region. The z-score can be calculated using the following equation: z-score=(normalized tag count of the case−mean)/SD, where "mean" is the mean normalized tag count aligning to the particular chromosomal region for the reference samples; and SD is the standard deviation of the number of normalized tag count aligning to the particular region for the reference samples. Hence, the z-score is the number of standard deviation that the normalized tag count of a chromosomal region for the tested case is away from the mean normalized tag count for the same chromosomal region of the one or more reference subjects.

In the situation when the tested organism has cancer, the chromosomal regions that are amplified in the tumor tissues would be over-represented in the plasma DNA. This would result in a positive value of the z-score. On the other hand, chromosomal regions that are deleted in the tumor tissues would be under-represented in the plasma DNA. This would result in a negative value of the z-score. The magnitude of the z-score is determined by several factors.

One factor is the fractional concentration of tumor-derived DNA in the biological sample (e.g. plasma). The higher the fractional concentration of tumor-derived DNA in the sample (e.g. plasma), the larger the difference between the normalized tag count of the tested case and the reference cases would be. Hence, a larger magnitude of the z-score would result.

Another factor is the variation of the normalized tag count in the one or more reference cases. With the same degree of the over-representation of the chromosomal region in the biological sample (e.g. plasma) of the tested case, a smaller variation (i.e. a smaller standard deviation) of the normalized tag count in the reference group would result in a higher z-score. Similarly, with the same degree of under-representation of the chromosomal region in the biological sample (e.g. plasma) of the tested case, a smaller standard deviation of the normalized tag count in the reference group would result in a more negative z-score.

Another factor is the magnitude of chromosomal aberration in the tumor tissues. The magnitude of chromosomal aberration refers to the copy number changes for the particular chromosomal region (either gain or loss). The higher the copy number changes in the tumor tissues, the higher the degree of over- or under-representation of the particular chromosomal region in the plasma DNA. For example, the loss of both copies of the chromosome would result in greater under-representation of the chromosomal region in the plasma DNA than the loss of one of the two copies of the chromosome and, hence, resulted in a more negative z-score. Typically, there are multiple chromosomal aberrations in cancers. The chromosomal aberrations in each cancer can further vary by its nature (i.e. amplification or deletion), its degree (single or multiple copy gain or loss) and its extent (size of the aberration in terms of chromosomal length).

The precision of measuring the normalized tag count is affected by the number of molecules analyzed. We expect that 15,000, 60,000 and 240,000 molecules would need to be analyzed to detect chromosomal aberrations with one copy change (either gain or loss) when the fractional concentration is approximately 12.5%, 6.3% and 3.2% respectively. Further details of the tag counting for detection of cancer for different chromosomal regions is described in U.S. Patent Publication No. 2009/0029377 entitled "Diagnosing Fetal Chromosomal Aneuploidy Using Massively Parallel Genomic Sequencing" by Lo et al., the entire contents of which are herein incorporated by reference for all purposes.

Embodiments can also use size analysis, instead of the tag counting method. Size analysis may also be used, instead of a normalized tag count. The size analysis can use various parameters, as mentioned herein, and in U.S. patent application Ser. No. 12/940,992. For example, the Q or F values from above may be used. Such size values do not need a normalization by counts from other regions as these values do not scale with the number of reads. Techniques of the haplotype-specific methods, such as the RHDO method described above and in more detail in U.S. patent application Ser. No. 13/308,473, can be used for the non-specific methods as well. For example, techniques involving the depth and refinement of a region may be used. In some embodiments, a GC bias for a particular region can be taken into account when comparing two regions. Since the RHDO method uses the same region, such a correction is not needed.

Although certain cancers can typically present with aberrations in particular chromosomal regions, such cancers do not always exclusively present with aberrations in such regions. For example, additional chromosomal regions could show aberrations, and the location of such additional regions may be unknown. Furthermore, for auto-immune diseases such as SLE, aberrations may not consistently localize to particular chromosomal regions, or the pattern of localization may not be well established. Thus, when screening patients to identify early stages of cancer, SLE, or other diseases, one may want to detect aberrations throughout the genome. To address these situations, embodiments can analyze a plurality of regions in a systematic fashion to determine which regions show aberrations. The number of aberrations and their location (e.g. whether they are contiguous) can be used, for example, to confirm aberrations, identify a disease, determine a stage of the disease, provide a diagnosis of the disease (e.g. if the number is greater than a threshold value), and provide a prognosis based on the number and location of various regions exhibiting an aberration.

Accordingly, embodiments can identify whether an organism has cancer, SLE, or another disease based on the number of regions that show an aberration. Thus, one can test a plurality of regions (e.g., 3,000) to identify a number of regions that exhibit an aberration. The regions may cover the entire genome or just parts of the genome, e.g., non-repeat regions.

Figure 28:
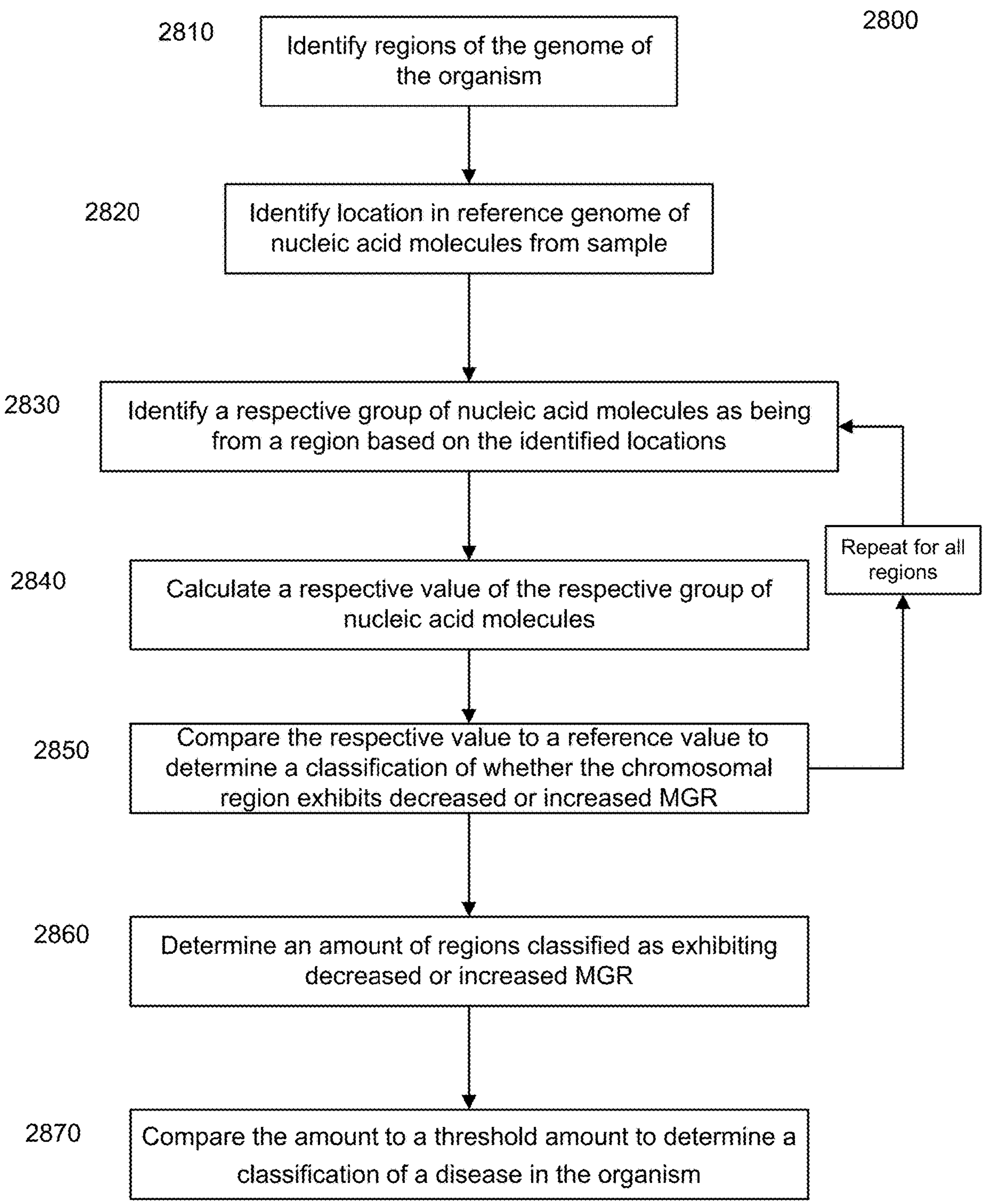
FIG. 28 shows a method 2800 of analyzing a biological sample of an organism using a plurality of chromosomal regions according to embodiments of the present invention.

A method 2800 is provided of analyzing a biological sample of an organism using a plurality of chromosomal regions (also called genomic regions herein) according to embodiments of the present invention. The biological sample includes nucleic acid molecules (also called fragments). Method 2800 is shown in FIG. 28.

At block 2810, a plurality of regions (e.g., non-overlapping regions) of the genome of the organism are identified. Each chromosomal region includes a plurality of loci. A region can be 1 Mb in size, or some other equal-size. For the situation of a region being 1 Mb in size, the entire genome can then include about 3,000 regions, each of predetermined size and location. Such predetermined regions can vary to accommodate a length of a particular chromosome or a specified number of regions to be used, and any other criteria mentioned herein. If regions have different lengths, such lengths can be used to normalize results, e.g., as described herein. The regions can be specifically selected based on certain criteria of the specific organism and/or based on knowledge of the disease being tested. The regions can also be arbitrarily selected.

The chromosomal regions need not be identified prior to obtaining and/or analyzing the biological sample. For example, the regions can be identified based on the locations determined for nucleic acid molecules of the sample, or the distribution of these locations, in a reference genome of the organism. Regions can be identified if their representation in the sample is abnormally high or low.

At block 2820, a location of the nucleic acid molecule in a reference genome of the organism is identified for each of a plurality of nucleic acid molecules. The location may be determined in any of the ways mentioned herein, e.g., by sequencing the fragments to obtain sequenced tags and aligning the sequenced tags to the reference genome. A particular haplotype of a molecule can also be determined for the haplotype-specific methods.

Blocks 2830-2850 are performed for each of the chromosomal regions. At block 2830, a respective group of nucleic acid molecules is identified as being from the chromosomal region based on the identified locations. The respective group can include at least one nucleic acid molecule located at each of the plurality of loci of the chromosomal region. In one embodiment, the group can be fragments that align to a particular haplotype of the chromosomal region, e.g., as in the RHDO method above. In another embodiment, the group can be of any fragment that aligns to the chromosomal region.

At block 2840, a computer system calculates a respective value of the respective group of nucleic acid molecules. The respective value defines a property of the nucleic acid molecules of the respective group. The respective value can be any of the values mentioned herein. For example, the value can be the number or percentage of fragments in the group or a statistical value of a size distribution of the fragments in the group. The respective value can also be a normalized value, e.g., a tag count of the region divided by the total number of tag counts for the sample or the number of tag counts for a reference region. The respective value can also be a difference or ratio from another value (e.g., in RHDO), thereby providing the property of a difference for the region.

At block 2850, the respective value is compared to a reference value to determine a classification of whether the first chromosomal region exhibits a decreased or increased measured genomic representation. A decreased measured genomic representation can correspond to a deletion in the genomic DNA of one or more cells, wherein these cells make up a portion of the cells in the organism from which the biological sample was obtained. Similarly, an increased measured genomic representation can correspond to an amplification in the genomic DNA of one or more cells. The reference value can be any threshold or reference value described herein. For example, the reference value could be a statistical (e.g., mean) or threshold value determined for one or more normal samples. For RHDO, the respective value could be the difference or ratio of tag counts for the two haplotypes, and the reference value can be a threshold for determining that a statistically significant deviation exists. As another example, the reference value could be the tag count or size value for another haplotype or region, and the comparison can include taking a difference or ratio (or function of such) and then determining if the difference or ratio is greater than a threshold value.

The reference value can vary based on the results of other regions. For example, if neighboring regions also show a deviation (although small compared to one threshold, e.g., a z-score of 3), then a lower threshold can be used. For example, if three consecutive regions are all above a first threshold, then a disease may be more likely. Thus, this first threshold may be lower than another threshold that is required to identify the disease from non-consecutive regions. Having three regions (or more than three) having even a small deviation can have a low enough probability of a chance effect that the sensitivity and specificity can be preserved.

At block 2860, an amount of genomic regions classified as exhibiting a decreased or increased measured genomic representation is determined. The chromosomal regions that are counted can have restrictions. For example, only regions that are contiguous with at least one other region may be counted (or contiguous regions can be required to be of a certain size, e.g., 4 or more regions). For embodiments where the regions are not equal, the number can also account for the respective lengths (e.g., the number could be a total length of the aberrant regions).

At block 2870, the amount is compared to a threshold amount to determine a classification of the sample. As examples, the classification can be whether the organism has SLE, a level of SLE, and a prognosis of SLE. In one embodiment, all aberrant regions are counted and a single threshold value is used regardless of where the regions appear. In another embodiment, a threshold value can vary based on the locations and size of the regions that are counted. For example, the amount of regions on a particular chromosome or arm of a chromosome may be compared to a threshold for that particular chromosome (or arm). Multiple thresholds may be used. For instance, the amount of aberrant regions on a particular chromosome (or arm) must be greater than a first threshold value, and the total amount of aberrant regions in the genome must be greater than a second threshold value. The threshold value can be a percentage of the regions that are determined to exhibit a deletion or an amplification.

This threshold value for the amount of regions can also depend on how strong the imbalance is for the regions counted. For example, the amount of regions that are used as the threshold for determining a classification of cancer or SLE can depend on the specificity and sensitivity (aberrant threshold) used to detect an aberration in each region. For example, if the aberrant threshold is low (e.g. z-score of 2), then the amount threshold may be selected to be high (e.g., 150). But, if the aberrant threshold is high (e.g., a z-score of 3), then the amount threshold may be lower (e.g., 50). The amount of regions showing an aberration can also be a weighted value, e.g., one region that shows a high imbalance can be weighted higher than a region that just shows a little imbalance (i.e. there are more classifications than just positive and negative for the aberration). As an example, a sum of z-scores can be used, thereby using the weighted values.

Accordingly, the amount (which may include number and/or size) of chromosomal regions showing significant over- or under-representation of a normalized tag count (or other respective value for the property of the group) can be used for reflecting the severity of disease. For cancer, the amount of chromosomal regions with an aberrant normalized tag count can be determined by two factors, namely the number (or size) of chromosomal aberrations in the tumor tissues and the fractional concentration of tumor-derived DNA in the biological sample (e.g. plasma). More advanced cancers tend to exhibit more (and larger) chromosomal aberrations. Hence, more cancer-associated chromosomal aberrations would potentially be detectable in the sample (e.g. plasma). In patients with more advanced cancer, the higher tumor load would lead to a higher fractional concentration of tumor-derived DNA in the plasma. As a result, the tumor-associated chromosomal aberrations would be more easily detected in the plasma sample.

One possible approach for improving the sensitivity without sacrificing the specificity is to take into account the result of the adjacent chromosomal segment. In one embodiment, the cutoff for the z-score remains to be >2 and <−2. However, a chromosomal region would be classified as potentially aberrant only when two consecutive segments would show the same type of aberrations, e.g. both segments have a z-score of >2. In other embodiments, the z-score of neighboring segments can be added together using a higher cutoff value. For example, the z-scores of three consecutive segments can be summed and a cutoff value of 5 can be used. This concept can be extended to more than three consecutive segments.

The combination of amount and aberrant thresholds can also depend on the purpose of the analysis, and any prior knowledge of the organism (or lack thereof). For example, if screening a normal healthy population for cancer, then one would typically use high specificity, potentially in both the amount of regions (i.e. high threshold for the number of regions) and an aberrant threshold for when a region is identified as having an aberration. But, in a patient with higher risk (e.g. a patient complaining of a lump or family history, smoker, chronic human papillomavirus (HPV) carrier, hepatitis virus carrier, or other virus carrier) then the thresholds could be lower in order to have more sensitivity (less false negatives).

In one embodiment, if one uses a 1-Mb resolution and a lower detection limit of 6.3% of tumor-derived DNA for detecting a chromosomal aberration, the number of molecules in each 1-Mb segment would need to be 60,000. This would be translated to approximately 180 million (60,000 reads/Mb×3,000 Mb) alignable reads for the whole genome.

A smaller segment size would give a higher resolution for detecting smaller chromosomal aberrations. However, this would increase the requirement of the number of molecules to be analyzed in total. A larger segment size would reduce the number of molecules required for the analysis at the expense of resolution. Therefore, only larger aberrations can be detected. In one implementation, larger regions could be used, segments showing an aberration could be subdivided and these subregions analyzed to obtain better resolution (e.g., as is described above). If one has an estimate for a size of deletion or amplification to be detected (or minimum concentration to detect), the number of molecules to analyze can be determined.

CNA and methylation can be used to determine respective classifications for a level of cancer or SLE, where the classifications are combined to provide a third classification. Besides such a combination, CNA can be used to change cutoff values for the methylation analysis and to identify false-positives by comparing methylation levels for groups of regions having different CNA characteristics. For instance, the methylation level for over-abundance (e.g., $Z_{CNA}>3$) can be compared to methylation level for normal abundance (e.g., $-3<Z_{CNA}<3$). First, the impact of CNA on methylation levels is described.

B. Alteration in Methylation Density at Regions With Chromosomal Gains and Losses As tumor tissues generally show an overall hypomethylation, the presence of tumor-derived DNA in the plasma of cancer patients would lead to the reduction in the methylation density when compared with non-cancer subjects. The degree of hypomethylation in the plasma of cancer patients is theoretically proportional to the fractional concentration of tumor-derived DNA in the plasma sample. In contrast, the degree of hypomethylation in the plasma of an SLE patient is not necessarily proportional to the concentration of DNA derived from a particular organ or tissue type, and can be related to (or confounded by) an abnormal distribution of sizes of DNA molecules.

For regions showing a chromosomal gain in the tumor tissues, an additional dosage of tumor DNA would be released from the amplified DNA segments into the plasma. This increased contribution of tumoral DNA to the plasma would theoretically lead to a higher degree of hypomethylation in the plasma DNA for the affected region. An additional factor is that genomic regions showing amplification would be expected to confer growth advantage to the tumor cells, and thus would be expected to be expressed. Such regions are generally hypomethylated.

In contrast, for regions that show chromosomal loss in the tumor tissue, the reduced contribution of tumoral DNA to plasma would lead to a lower degree of hypomethylation compared with regions with no copy number change. An additional factor is that genomic regions that are deleted in tumor cells might contain tumor suppressor genes and it might be advantageous to tumor cells to have such regions silenced. Thus, such regions are expected to have a higher chance of being hypermethylated.

Figure 29A:
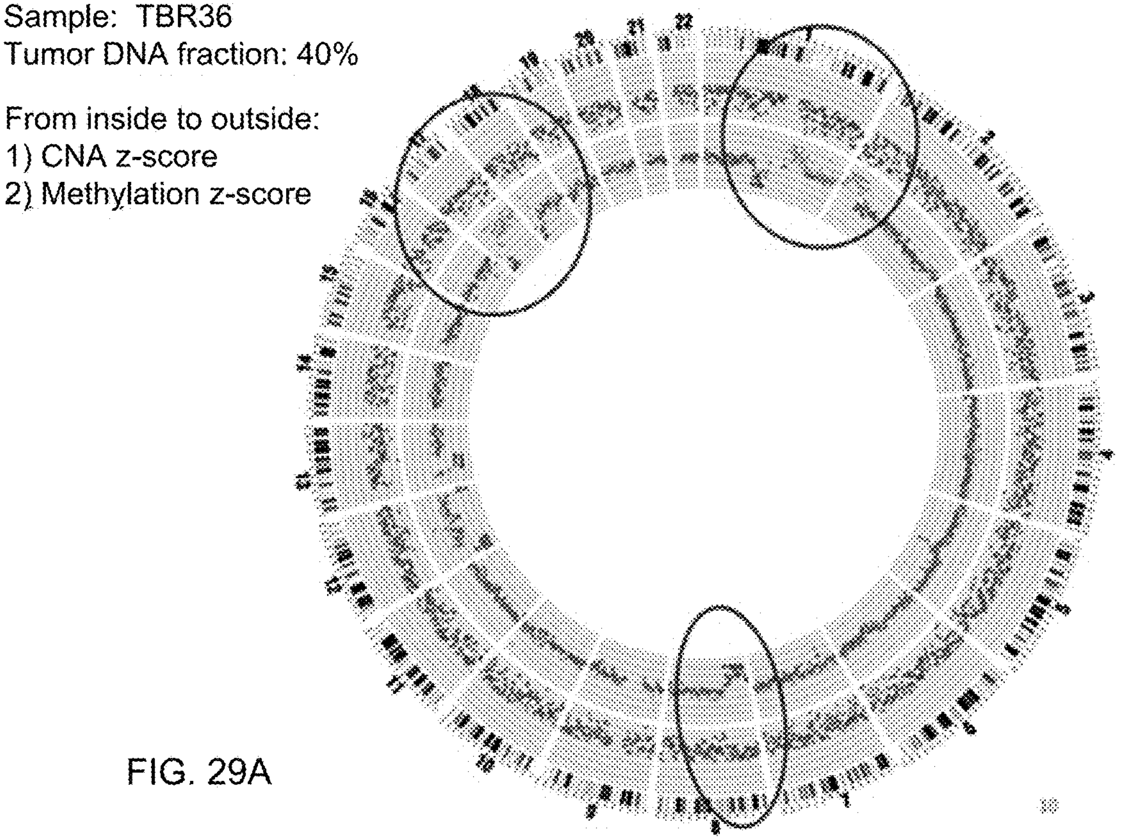
FIG. 29A shows Circos plots demonstrating the CNA (inner ring) and methylation changes (outer ring) in the bisulfate-treated plasma DNA for HCC patient TBR36.
Figure 29B:
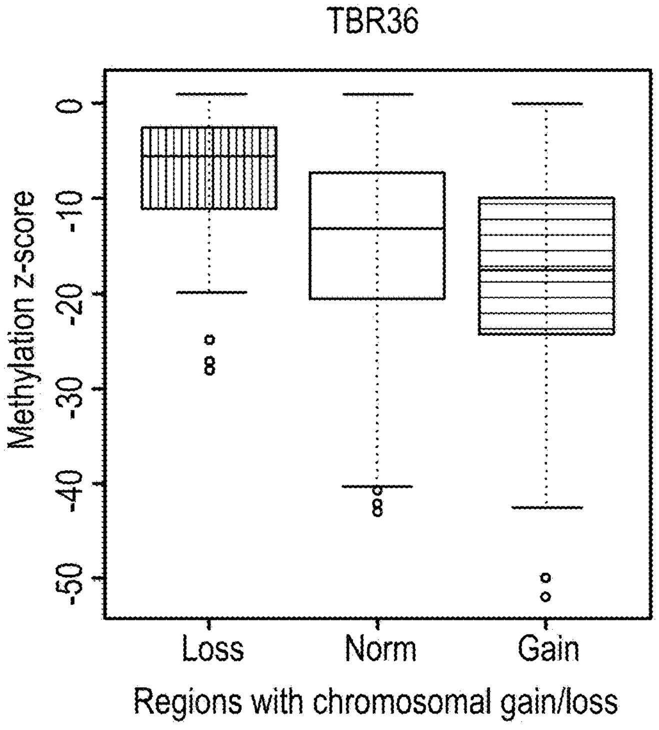
FIG. 29B is a plot of methylation z-scores for regions with chromosomal gains and loss, and regions without copy number change for the HCC patient TBR36.

Here, we use the results of two HCC patients (TBR34 and TBR36) to illustrate this effect. FIGS. 29A (TBR36) and 30A (TBR34) have circles highlighting regions with chromosomal gains or losses and the corresponding methylation analysis. FIGS. 29B and 30B show plots of methylation z-scores for losses, normal, and gains for patients TBR36 and TBR34, respectively.

FIG. 29A shows Circos plots demonstrating the CNA (inner ring) and methylation changes (outer ring) in the bisulfate-treated plasma DNA for HCC patient TBR36. The red circles highlight the regions with chromosomal gains or losses. Regions showing chromosomal gains were more hypomethylated than regions without copy number changes. Regions showing chromosomal losses were less hypomethylated than regions without copy number changes. FIG. 29B is a plot of methylation z-scores for regions with chromosomal gains and loss, and regions without copy number change for the HCC patient TBR36. Compared with regions without copy changes, regions with chromosomal gains had more negative z-scores (more hypomethylation) and regions with chromosomal losses had less negative z-scores (less hypomethylated).

Figure 30A:
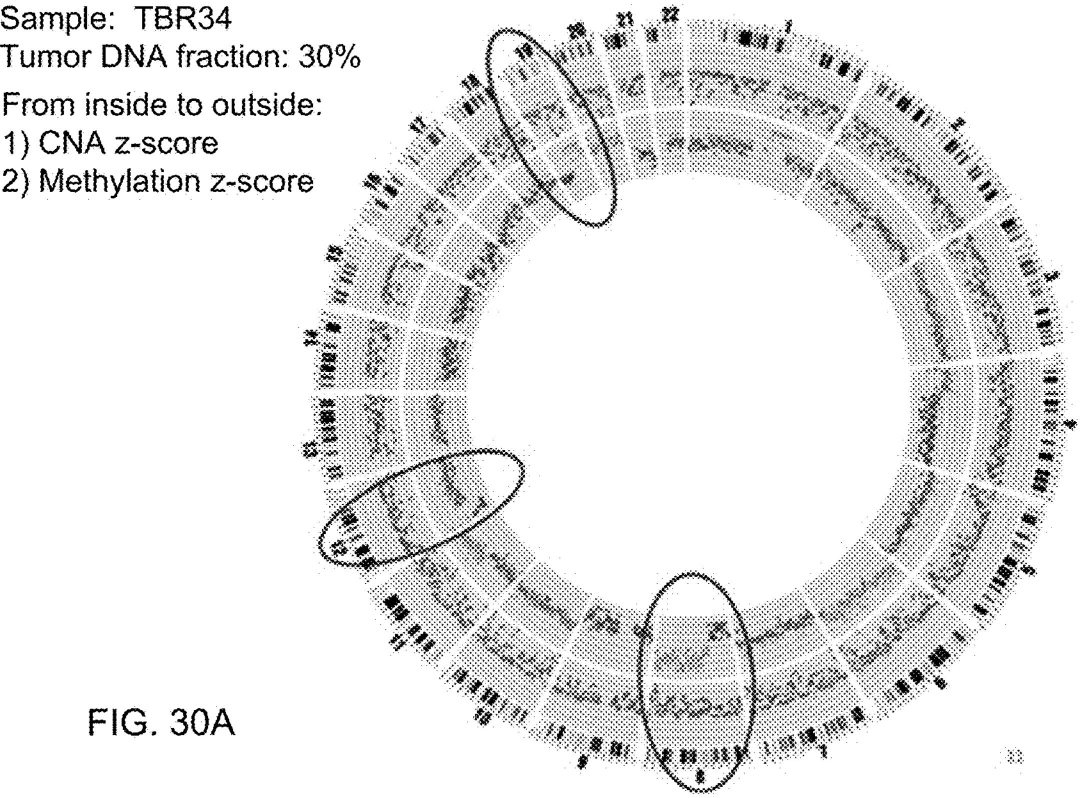
FIG. 30A shows Circos plots demonstrating the CNA (inner ring) and methylation changes (outer ring) in the bisulfate-treated plasma DNA for HCC patient TBR34.
Figure 30B:
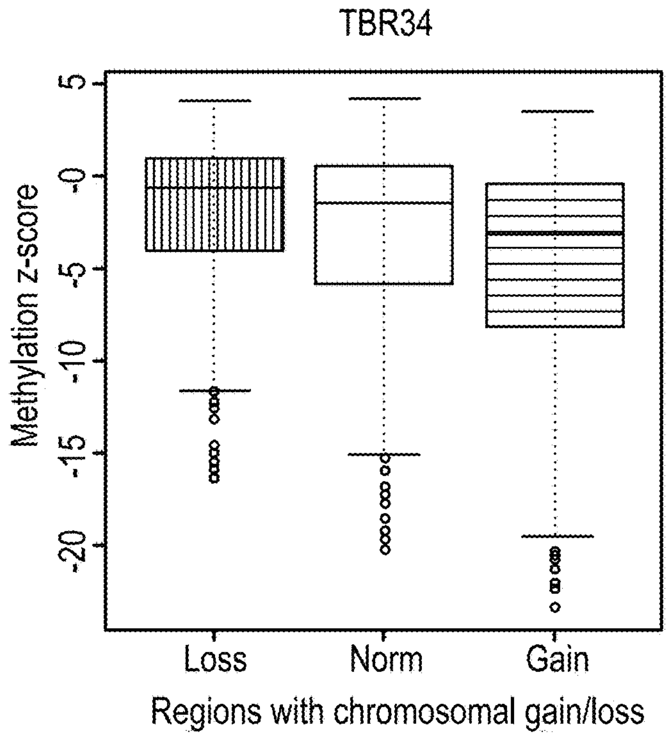
FIG. 30B is a plot of methylation z-scores for regions with chromosomal gains and loss, and regions without copy number change for the HCC patient TBR34.

FIG. 30A shows Circos plots demonstrating the CNA (inner ring) and methylation changes (outer ring) in the bisulfate-treated plasma DNA for HCC patient TBR34. FIG. 30B is a plot of methylation z-scores for regions with chromosomal gains and loss, and regions without copy number change for the HCC patient TBR34. The difference in methylation densities between regions with chromosomal gains and losses was larger in patient TBR36 than in patient TBR34 because the fractional concentration of tumor-derived DNA in the former patient was higher.

In this example, the regions used to determine CNA are the same as the regions used to determine methylation. In one embodiment, the respective region cutoff values are dependent on whether the respective region exhibits a deletion or an amplification. In one implementation, a respective region cutoff value (e.g., the z-score cutoff used to determine hypomethylation) has a larger magnitude when the respective region exhibits an amplification than when no amplification is exhibited (e.g., the magnitude could be greater than 3, and a cutoff of less than −3 can be used). Thus, for testing hypomethylation, a respective region cutoff value can have a larger negative value when the respective region exhibits an amplification than when no amplification is exhibited. Such an implementation is expected to improve the specificity of the test for detecting cancer.

In another implementation, a respective region cutoff value has a smaller magnitude (e.g., less than 3) than when the respective region exhibits a deletion than when no deletion is exhibited. Thus, for testing hypomethylation, a respective region cutoff value can have a less negative value when the respective region exhibits a deletion than when no deletion is exhibited. Such an implementation is expected to improve the sensitivity of the test for detecting cancer. The adjustment of the cutoff values in the above implementations can be changed depending on the desired sensitivity and specificity for a particularly diagnostic scenario. In other embodiments, the methylation and CNA measurements can be used in conjunction with other clinical parameters (e.g. imaging results or serum biochemistry) for prediction of cancer.

C. Using CNA to Select Regions

As described above, we have shown that the plasma methylation density would be altered in regions having copy number aberrations in the tumor tissues. At regions with copy number gain in the tumor tissue, increased contribution of hypomethylated tumoral DNA to the plasma would lead to a larger degree of hypomethylation of plasma DNA compared with regions without a copy number aberration. Conversely, at regions with copy number loss in the tumor tissue, the reduced contribution of hypomethylated cancer-derived DNA to the plasma would lead to a lesser degree of hypomethylation of plasma DNA. This relationship between the methylation density of plasma DNA and the relative representation can potentially be used for differentiating hypomethylation results associated with the presence of cancer-associated DNA and other non-cancerous causes (e.g., SLE) of hypomethylation in plasma DNA. A dependence of methylation density on copy number aberration (e.g., plasma DNA molecules that originate from regions with copy number gain tend to be less methylated than other plasma DNA molecules) can indicate cancer, while weak or no dependence can indicate SLE. For example, if the difference (or ratio) between methylation levels of two groups of regions having different CNA exceeds a cutoff, then cancer can be identified. If the difference (or ratio) between methylation levels of two groups of regions having different CNA does not exceed a cutoff, then SLE (or another auto-immune disease) can be identified. An initial step of determining that an aberration in methylation levels exists can be performed.

To illustrate this approach, we analyzed the plasma samples of two hepatocellular carcinoma (HCC) patients and two patients with SLE without a cancer. These two SLE patients (SLE04 and SLE10) showed the apparent presence of hypomethylation and CNAs in plasma. For patient SLE04, 84% bins showed hypomethylation and 11.2% bins showed CNA. For patient SLE10, 10.3% bins showed hypomethylation and 5.7% bins showed CNA.

Figure 31A:
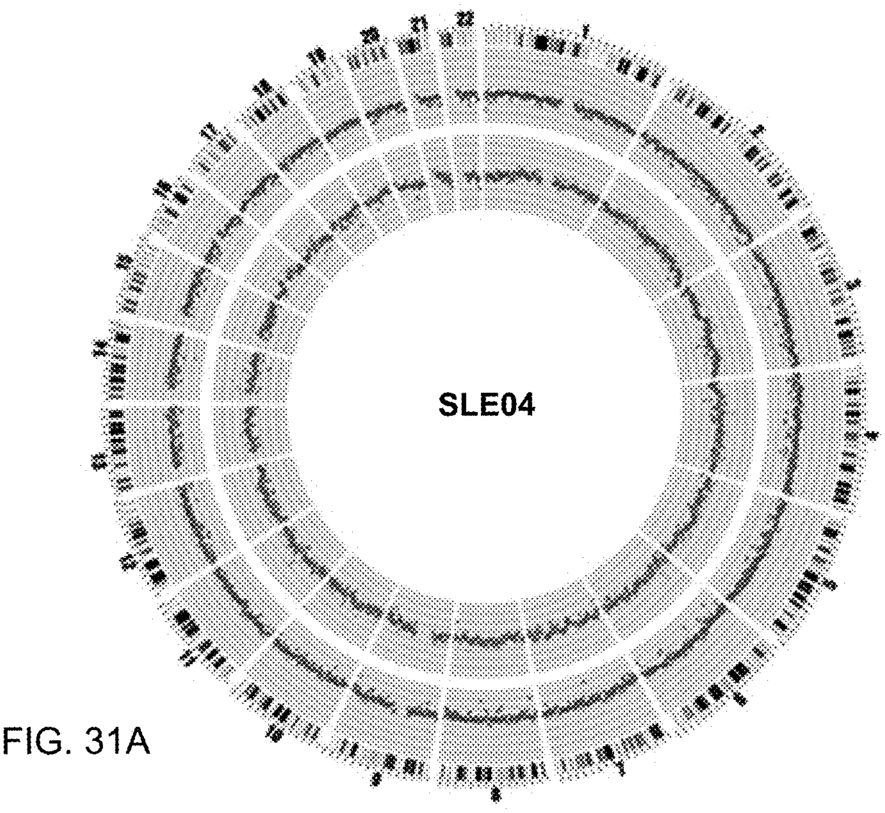
FIGS. 31A and 31B show results of plasma hypomethylation and CNA analysis for SLE patients SLE04 and SLE10.
Figure 31B:
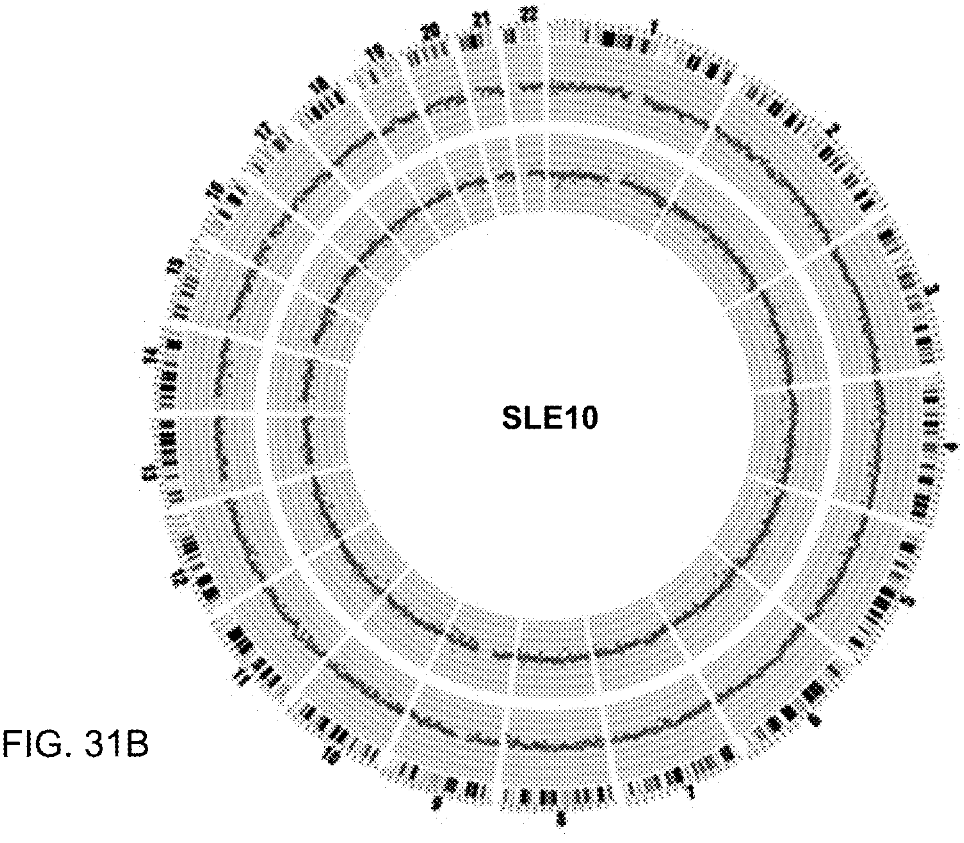

FIGS. 31A and 31B show results of plasma hypomethylation and CNA analysis for SLE patients SLE04 and SLE10. The outer circle shows the methylation z-scores ($Z_{meth}$) at 1 Mb resolution. The bins with methylation $Z_{meth}<-3$ were in red and those with $Z_{meth}>-3$ were in grey. The inner circle shows the CNA z-scores ($Z_{CNA}$). The green, red and grey dots represent bins with $Z_{CNA}>3$, <3 and between −3 to 3, respectively. In these two SLE patients, hypomethylation and CNA changes were observed in plasma.

To determine if the changes in methylation and CNA were consistent with the presence of cancer-derived DNA in plasma, we compared the $Z_{meth}$ for regions with $Z_{CNA}>3$, <−3 and between −3 to 3. For methylation changes and CNA contributed by cancer-derived DNA in plasma, regions with $Z_{CNA}<-3$ would be expected to be less hypomethylated and had less negative $Z_{meth}$. In contrast, regions with $Z_{CNA}>3$ would be expected to be more hypomethylated and had more negative $Z_{meth}$. For illustration purpose, we applied one-sided rank sum test to compare the $Z_{meth}$ for regions with CNA (i.e. regions with $Z_{CNA}<-3$ or >3) with regions without CNA (i.e. regions with $Z_{CNA}$ between −3 and 3). In other embodiments, other statistical tests, for example but not limited to Student's t-test, analysis of variance (ANOVA) test and Kruskal-Wallis test can be used.

Figure 32A:
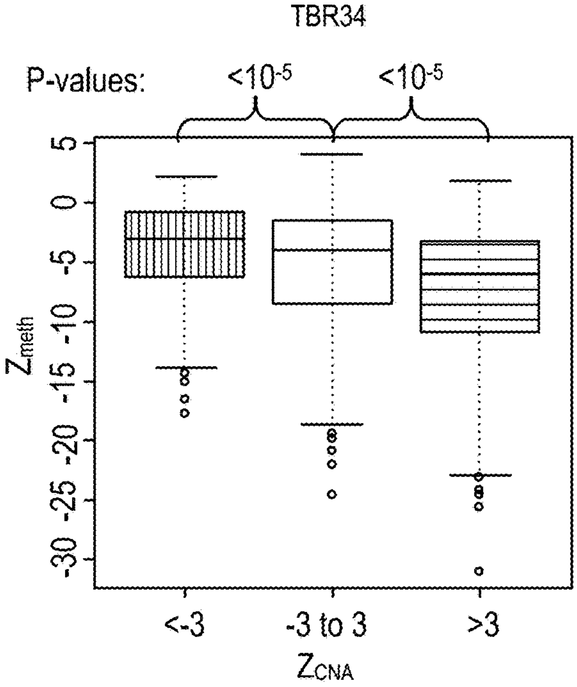
FIGS. 32A and 32B show $Z_{meth}$ analysis for regions with and without CNA for the plasma of two HCC patients (TBR34 and TBR36).
Figure 32B:
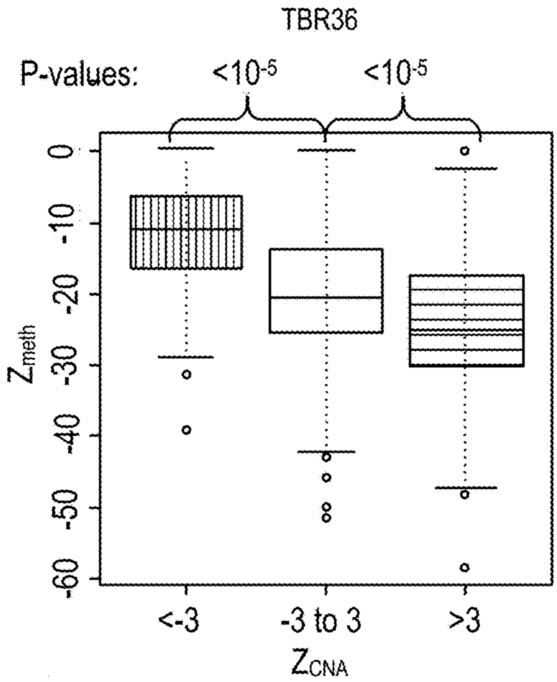

FIGS. 32A and 32B show $Z_{meth}$ analysis for regions with and without CNA for the plasma of two HCC patients (TBR34 and TBR36). Regions with $Z_{CNA}<-3$ and >3 represent regions with under- and over-representation in plasma, respectively. In both TBR34 and TBR36, regions that were under-represented in plasma (i.e. regions with $Z_{CNA}<-3$) had significantly higher $Z_{meth}$ (P-value $<10^{-5}$, one-sided rank sum test) than regions with normal representation in plasma (i.e. regions with $Z_{CNA}$ between −3 and 3). A normal representation correspond to that expected for a euploid genome. For regions with over-representation in plasma (i.e. regions with $Z_{CNA}>3$), they had significantly lower $Z_{meth}$ than regions with normal representation in plasma (P-value $<10^{-5}$, one-sided rank sum test). All these changes were consistent with the presence of hypomethylated tumoral DNA in the plasma samples.

Figure 32C:
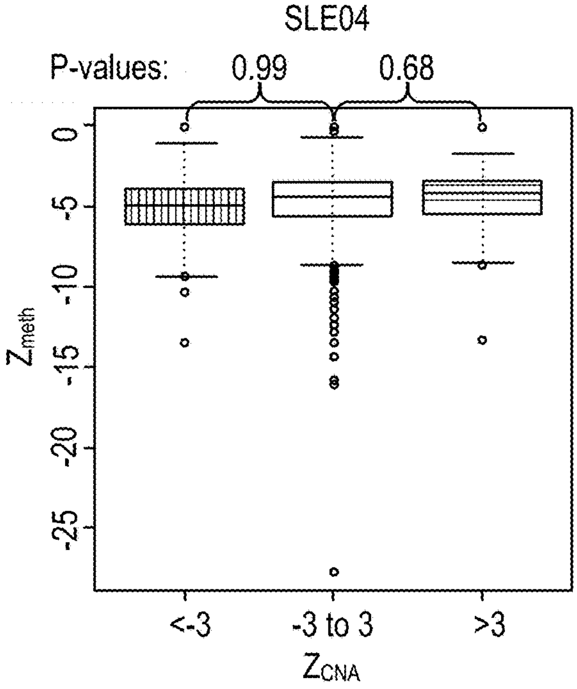
FIGS. 32C and 32D show $Z_{meth}$ analysis for regions with and without CNA for the plasma of two SLE patients (SLE04 and SLE10).
Figure 32D:
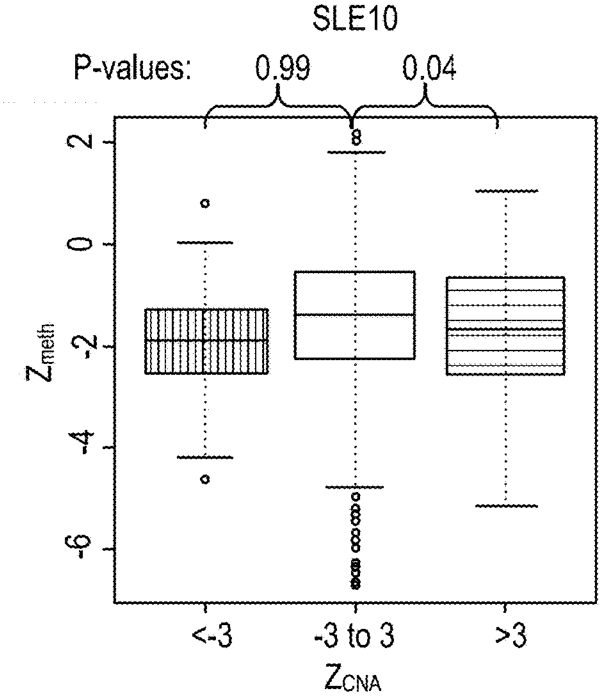

FIGS. 32C and 32D show $Z_{meth}$ analysis for regions with and without CNA for the plasma of two SLE patients (SLE04 and SLE10). Regions with $Z_{CNA}<-3$ and >3 represent regions with under- and over-representation in plasma, respectively. For SLE04, regions that were under-represented in plasma (i.e. regions with $Z_{CNA}<-3$) did not have significantly higher $Z_{meth}$ (P-value=0.99, one-sided rank sum test) than regions with normal representation in plasma (i.e. regions with $Z_{CNA}$ between −3 and 3) and regions with over-representation in plasma (i.e. regions with $Z_{CNA}>3$) did not have significantly lower $Z_{meth}$ than regions with normal representation in plasma (P-value=0.68, one-sided rank sum test). These results were different from the expected changes due to the presence of tumor-derived hypomethylated DNA in plasma. Similarly, for SLE10, regions with $Z_{CNA}<-3$ did not have significantly higher $Z_{meth}$ than regions with $Z_{CNA}$ between −3 and 3 (P-value=0.99, one-sided rank sum test).

A reason of not having the typical cancer-associated pattern between $Z_{meth}$ and $Z_{CNA}$ in the SLE patients is that, in the SLE patients, the CNA is not present in a specific cell type that also exhibits hypomethylation. Instead, the observed apparent presence of CNA and hypomethylation is due to the altered size distribution of circulating DNA in SLE patients. The altered size distribution could potentially alter the sequenced read densities for different genomic regions leading to apparent CNAs as the references were derived from healthy subjects. As described in the previous sections, there is a correlation between the size of a circulating DNA fragment and its methylation density. Therefore, the altered size distribution can also lead to an aberrant methylation.

Although the regions with $Z_{CNA}>3$ had slightly lower methylation levels than regions with $Z_{CNA}$ between −3 and 3, the p-value for the comparison was far higher than those observed in two cancer patients. In one embodiment, the p-value can be used as a parameter to determine the likelihood of a tested case for having a cancer. In another embodiment, the difference in $Z_{meth}$ between regions with normal and aberrant representation can be used as a parameter for indicating the likelihood of the presence of cancer. In one embodiment, a group of cancer patients can be used to establish the correlation between $Z_{meth}$ and $Z_{CNA}$ and to determine the thresholds for different parameters so as to indicate the changes are consistent with the presence of cancer-derived hypomethylated DNA in the tested plasma sample.

Accordingly, in one embodiment, a CNA analysis can be performed to determine a first set of regions that all exhibit one of: a deletion, an amplification, or normal representation. For example, the first set of regions can all exhibit a deletion, or all exhibit an amplification, or all exhibit a normal representation (e.g., have a normal first amount of regions, such as a normal $Z_{meth}$). A methylation level can be determined for this first set of regions (e.g., the first methylation level of method 2800 can correspond to the first set of regions).

The CNA analysis can determine a second set of regions that all exhibit a second of: a deletion, an amplification, or normal representation. The second set of regions would exhibit differently than the first set. For example, if the first set of regions were normal, then the second set of regions can exhibit a deletion or an amplification. A second methylation level can be calculated based on the respective numbers of DNA molecules methylated at sites in the second set of regions.

A parameter can then be computed between the first methylation level and the second methylation. For example, a difference or ratio can be computed and compared to a cutoff value. The difference or ratio can also be subjected to a probability distribution (e.g., as part of a statistical test) to determine the probability of obtaining the value, and this probability can be compared to a cutoff value to determine a level of cancer based on methylation levels. Such a cutoff can be chosen to differentiate samples having cancer and those not having cancer (e.g., SLE).

In one embodiment, a methylation level can be determined for the first set of region or a mix of regions (i.e., mix of regions showing amplification, deletion, and normal). This methylation level can then be compared to a first cutoff as part of a first stage of analysis. If the cutoff is exceeded, thereby indicating a possibility of cancer, then the analysis above can be performed to determine whether the indication was a false positive. The final classification for the level of cancer can thus include the comparison of the parameter for the two methylation levels to a second cutoff.

The first methylation level can be a statistical value (e.g., average or median) of region methylation levels calculated for each region of the first set of regions. The second methylation level can also be a statistical value of region methylation levels calculated for each region of the second set of regions. As examples. the statistical values can be determined using one-sided rank sum test, Student's t-test, analysis of variance (ANOVA) test, or Kruskal-Wallis test.

As discussed above, plasma DNA of SLE patients may exhibit excesses or reductions in reads from certain genomic regions that are not likely to originate from cells with copy number aberrations. Besides analyzing methylation for certain regions (e.g., regions grouped by CNA), genomic characteristics may describe an altered plasma DNA methylation profile and regional representation yet without the correlation expected if the changes came from the same cell, as for cancer.

VI. SELECTION Of DNA MOLECULES USING ANTIBODIES

Anti-dsDNA antibody titers in patients have been shown to correlate with levels of SLE and other auto-immune diseases. Accordingly, in some embodiments of the present methods, DNA molecules can be selected using antibodies prior to analysis. For example, a biological sample can be incubated with a binding partner for anti-dsDNA antibodies, or passed over a chromatography column functionalized with such a binding partner. The antibodies are captured by the binding partner along with any DNA molecules to which the antibodies remain bound. Antibody-bound DNA molecules can then be removed (for example, eluted) from the binding partner, and non-antibody-bound DNA molecules can be collected from the portion of the sample that does not associate with the binding partner. Thus, antibody-bound and non-antibody-bound fractions of the sample can be collected, and these fractions can be analyzed separately. In some cases, anti-dsDNA antibodies are of the immunoglobulin G (IgG) isotype. A suitable IgG binding partner is protein G. Other binding partners can be used instead or in addition.

Antibody-based selection of DNA molecules can be performed in any of the methods disclosed herein. The biological sample used in any of these methods can be an antibody-bound fraction or IgG-bound fraction. On the other hand, the biological sample can be a non-antibody-bound fraction or non-IgG-bound fraction. The sample, or molecules of the sample, can then be analyzed as desired, for example to determine the sizes or sequences of molecules, the methylation levels of molecules, genomic regions, or portions of the genome of the organism from which the sample was obtained, and/or the representation of genomic regions in molecules of the sample.

VII. MATERIALS AND METHODS

A. Case Recruitment and Sample Processing

SLE patients attending the rheumatology clinic at the Department of Medicine and Therapeutics, Prince of Wales Hospital, Hong Kong, were recruited with written informed consent. The study was approved by the Joint Chinese University of Hong Kong-Hospital Authority New Territories East Cluster Clinical Research Ethics Committee. All patients fulfilled the American College of Rheumatology diagnostic criteria and their lupus disease activities were assessed by the Systemic Lupus Erythematosus Disease Activity Index (SLEDAI)[43]. Peripheral blood was collected in EDTA-containing tubes. The blood samples were first centrifuged at 1,600 g for 10 min at 4° C. and the plasma portion was further subjected to centrifugation at 16,000 g for 10 min at 4° C. to pellet the residual cells[44]. The blood cell portion was centrifuged at 2,500 g for 5 min to remove any remaining plasma. DNA was extracted from plasma using the DSP Blood Mini Kit (Qiagen) with modifications of the manufacturer's protocol as previously reported[45]. DNA was extracted from the peripheral blood cells using the QIAamp Blood Mini Kit (Qiagen) according to the manufacturer's blood protocol.

B. Preparation of DNA Libraries

Plasma DNA libraries were prepared using the Paired-End Sequencing Sample Preparation Kit (Illumina) according to the manufacturer's instructions, except the following modifications for preparing the DNA libraries for bisulfite sequencing. The methylated adapters (Illumina) were ligated to the DNA fragments. Then, the adapter-ligated DNA molecules, either treated or untreated with sodium bisulfite, were enriched by 10 cycles of PCR using the following recipe: 2.5 U PfuTurboCx hotstart DNA polymerase (Agilent Technologies), 1× PfuTurboCx reaction buffer, 25 μM dNTPs, 1 μl PCR Primer PE 1.0 and 1 μl PCR Primer PE 2.0 (Illumina) in a 50 μl-reaction. The thermocycling profile was: 95° C. for 2 min, 98° C. for 30 s, then 10 cycles of 98° C. for 15 s, 60° C. for 30 s and 72° C. for 4 min, with a final step of 72° C. for 10 min[46]. The PCR products were purified using AMPure XP magnetic beads.

C. DNA Sequencing and Alignment

The DNA libraries were sequenced for 75 bp in a paired-end format on HiSeq2000 instruments (Illumina). DNA clusters were generated with a Paired-End Cluster Generation Kit v3 on a cBot instrument (Illumina). Real-time image analysis and base calling were performed using the HiSeq Control Software (HCS) v1.4 and Real Time Analysis (RTA) Software v1.13 (Illumina), by which the automated matrix and phasing calculations were based on the spiked-in PhiX control v3 sequenced with the DNA libraries. After base calling, adapter sequences and low quality bases (i.e. quality score <20) on the fragment ends were removed.

For the analysis of DNA sequencing data, the sequenced reads were aligned to the non-repeat-masked human reference genome (NCBI build 37/hg19) with using the Short Oligonucleotide Alignment Program 2 (SOAP2) as previously described[38]. Reads mappable to a unique genomic location were selected. Ambiguous or duplicated reads were removed. Sequenced reads with insert size ≥600 bp were retained for analysis. Paired-end sequencing, where sequencing was performed for both ends of each DNA molecule, was used to analyze each sample in this study. By aligning the pair of end sequences of each DNA molecule to the reference human genome and noting the genome coordinates of the extreme ends of the sequenced reads, one could determine the lengths of the sequenced DNA molecules. Plasma DNA molecules are naturally fragmented into small molecules and the sequencing libraries for plasma DNA are typically prepared without any fragmentation steps[39,47]. Hence, the lengths deduced by the sequencing represented the sizes of the original plasma DNA molecules.

For the analysis of bisulfite DNA sequencing data, an additional step for identification of methylated cytosines was performed. The trimmed reads were processed by a methylation data analysis pipeline called Methy-Pipe[48]. In order to align the bisulfite converted sequencing reads, we first performed in silico conversion of all cytosine residues to thymines, on the Watson and Crick strands separately, using the reference human genome (NCBI build 37/hg19). We then performed in silico conversion of each cytosine to thymine in all the processed reads and kept the positional information of each converted residue. After that, SOAP2 was used to align the converted reads to the two pre-converted reference human genomes, with a maximum of two mismatches allowed for each aligned read. The cytosines originally present on the sequenced reads were recovered based on the positional information kept during the in silico conversion. The recovered cytosines among the CpG dinucleotides were scored as methylated. Thymines among the CpG dinucleotides were scored as unmethylated. We determined the methylation density of the whole human genome or any particular regions in the genome by determining the total number of unconverted cytosines at CpG sites as a proportion of all CpG sites covered by sequence reads mapped to the genome or the particular regions in the genome.

The unmethylated lambda DNA included during library preparation served as an internal control for estimating the efficiency of sodium bisulfite modification. All cytosines on the lambda DNA are converted to thymines if the bisulfite conversion efficiency is 100%.

VIII. EXAMPLE

A. Abstract of Example

We performed a high-resolution analysis of the biological characteristics of plasma DNA in systemic lupus erythematosus (SLE) patients using massively parallel genomic and methylomic sequencing. A number of plasma DNA abnormalities were found. First, aberrations in measured genomic representations (MGRs) were identified in the plasma DNA of SLE patients. The extent of the aberrations in MGRs in plasma DNA correlated with anti-dsDNA antibody level. Second, the plasma DNA of active SLE patients exhibited skewed molecular size distribution profiles with a significantly increased proportion of short DNA fragments. The extent of plasma DNA shortening in SLE patients correlated with the SLE disease activity index (SLEDAI) and anti-dsDNA antibody level. Third, the plasma DNA of active SLE patients showed decreased methylation densities. The extent of hypomethylation in plasma DNA correlated with SLEDAI and anti-dsDNA antibody level. To explore the impact of anti-dsDNA antibody on plasma DNA in SLE, a column-based protein G capture approach was employed to fractionate the immunoglobin G (IgG) bound and non-IgG-bound DNA in plasma. Compared with healthy individuals, SLE patients had elevated proportions of IgG-bound DNA in plasma. More IgG binding occurs at genomic locations showing increased MGRs. Furthermore, the IgG-bound plasma DNA was shorter in size and more hypomethylated than the non-IgG bound plasma DNA. These observations have enhanced our understanding of the spectrum of plasma DNA aberrations in SLE and may provide new molecular markers for monitoring this disease. Our results also suggest that caution should be exercised when interpreting plasma DNA-based noninvasive prenatal testing and cancer testing conducted for SLE patients.

B. Significance Statement

Through the use of massively parallel sequencing, we have demonstrated a spectrum of plasma DNA abnormalities in patients with systemic lupus erythematosus (SLE). These abnormalities include aberrant measured genomic representations, hypomethylation and shortening. The binding of anti-dsDNA to plasma DNA appears to be an important factor associated with these abnormalities. These findings provide interesting insights into the biology of plasma DNA in an autoimmune disease and have potential implications for the development of new molecular markers for SLE.

C. Data Deposition

Sequence data for the 69 subjects studied in this work who had consented to data archiving have been deposited at the European Genome-Phenome Archive (EGA), www.ebi.ac.uk/ega/, which is hosted by the European Bioinformatics Institute (EBI) (accession no. EGAS00001000962).

D. Introduction

Systemic lupus erythematosus (SLE) is a prototype autoimmune disease which has the potential of affecting multiple organ systems including the skin, muscles, bones, lungs, kidneys, as well as the cardiovascular and central nervous systems[5,9]. It can cause various tissue inflammation and damages in a chronic manner. Renal complications, infections, myocardial infarctions and central nervous system involvement are the major causes of death in SLE patients[49]. The extremely variable clinical manifestations and the absence of effective tests to monitor disease activity present a challenge for clinical management[9,49].

The etiology of SLE remains unknown and is multifactorial, involving genetic, epigenetic, environmental, hormonal and immunologic factors[9,50]. Cell death has been regarded as an important event in the pathogenesis of SLE as it leads to the release of antigens, such as nucleic acids, for immune complex formation, which may trigger a cascade of immune responses against the bodily tissues of the SLE patients[12,14]. Defects in the mechanism of cell death[15], impairment in the clearance of dead cells[17] and deficiency in DNase activity[18] have been implicated in SLE and suggested to result in the generation of autoantigens[12,14].

In addition, epigenetic regulation is an important mechanism for maintaining the normal functioning of the immune system. Perturbation of the epigenetic regulation can disrupt the immunologic self-tolerance[51]. Following the demonstration of impaired DNA methylation of T cells in SLE patients[52], an increasing amount of evidence has highlighted the contribution of epigenetic mechanisms in this disorder[53,54]. Hypomethylated apoptotic DNA from cells has been shown to be potentially pathogenic and may provoke the humoral and cellular immune responses in SLE[34].

SLE was one of the pathological conditions reported to be associated with the presence of circulating DNA nearly fifty years ago[20]. Since then, studies using various detection methods have demonstrated the elevations of circulating DNA in SLE patients[20-22]. In addition, early reports have highlighted that the circulating DNA that form immune complexes with autoantibodies in SLE patients display a characteristic fragmentation pattern which resembles the DNA laddering pattern of apoptosis by gel electrophoresis[26]. These findings have suggested an interplay of apoptosis and circulating DNA in the pathogenesis of SLE. However, there have been very few studies reporting the detailed biological characterization of circulating DNA in SLE.

The advent of massively parallel sequencing has enabled the investigation of circulating DNA at single-base resolution on a genome-wide scale, in fields such as non-invasive prenatal testing[37,47,55] and cancer detection[41,42,56,57]. It would be of great interest to use this technology to explore the genomic and methylomic features of plasma DNA in SLE patients, as we postulated that the pathogenesis of deregulated cell death, altered epigenetic regulation and production of autoimmune antibodies in SLE patients might cause abnormal patterns of circulating DNA. Hence, in this study, we delineated the biological characteristics of DNA in the plasma of SLE patients using genomewide genomic and methylomic sequencing.

E. Results i. Genomic Representations of Plasma DNA in SLE Patients.

First, we assessed if the plasma DNA molecules in the circulation of SLE patients were evenly distributed across the genome. Plasma DNA from 24 SLE patients and 11 healthy individuals were analyzed by paired-end massively parallel sequencing. SLE patients were divided into active and inactive groups according to their SLE disease activity index (SLEDAI), which is a clinical index for the measurement of disease activity[43]. Fifteen patients with SLEDAI below or equal to 6 (median: 4, range: 0-6) were classified as the inactive group, while 9 patients with SLEDAI over 6 (median: 8, range: 7-16) were classified as the active group. A median of 120 million (range: 18-207 million) alignable and nonduplicated paired-end reads were obtained for the plasma DNA per case for subsequent analyses.

We assessed the genomic distribution of plasma DNA across segments (bins) of the human genome, each of 1 Mb in size. The number of sequence reads in each bin was tallied and adjusted by GC-correction as previously described[41]. The control group consisted of 11 healthy individuals and this group showed even genomic distribution of the plasma DNA molecules as reported previously (FIG. 33, the innermost ring of the circos plot[58]). To determine if the plasma DNA profiles of SLE patients showed differences in genomic representation, we compared the number of plasma DNA sequences aligned to a bin to the mean number detected among the control group for the same bin. We expressed the difference as a z-score, which was the number of standard deviations (SDs) deviated from the mean of the control group. Bins with z-scores below −3 and above +3 were considered as showing significant under- and over-representation, respectively. We termed these changes as aberrant measured genomic representations (MGRs).

Figure 33:
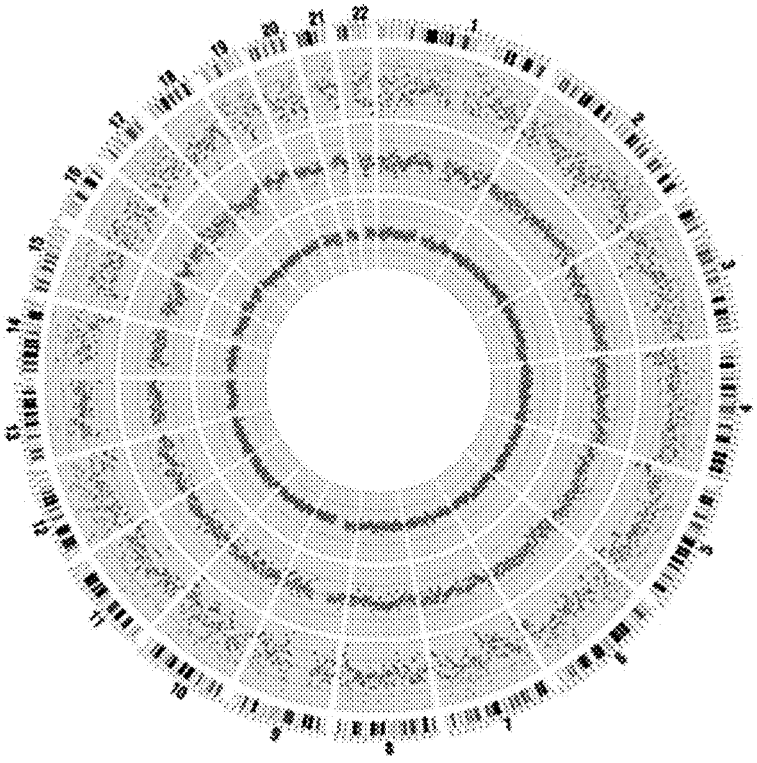
FIG. 33 depicts Circos plots showing the genomic distributions of plasma DNA for a representative case in each of the control, inactive SLE and active SLE groups in the Example. From inside to outside, the rings show data from a representative healthy individual (C005), inactive SLE patient (S011), active SLE patient (S112), and ideograms of the human chromosomes, respectively. Each dot represents a 1-Mb bin. The green, red and grey dots represent bins with significant increased, decreased and normal MGRs, respectively. The distance between intervals represents a z-score difference of 5.
Figure 34:
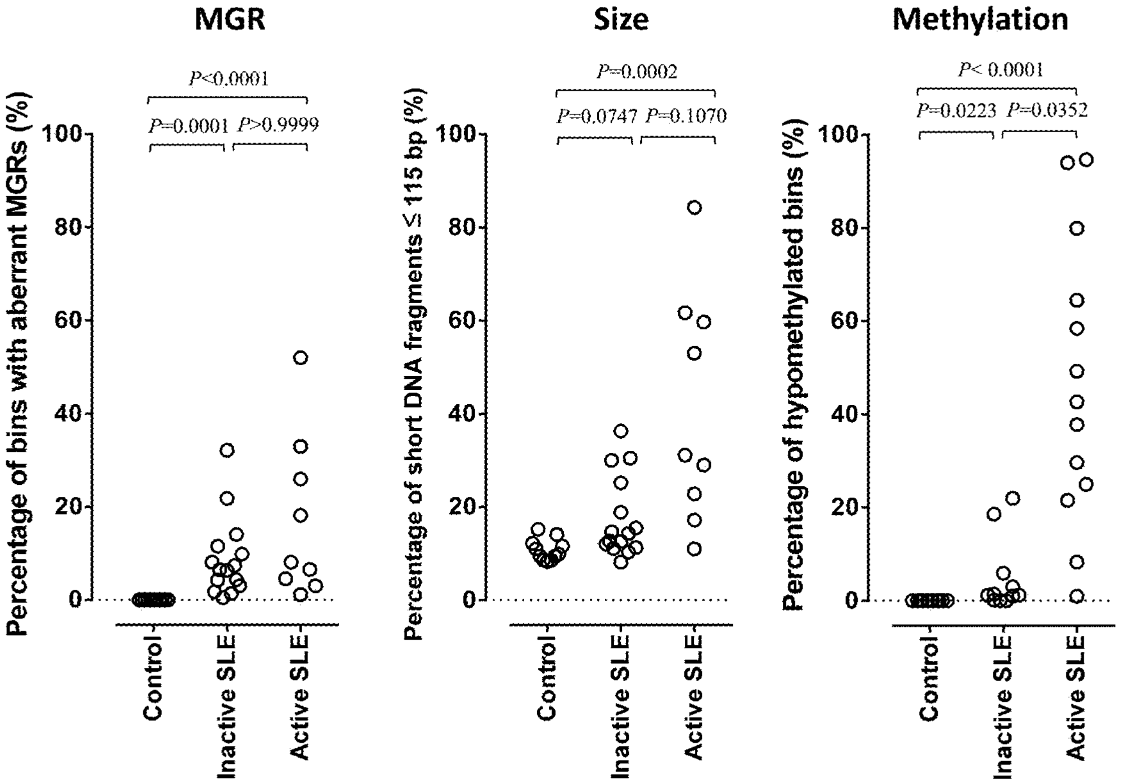
FIG. 34 shows genomic and methylomic features of plasma DNA among subject groups in the Example. The portion of the figure labeled “MGR” represents the percentage of bins with aberrant MGRs. The portion of the figure labeled “Size” represents the percentage of short DNA fragments. The portion of the figure labeled “Methylation” represents the percentage of hypomethylated bins. Statistical comparisons were performed by the Kruskal-Wallis test followed by the post-hoc Dunn’s test.

The percentages of bins with aberrant MGRs among the healthy individuals, inactive and active SLE patients are shown in FIG. 34 ("MGR"). We tested for aberrant MGRs in the plasma of each healthy individual by comparing against the genomic distributions of the remaining control group. None of the healthy individuals exhibited any bin with aberrant MGRs in plasma. The percentages of bins with aberrant MGRs were higher among the SLE patients (active group: median 8.1%, range 1.1-52%; inactive group: median 6.5%, range 0.5-32.1%) when compared with the controls (P<0.0001, Kruskal-Wallis test) (Table 1). The MGR patterns of one representative case in each of the control, inactive SLE and active SLE groups are shown in FIG. 33. Correlation analyses were performed between the percentage of bins with aberrant MGRs in SLE patients with the serum anti-dsDNA antibody levels (r=0.604, P=0.0018, Spearman's correlation), and SLEDAI (r=0.226, P=0.29, Spearman's correlation).

ii. Size Analysis of Plasma DNA in SLE Patients.

Figure 35:
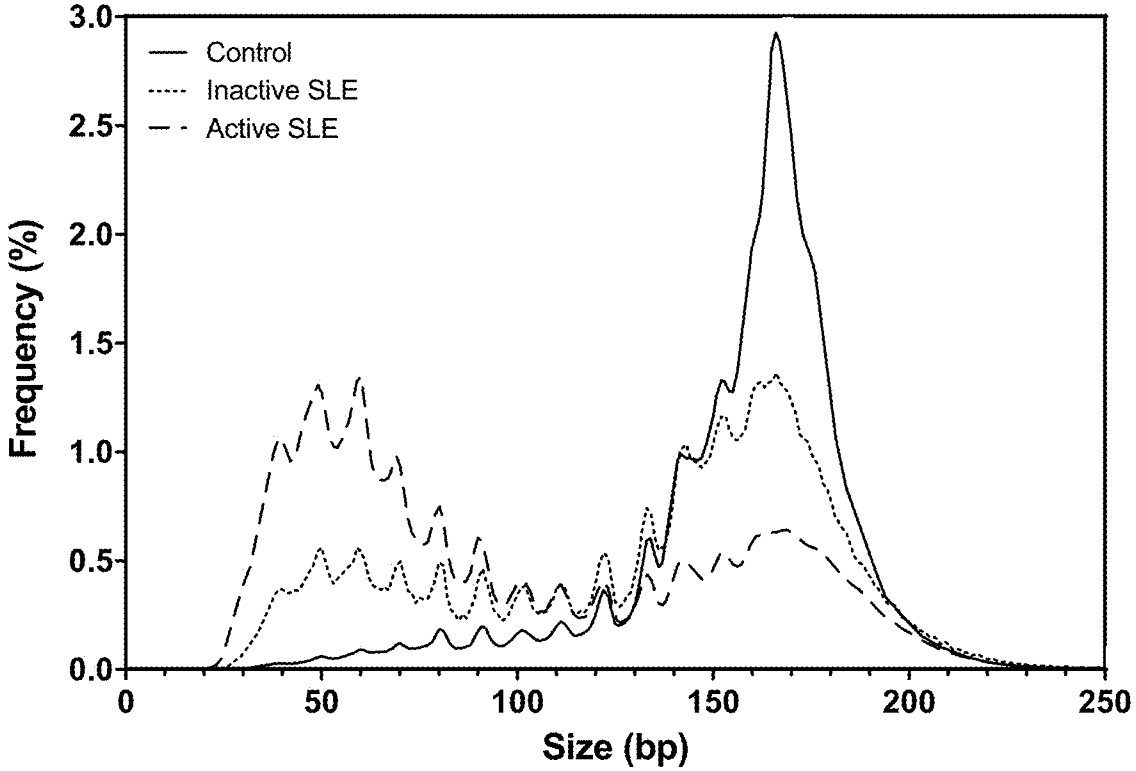
FIG. 35 shows size distributions of plasma DNA molecules of representative cases for control (C005) (blue), inactive SLE (S081) (green) and active SLE (S082) (red) groups in the Example.

The sizes of plasma DNA molecules in the samples discussed in the previous section were deduced from the start and end coordinates of the paired-end reads[38]. The size distribution profiles of one healthy individual, one active and one inactive SLE patients are shown in FIG. 35. The size distribution of plasma DNA in healthy individuals showed a major peak at 166 bp and a series of smaller peaks occurring at a 10-bp periodicity (FIG. 35). The size distribution profiles of the SLE patients were different. The height of the 166 bp peak was reduced while the other peaks for DNA fragments in smaller sizes, particularly those shorter than 115 bp, were elevated. These changes were more pronounced in the active SLE group than the inactive SLE cases.

To systematically compare the size profiles between all samples, we defined a plasma DNA molecule ≤115 bp in size as a short DNA fragment and determined the percentage of short plasma DNA molecules in each sample. The data are shown in FIG. 34 ("Size"). The median percentages of short plasma DNA fragments in the plasma of healthy individuals, inactive SLE and active SLE patients were 10% (range: 8-15%), 14% (range: 8-36%) and 31% (range: 11-84%), respectively. Positive correlations were observed between the percentage of short DNA fragments and SLEDAI (r=0.532, P=0.0076, Spearman's correlation) and the anti-dsDNA antibody level (r=0.758, P<0.0001, Spearman's correlation).

iii. Methylation Status of DNA in Plasma of SLE Patients.

Another sample set consisting of 24 SLE patients and 10 healthy individuals were subjected to methylation analysis. For the SLE patients, 4 inactive (S006, S013, S017 and S019) and 4 active cases (S004, S005, S010 and S015) had been studied in the above-mentioned MGR and size analyses. Plasma DNA was bisulfite converted and analyzed by paired-end massively parallel sequencing as previously described[40]. A median of 125 million (range: 26-191 million) alignable and nonduplicated reads were obtained per case for subsequent analysis. Among the 24 SLE cases, 11 were in the inactive SLE group (SLEDAI median: 3, range: 0-5) and 13 were in the active SLE group (SLEDAI median: 8, range: 7-18).

Figure 36:
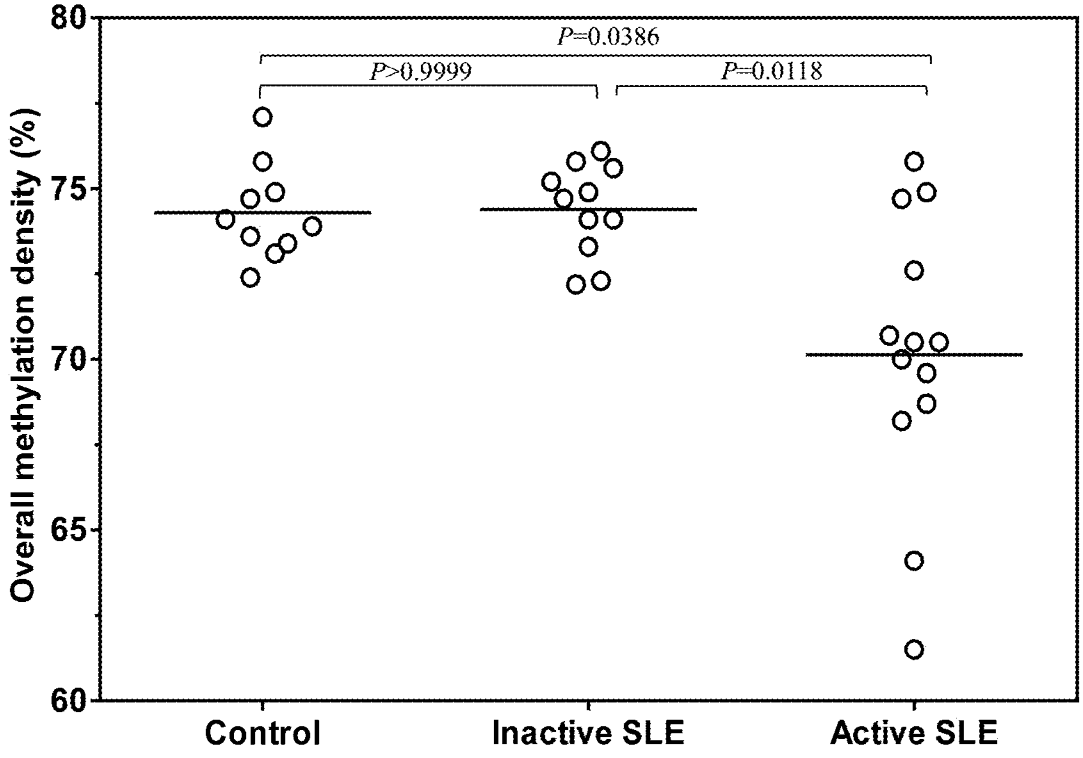
FIG. 36 shows genomewide methylation density of plasma DNA among subject groups in the Example. Statistical comparisons were performed by the Kruskal-Wallis test followed by the post-hoc Dunn’s test.

The genomewide methylation density of plasma DNA for each case refers to the proportion of CpG sites deemed to be methylated among all the CpG sites covered by sequence reads[40]. The genomewide methylation density of the active SLE group (70.1%±4.5%) was significantly reduced compared to both the healthy individuals (74.3%±1.4%, P=0.0367, Kuskal-Wallis test, post-hoc Dunn test) and the inactive SLE group (74.4%±1.3%, P=0.0118, Kruskal-Wallis test, post-hoc Dunn test) (FIG. 36).

Figure 37:
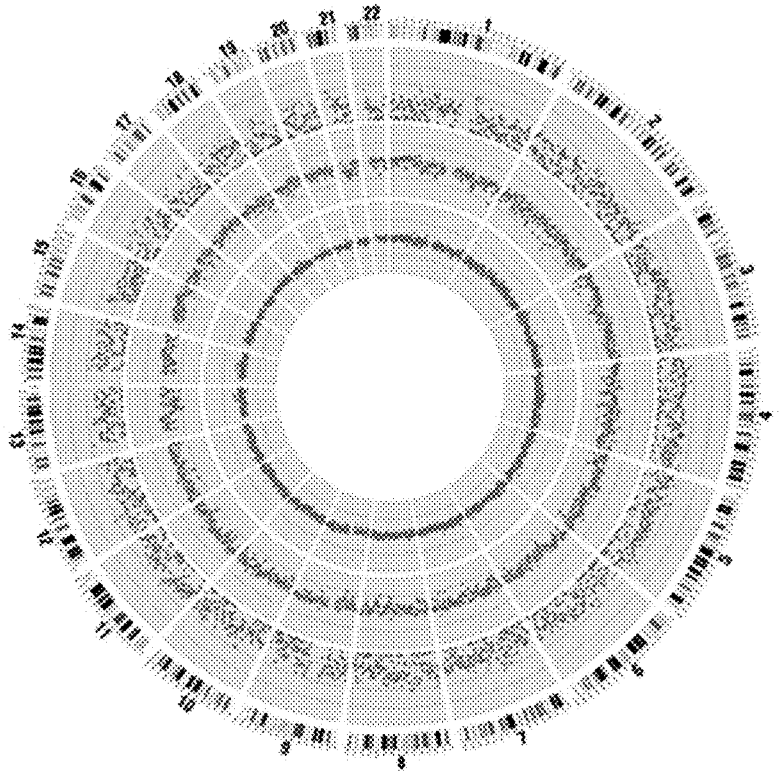
FIG. 37 shows plasma methylation profile analysis for a representative case in each of the control, inactive SLE and active SLE groups in the Example. From inside to outside, the rings show data from a representative healthy individual (C040), inactive SLE patient (S124), active SLE patient (S027), and ideograms of the human chromosomes, respectively. Each dot shows the methylation density for a 1-Mb bin. The green, red and grey dots represent bins with significant hypermethylation, hypomethylation and normal methylation, respectively. The distance between intervals represents a z-score difference of 5.

Next we analyzed the methylation densities of each 1-Mb bin across the genome. For every bin, the plasma DNA methylation densities of the SLE patients were compared to the mean methylation density obtained from the 10 healthy individuals of the corresponding bin. Bins with methylation densities that were more than 3 SDs lower or higher than the mean of the control group, namely with z-scores below −3 or above +3, were deemed as significantly hypo- and hypermethylated, respectively[57]. The percentages of bins with significant hypomethylation among the healthy individuals, inactive and active SLE patients are shown in FIG. 34 ("Methylation"). Patients in the active group showed more hypomethylated bins (median: 42.7%, range: 1-94.7%) than the inactive group (median: 1.2%, range: 0-22%) (Table 2). The methylation patterns of one healthy individual, one active and one inactive SLE patients are shown in FIG. 37. The percentage of hypomethylated bins correlated with SLEDAI (r=0.653, P=0.0005, Spearman's correlation) and anti-dsDNA antibody levels (r=0.555, P=0.0059, Spearman's correlation) of the SLE patients.

Figure 38:
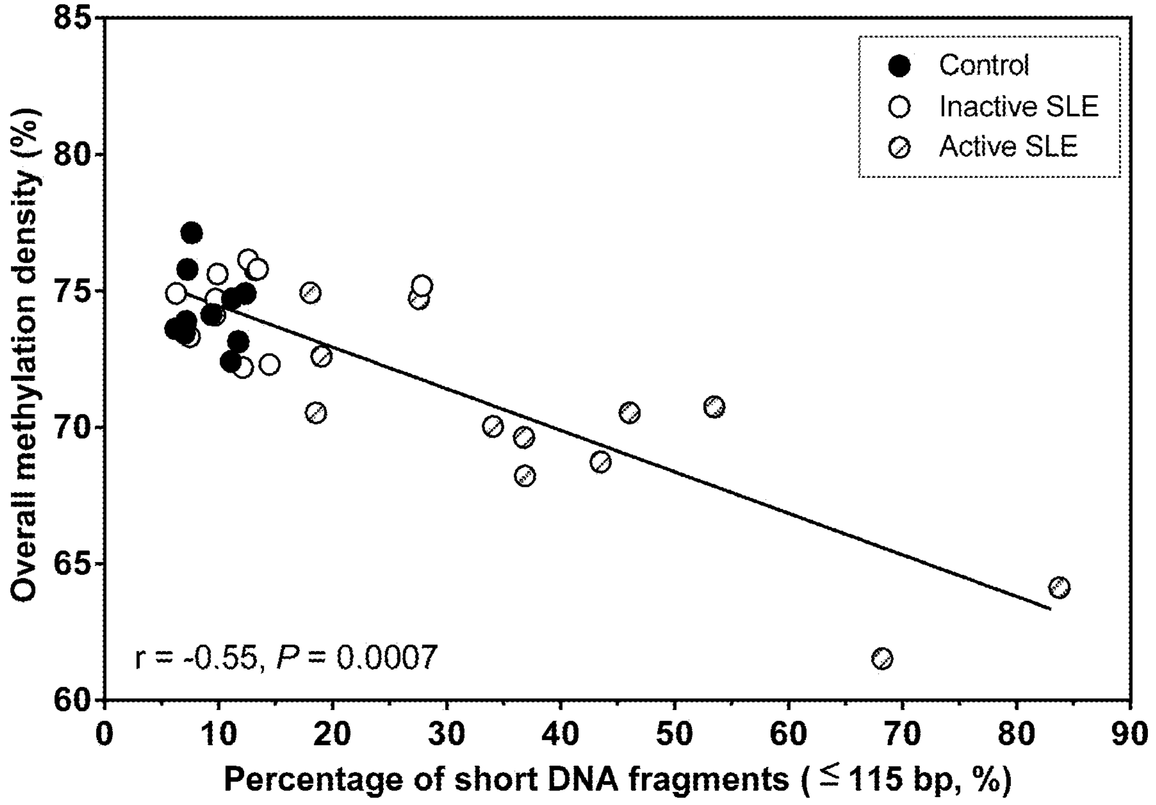
FIG. 38 shows a relationship between genomewide methylation density and proportion of short DNA fragments in plasma. Blue, green and red circles represent the cases in the control, inactive SLE and active SLE groups of the Example, respectively. The correlation coefficient was calculated by Spearman’s correlation analysis.
Figure 39:
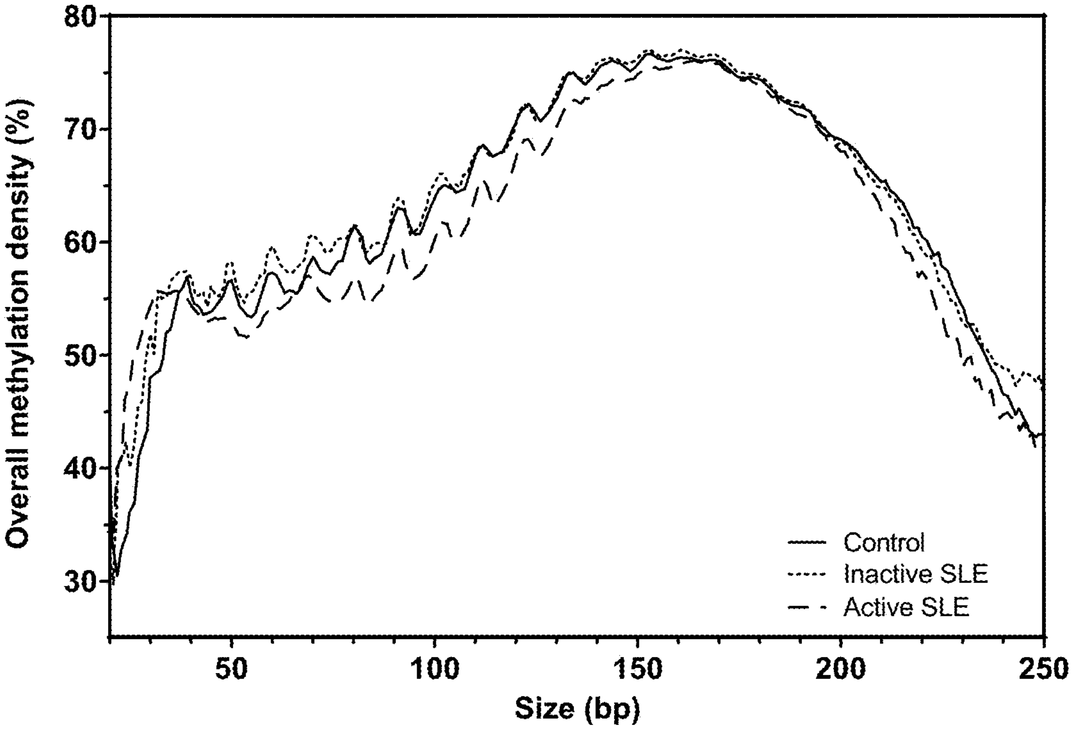
FIG. 39 shows overall methylation density of plasma DNA of different sizes among subject groups in the Example. Blue, green and red lines represent the median genomewide methylation densities of the control, inactive SLE and active SLE group, respectively.

We reported in a previous study that shorter plasma DNA fragments tend to be more hypomethylated[40]. Here we explored if a similar relationship is present in the plasma of SLE patients. First, the genomewide methylation density was inversely correlated with the proportion of short DNA (≤115 bp) in all individuals (r=−0.550, P=0.0007, Spearman's correlation; FIG. 38). Next, we determined the methylation densities of DNA fragments of different sizes ranging from 20 bp to 250 bp, using sequence reads that covered at least 1 CpG site[40] (FIG. 39). For fragments between 40 bp and 180 bp, which accounted for the majority of plasma DNA molecules, the same trend as previously reported for the plasma of pregnant women was observed[40]. It is noteworthy that the active SLE group showed greater reductions in methylation densities with progressive shortening of the plasma DNA fragments when compared with the healthy individuals and patients in the inactive SLE group (FIG. 39).

iv. Effects of IgG Binding on Plasma DNA of SLE Patients.

Autoantibodies have a direct contribution in the pathogenesis of SLE[9,49] and are responsible for many of the clinical manifestations[59]. One of such autoantibodies is the anti-dsDNA antibody, which can bind to the DNA in plasma[8]. Studies have reported that IgG-class anti-dsDNA antibody has high avidity for dsDNA and is implicated in the pathogenesis of SLE[8,60]. We hypothesized that the binding of anti-dsDNA antibody to plasma DNA might alter the stability or clearance of DNA in plasma and might result in observable aberrations in genomic representation, size or methylation profiles of plasma DNA. To study the effect of anti-dsDNA antibody binding on plasma DNA, two sample sets were recruited: one for genomic representation and size analysis, and the other for methylation level analysis. Each sample set included 2 healthy individuals, 2 inactive SLE patients and 2 active SLE patients. For each case, the plasma sample was divided into 2 portions. One portion was not subjected to any treatment and was termed the neat fraction. The other portion was incubated with protein G and subjected to column capture. Protein G binds human IgG, including anti-dsDNA antibody. Therefore, column-based protein G capture further allowed the plasma sample to be separated into IgG-bound and non-IgG-bound fractions. The genomic representation, molecular size and methylation profiles were compared among the neat, IgG-bound and non-IgG-bound DNA fractions.

The percentages of IgG-bound DNA were elevated in the plasma of inactive (median: 42%, range: 6-70%) and active SLE patients (median: 52%, range: 14-90%), when compared with the healthy individuals (median: 7%, range: 4-8%) (Table 3).

Figure 40:
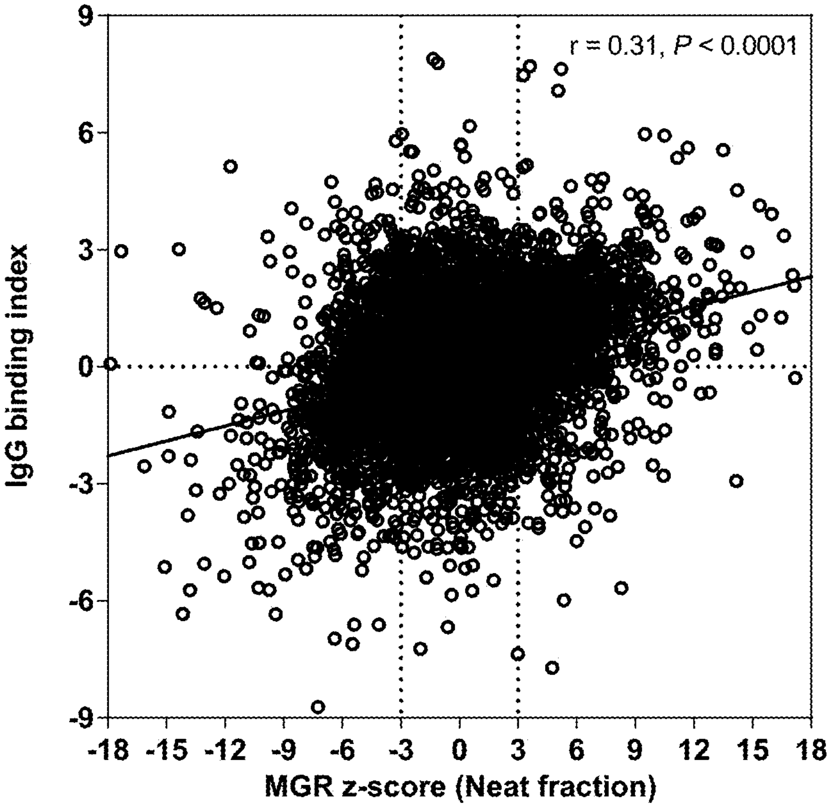
FIG. 40 shows a relationship between IgG binding index and MGR z-score of the SLE cases with high anti-dsDNA antibody levels (S081, S082, S112) in the Example. The correlation coefficient was calculated by Pearson’s correlation analysis.

For genomic representation analysis, the z-score for each 1-Mb bin was calculated in the neat, IgG-bound and non-IgG-bound fractions. Next, we calculated the z-score difference between the IgG-bound and non-IgG-bound fractions for each bin, expressed as the 'IgG binding index'. The IgG binding index of each bin was then compared with the z-score in the neat fraction for the corresponding bin (FIG. 40). We hypothesized that a higher proportion of plasma DNA fragments originating from regions showing increased MGRs were bound by anti-dsDNA antibody and would be found in the IgG-bound fraction. Hence, the IgG binding index for such locations should be higher. For regions exhibiting decreased MGRs, the reverse would be true and the IgG binding index should be more negative. Indeed, for SLE cases with high anti-dsDNA antibody levels (S081, S072, S112), the z-scores of bins with aberrant MGRs in the neat fractions showed a positive relationship with the corresponding IgG binding index (r=0.31, p<0.0001, Pearson's correlation) (FIG. 40).

Figure 41:
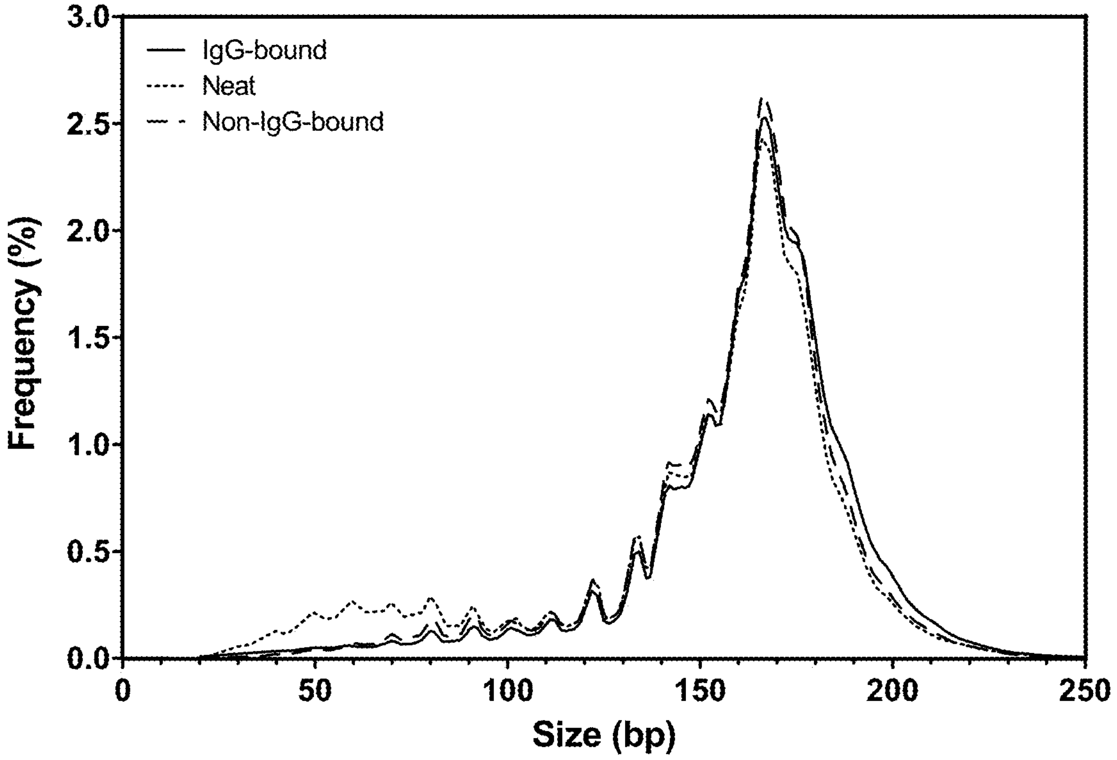
FIG. 41 shows size distributions of plasma DNA molecules with and without IgG binding in a healthy control (C020). Blue dash, red solid and green solid lines represent the neat, IgG-bound and non-IgG-bound fractions, respectively.
Figure 42:
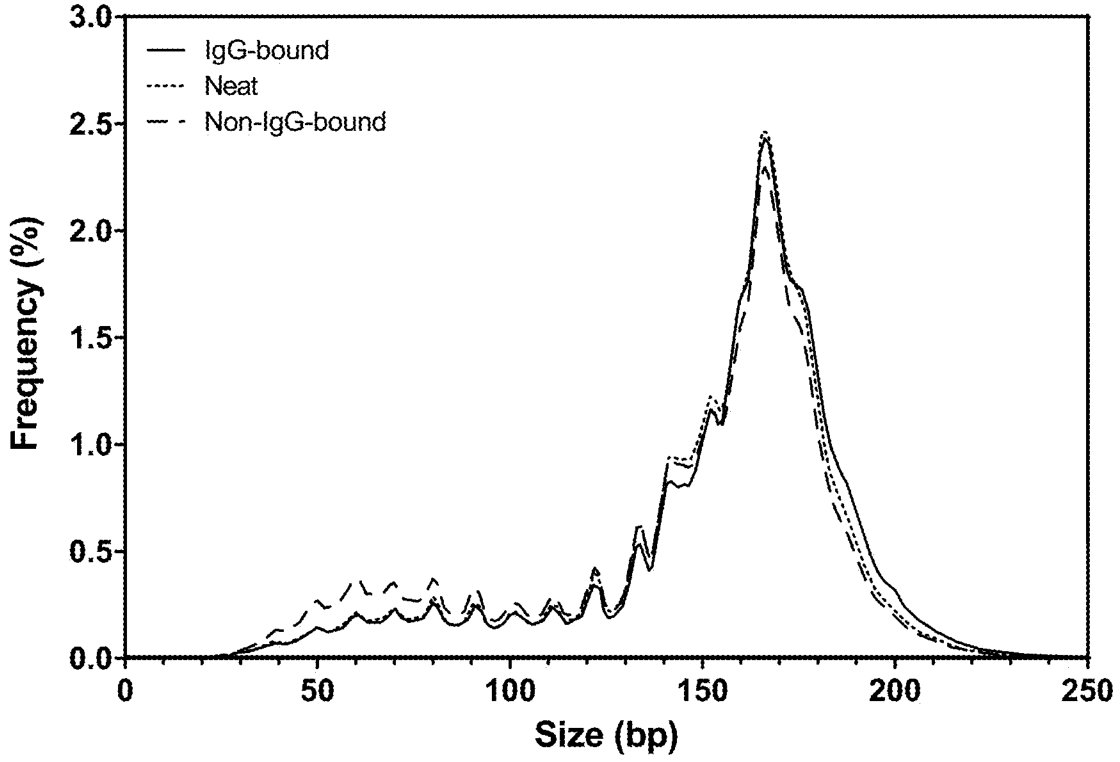
FIG. 42 shows size distributions of plasma DNA molecules with and without IgG binding in a healthy control (C021). Blue dash, red solid and green solid lines represent the neat, IgG-bound and non-IgG-bound fractions, respectively.
Figure 43:
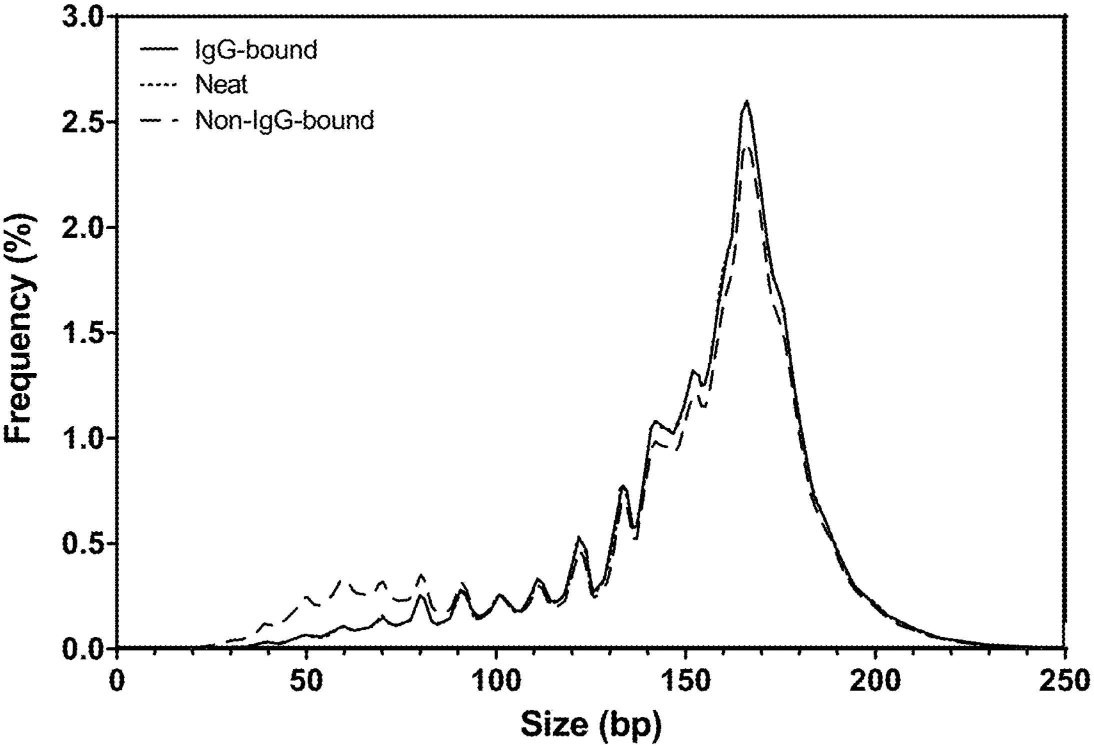
FIG. 43 shows size distributions of plasma DNA molecules with and without IgG binding in an SLE case with low anti-dsDNA antibody levels (S073). Blue dash, red solid and green solid lines represent the neat, IgG-bound and non-IgG-bound fractions, respectively.
Figure 44:
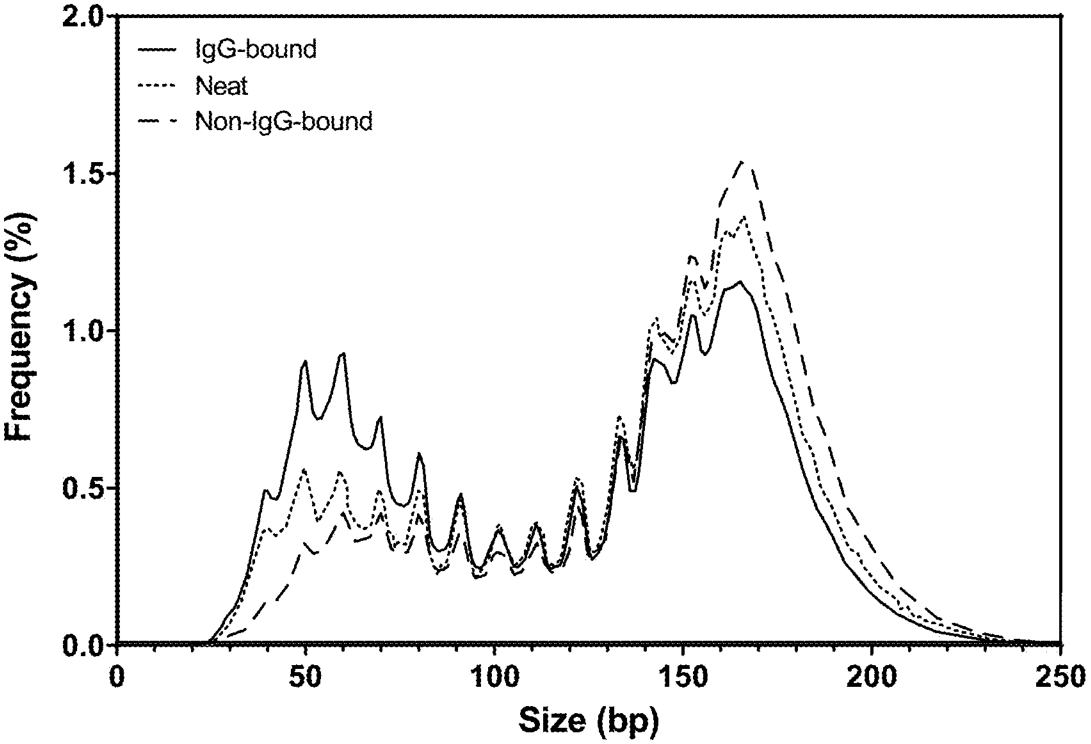
FIG. 44 shows size distributions of DNA molecules with and without IgG binding in plasma of a representative SLE patient (S081) of the Example. Blue dash, red solid and green solid lines show data for the neat, IgG-bound and non-IgG-bound fractions, respectively.
Figure 45:
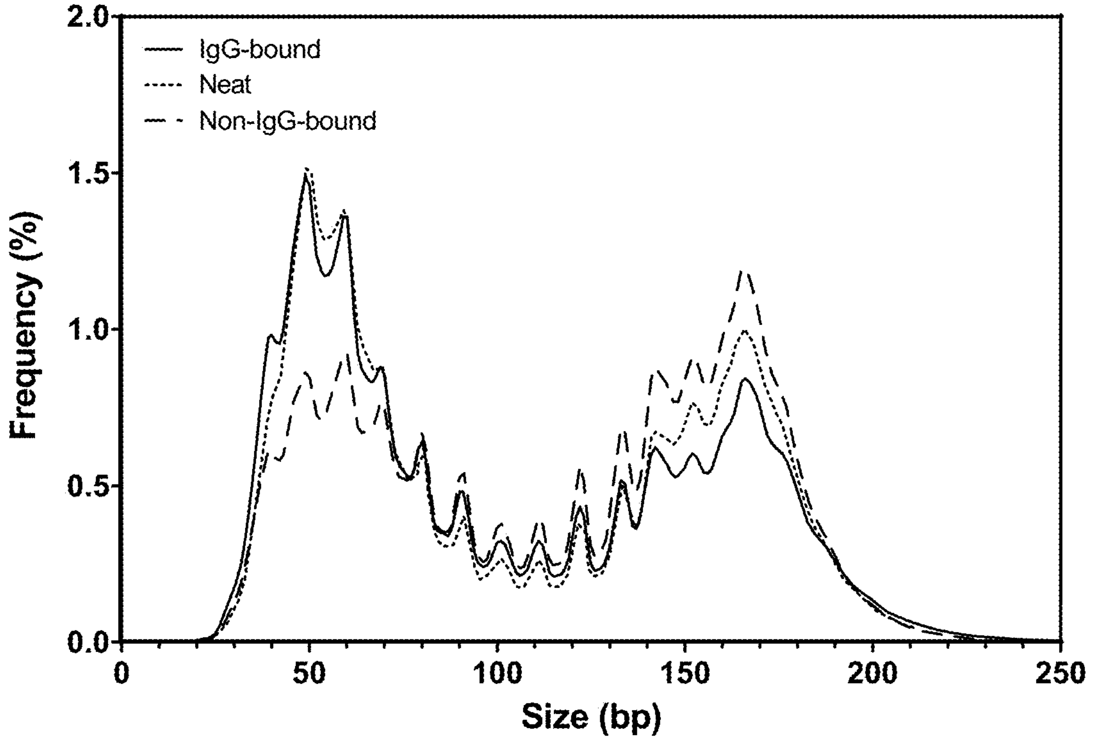
FIG. 45 shows size distributions of plasma DNA molecules with and without IgG binding in an SLE case with high antibody levels (S082). Blue dash, red solid and green solid lines represent the neat, IgG-bound and non-IgG-bound fractions, respectively.
Figure 46:
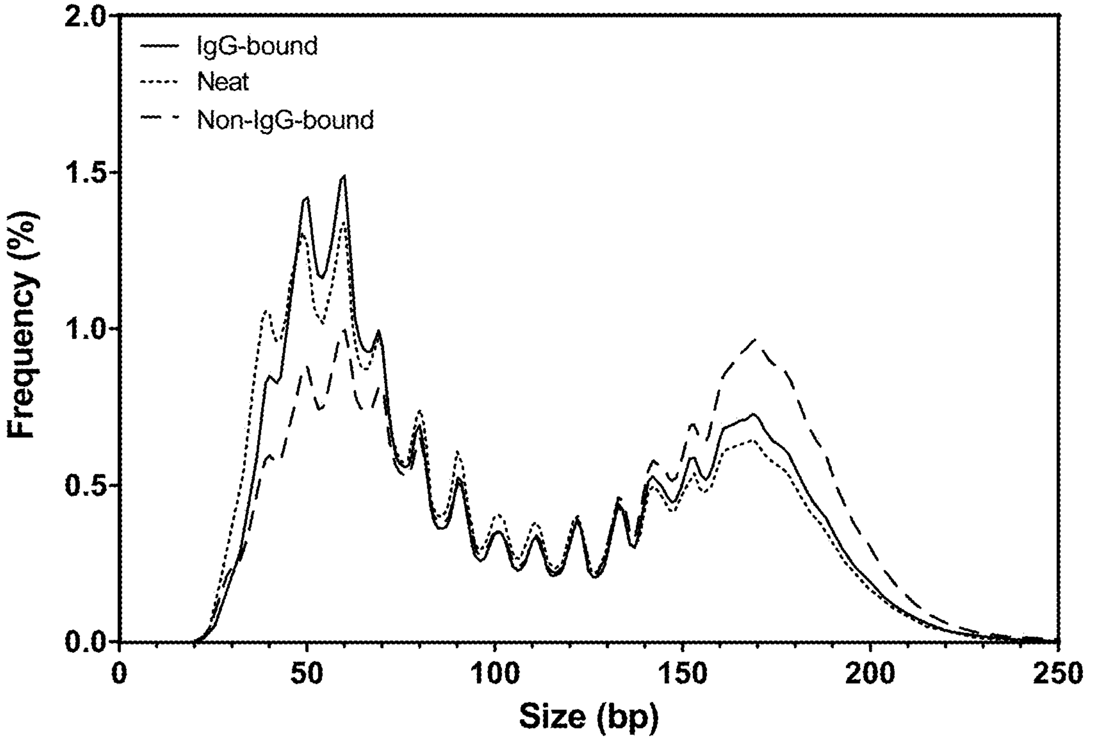
FIG. 46 shows size distributions of plasma DNA molecules with and without IgG binding in an SLE case with high antibody levels (S112). Blue dash, red solid and green solid lines represent the neat, IgG-bound and non-IgG-bound fractions, respectively.
Figure 47:
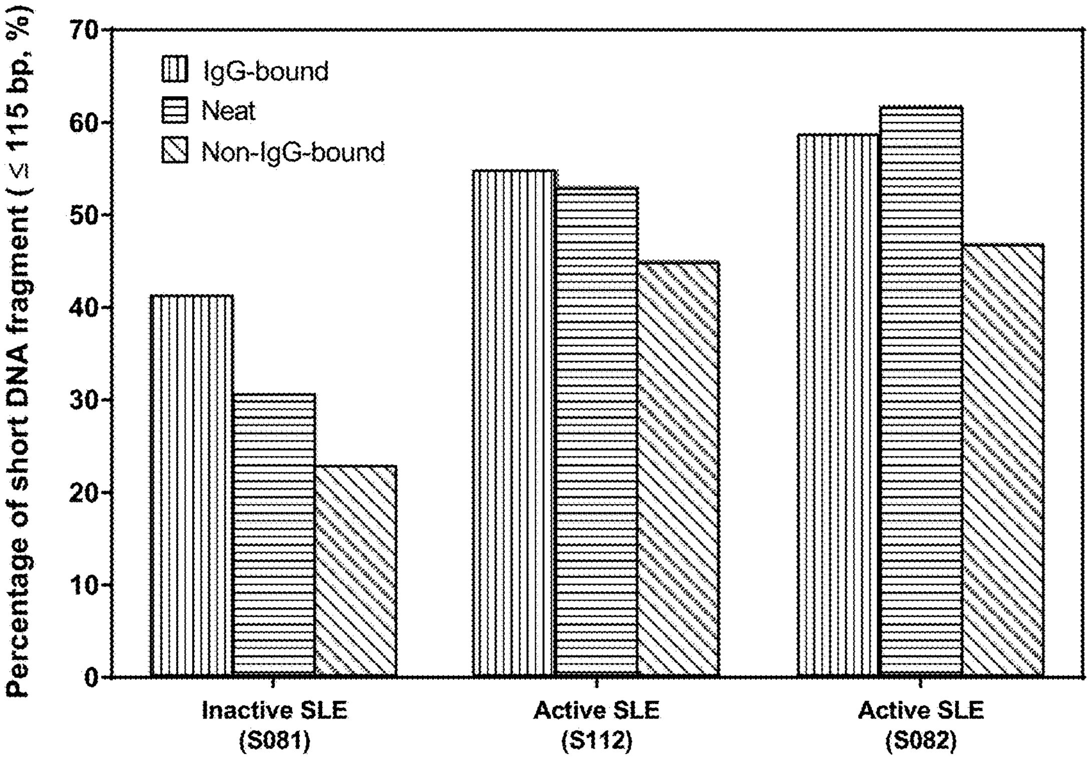
FIG. 47 shows percentages of short DNA fragments (≤115 bp) in plasma of SLE patients with high anti-dsDNA antibody levels (S081, S112 and S082). Red, blue and green bars (arranged left to right for each patient) indicate the IgG-bound, neat and non-IgG-bound fractions, respectively.

For the size analysis, the SLE case (S073) with SLEDAI 0 and negative anti-dsDNA antibody showed similar plasma DNA size distribution profiles in the neat, IgG-bound and non-IgG-bound fractions as the 2 healthy individuals (FIGS. 41-43). In contrast, for three SLE patients (S081, S082 and S112) with high anti-dsDNA antibody levels and SLEDAI ≥6, the size distribution profiles demonstrated a shortening of plasma DNA in each of the neat, IgG-bound and non-IgG-bound fractions (FIGS. 44-46). The IgG-bound fractions of these 3 SLE patients showed an enrichment of short DNA fragments ≤115 bp when compared with the non-IgG-bound fractions (FIG. 47).

Figure 48:
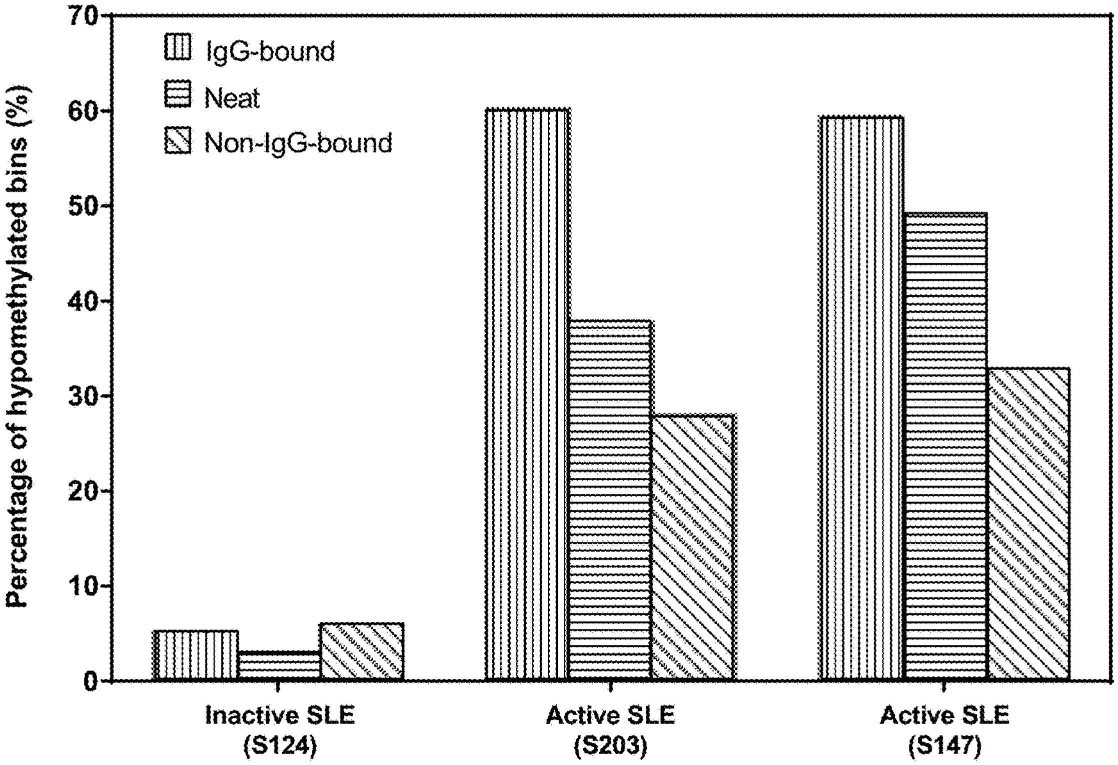
FIG. 48 shows percentages of significant DNA hypomethylation in plasma of SLE patients with high anti-dsDNA antibody levels (S124, S203 and S147). Red, blue and green bars (arranged left to right for each patient) indicate the IgG-bound, neat and non-IgG-bound fractions, respectively.

For the methylation analysis, compared with the 2 healthy individuals, SLE patients had lower genomewide methylation densities in each of the neat, IgG-bound and non-IgG-bound fractions (Table 4). For the 2 active SLE patients with high anti-dsDNA antibody levels (S147 and S203), the IgG-bound fractions showed the lowest genomewide methylation densities and the highest number of hypomethylated bins. Correspondingly, the non-IgG-bound fractions had the highest genomewide methylation densities and lowest number of hypomethylated bins (Table 4). Among these 2 SLE cases, the percentages of hypomethylated bins decreased in the following order: IgG-bound, neat and non-IgG-bound fractions (FIG. 48). On the other hand, for the 2 SLE cases with low anti-dsDNA antibody levels (S124, 125), the genomewide methylation densities and number of hypomethylated bins were similar between the IgG-bound and non-IgG-bound fractions (Table 4).

F. Discussion

In this study, we investigated the characteristics of plasma DNA of SLE patients in a high-resolution and genomewide manner with the use of paired-end massively parallel sequencing. In general, the higher the disease activity, the greater the extent and the wider the range of plasma DNA aberrations were observed. Plasma DNA of SLE patients showed aberrant MGRs, size shortening and hypomethylation. We further obtained evidence that suggested those plasma DNA aberrations were at least in part related to DNA binding by IgG class antibodies, for example anti-dsDNA antibodies. These observations are particularly interesting because they suggest that a blood constituent, namely anti-dsDNA antibody, could alter the molecular characteristics and profile of plasma DNA.

We showed that the genomic representations of plasma DNA in SLE patients were different from those of healthy controls. The percentages of bins showing aberrant MGRs correlated with the anti-dsDNA antibody level but not the SLEDAI. We therefore hypothesized that antibody binding of plasma DNA may be related to the observed aberrant MGRs. In the IgG binding experiments, we indeed showed that more plasma DNA molecules originating from the regions with increased MGRs were bound by IgG. Perhaps the binding of anti-dsDNA antibody to plasma DNA would protect the bound DNA from enzymatic degradation, or would impair the clearance mechanism[61]. Studies have also reported the preferential binding of anti-DNA antibody to particular DNA sequences, for example, DNA fragments containing certain CpG motifs[61,62]. The retention of antibody bound DNA might therefore enhance the genomic representation in regions with preference for antibody binding, while regions with less antibody binding preference would be underrepresented. These changes might then be detected as increased MGRs and decreased MGRs, respectively.

Currently, a number of noninvasive prenatal tests for fetal aneuploidy screening were based on the detection of copy number aberrations in maternal plasma DNA[45,47,55,]. Therefore, caution should be taken when applying such tests on pregnancies with underlying SLE, as the aberrant MGRs might reflect the activity of SLE, rather than the genomic aberrations originating from the fetus. Similarly, as plasma DNA sequencing for copy number aberrations[41,42] and hypomethylation[57] has been reported for cancer detection, one should also be wary of the possibility of false-positive results for patients with SLE.

In terms of size analysis, plasma of SLE patients showed an increased proportion of short DNA fragments. The proportion of short DNA fragments (≤115 bp) in the plasma of the active SLE patients was 3-fold higher than that of healthy individuals and could contribute up to 84% of the total DNA in plasma. Hence, when plasma DNA size analysis is used for noninvasive prenatal testing[64] in pregnant subjects with SLE, the possibility of false-positive results due to the underlying SLE should be borne in mind.

The shortening of plasma DNA in SLE patients may be due to the increased production or decreased clearance of short DNA fragments. Our data show that the shortening of plasma DNA was positively correlated with the disease activity of the SLE patients and the anti-dsDNA antibody level. Furthermore, the IgG binding data demonstrated that short DNA fragments (≤115 bp) were enriched in the IgG-bound fraction. Therefore, the data seem to suggest that there is preferential binding of anti-DNA antibody to short DNA fragments hindering the clearance of short DNA from the circulation.

Our previous data showed that plasma DNA of healthy individuals and pregnant women have a characteristic size profile with a prominent peak at 166 bp and a series of smaller peaks that are 10 bp apart[37]. This characteristic pattern was reminiscent of the length of DNA in a nucleosomal unit. We have also previously shown that the shorter plasma DNA molecules tend to be more hypomethylated than the longer molecules[40]. Hypomethylated DNA tended to be less densely packed with histones[65] and might be more susceptible to enzymatic degradation and/or provide more access to antibody binding. We therefore studied the methylation profile of DNA in the plasma of SLE patients. We found that plasma DNA of active SLE patients was generally hypomethylated when compared with that of healthy individuals. The degree of hypomethylation correlated with the disease activity and the anti-dsDNA antibody level. The IgG binding experiment showed that the IgG-bound plasma DNA molecules were more hypomethylated (FIG. 48). This observation suggests that some hypomethylated DNA molecules are retained in plasma of SLE patients due to antibody-binding. On the other hand, our data show that antibody-binding results in an enrichment of short plasma DNA fragments. These observations were therefore consistent with our finding that there was a relationship between the genomewide methylation density and the size of plasma DNA in SLE patients, in which the shorter DNA fragments were more hypomethylated. This finding was also consistent with our previous study on circulating fetal DNA[40].

Early studies have reported the phenomenon of DNA release from lymphocytes into serum[66,67.] Interestingly, a number of recent studies have reported the hypomethylation of T cells in SLE patients[68,69]. Hence, the release of DNA from hypomethylated cells, such as T cells, might be another mechanism that could contribute towards the hypomethylation of plasma DNA of SLE patients.

In summary, plasma DNA of SLE patients could exhibit aberrant MGRs, size shortening and hypomethylation. These features might potentially be useful as biomarkers for SLE diagnosis or monitoring. Further studies with larger sample size, serial specimen collections and sub-group analysis of cases with specific clinical manifestations (e.g. renal involvement) may provide a more in-depth understanding of plasma DNA in SLE patients and its potential value for clinical practice. Our study also highlights the possibility that the study of plasma nucleic acids would be a valuable venue for research for other autoimmune diseases.

G. Materials and Methods of Example i. Case Recruitment and Sample Processing.

SLE patients attending the rheumatology clinic at the Department of Medicine and Therapeutics, Prince of Wales Hospital, Hong Kong, were recruited with written informed consent. The study was approved by the Joint Chinese University of Hong Kong-Hospital Authority New Territories East Cluster Clinical Research Ethics Committee. All patients fulfilled the American College of Rheumatology diagnostic criteria and their lupus disease activities were assessed by the Systemic Lupus Erythematosus Disease Activity Index (SLEDAI)[43]. Peripheral blood was collected in EDTA-containing tubes. The blood samples were first centrifuged at 1600 g for 10 min at 4° C. and the plasma portion was further subjected to centrifugation at 16000 g for 10 min at 4° C. to pellet the residual cells.

ii. Separation of IgG-Bound and Unbound DNA in Plasma.

The plasma samples were separated into the IgG-bound and non-IgG-bound fractions using the NAb Spin Column (Thermo Fisher Scientific), which contained an immobilized protein G resin for IgG protein capturing. The separation was performed according to the manufacturer's instructions, except for the following modifications for purifying the IgG-bound fraction. After the elution of the non-IgG-bound fraction, the NAb Spin Column was washed with phosphate buffered saline for 6 times. To ensure a complete removal of the non-IgG-bound fraction before elution of the IgG-bound fraction, the final phosphate buffered saline wash was confirmed to have undetectable DNA level by using a real-time PCR quantification of the LEP gene[70]. Then, the IgG-bound DNA remaining in the resin of the column was eluted with 6 washes of freshly prepared buffer containing 1% sodium dodecyl sulphate and 0.1M sodium bicarbonate.

iii. DNA Extraction and Preparation of DNA Libraries.

DNA was extracted from 4 to 10 mL of plasma using the DSP Blood Mini Kit (Qiagen) with modifications of the manufacturer's protocol as previously reported[45]. For DNA sequencing, plasma DNA libraries were prepared using the Paired-End Sequencing Sample Preparation Kit (Illumina) as previously described[38]. For bisulfite sequencing, bisulfite-treated plasma DNA libraries were prepared using the Paired-End Sequencing Sample Preparation Kit (Illumina) and the EpiTect Plus DNA Bisulfite Kit (Qiagen)[40].

iv. DNA Sequencing and Alignment.

The bisulfite-treated or untreated DNA libraries were sequenced for 75 bp of each end in a paired-end format on Hi Seq2000 instruments (Illumina). DNA clusters were generated with a Paired-End Cluster Generation Kit v3 on a cBot instrument (Illumina). Real-time image analysis and base calling were performed using the HiSeq Control Software (HCS) v1.4 and Real Time Analysis (RTA) Software v1.13 (Illumina), by which the automated matrix and phasing calculations were based on the spiked-in PhiX control v3 sequenced with the libraries. After base calling, adapter sequences and low quality bases (i.e. quality score <5) on the fragment ends were removed.

For the analysis of sequencing data, the sequenced reads were aligned to the non-repeat-masked human reference genome (NCBI build 37/hg19) using the Short Oligonucleotide Alignment Program 2 (SOAP2)[71] as previously described[45]. Reads mappable to a unique genomic location were selected. Ambiguous or duplicated reads were removed. Sequenced reads with insert size ≤600 bp were retained for analysis.

v. Molecular Size Determination of Plasma DNA.

Paired-end sequencing, where sequencing was performed for both ends of each DNA molecule, was used to analyze each sample. By aligning the pair of end sequences of each DNA molecule to the reference human genome and noting the genome coordinates of the extreme ends of the sequenced reads, the sizes of the sequenced DNA molecules were determined. Plasma DNA molecules are naturally fragmented and hence the sequencing libraries for plasma DNA are typically prepared without any fragmentation steps[38]. Hence, the lengths deduced by the sequencing represented the sizes of the original plasma DNA molecules.

vi. Methylation Analysis of Plasma DNA.

For the analysis of bisulfite converted DNA sequencing data, an additional step for identification of methylated cytosines was performed. The trimmed reads were processed by a methylation data analysis pipeline called Methy-Pipe[72]. In order to align the bisulfite converted sequencing reads, we first performed in silico conversion of all cytosine residues to thymines, on the Watson and Crick strands separately, using the reference human genome (NCBI build 37/hg19). We then performed in silico conversion of each cytosine to thymine in all the processed reads and kept the positional information of each converted residue. After that, Methy-pipe was used to align the converted reads to the two pre-converted reference human genomes, with a maximum of two mismatches allowed for each aligned read. The cytosines originally present on the sequenced reads were recovered based on the positional information kept during the in silico conversion. The recovered cytosines among the CpG dinucleotides were scored as methylated. Thymines among the CpG dinucleotides were scored as unmethylated. We determined the methylation density of the whole human genome or any particular regions in the genome by determining the total number of unconverted cytosines at CpG sites as a proportion of all CpG sites covered by sequence reads mapped to the genome or the particular regions in the genome.

vii. Statistical Analysis.

Analysis was performed by using an in-house bioinformatics program, which was written in Perl and R languages, and SigmaStat version 3.5 software (Systat Software Inc.). A p value of less than 0.05 was considered as statistically significant and all probabilities were two-tailed.

TABLE 1

Percentage of bins with increased or decreased measured genomic representations (MGRs) in the plasma of SLE patients

| Group | Case no. | SLEDAI | Anti-dsDNA antibody level, IU/mL | Percentage of bins (%) with: increased MGR | decreased MGR | aberrant MGRs (increases + decreases) |
|---|---|---|---|---|---|---|
| Inactive | S073 | 0 | 0 | 1.1 | 0.7 | 1.8 |
| | S006 | 2 | 0 | 1.4 | 2.9 | 4.4 |
| | S017 | 2 | 107 | 4.3 | 3.0 | 7.4 |
| | S007 | 4 | 122 | 17.5 | 14.6 | 32.1 |
| | S019 | 4 | 139 | 6.2 | 5.4 | 11.6 |
| | S020 | 4 | 292 | 2.3 | 4.1 | 6.5 |
| | S002 | 4 | 312 | 2.5 | 3.9 | 6.4 |
| | S001 | 4 | 454 | 3.3 | 4.8 | 8.1 |
| | S012 | 4 | 500 | 0.3 | 0.2 | 0.5 |
| | S014 | 4 | 1000 | 11.8 | 9.9 | 21.8 |
| | S011 | 5 | 227 | 1.8 | 2.4 | 4.2 |
| | S013 | 5 | 613 | 5.3 | 4.5 | 9.9 |
| | S008 | 6 | 0 | 0.8 | 0.6 | 1.4 |
| | S009 | 6 | 0 | 1.5 | 1.5 | 3.1 |
| | S081 | 6 | 1000 | 6.0 | 8.0 | 14.0 |
| Active | S015 | 7 | 1000 | 9.3 | 8.9 | 18.2 |
| | S016 | 8 | 218 | 2.0 | 2.5 | 4.5 |
| | S003 | 8 | 228 | 1.3 | 1.8 | 3.1 |
| | S018 | 8 | 230 | 0.4 | 0.7 | 1.1 |
| | S010 | 8 | 832 | 4.1 | 4.0 | 8.1 |
| | S004 | 8 | 1000 | 3.6 | 2.9 | 6.5 |
| | S112 | 8 | 1000 | 17.6 | 15.3 | 32.9 |
| | S082 | 10 | 1000 | 13.9 | 12.1 | 26.0 |
| | S005 | 16 | 1000 | 26.5 | 25.5 | 52.0 |

TABLE 2

Percentage of bins with significant plasma DNA hypomethylation, normal methylation and hypermethylation in SLE patients

| Group | Case no. | SLEDAI | Anti-dsDNA antibody level, IU/mL | Percentage of bins (%) with: significant hypomethylation | normal methylation | significant hypermethylation |
|---|---|---|---|---|---|---|
| Inactive | S105 | 0 | 0 | 1.2 | 98.8 | 0.0 |
| | S125 | 0 | 0 | 0.0 | 99.9 | 0.1 |
| | S006 | 2 | 0 | 1.2 | 98.8 | 0.0 |
| | S017 | 2 | 107 | 1.0 | 99.0 | 0.0 |
| | S053 | 2 | 150 | 0.1 | 99.7 | 0.2 |
| | S019 | 4 | 139 | 1.4 | 98.6 | 0.0 |
| | S124 | 4 | 378 | 3.0 | 97.0 | 0.0 |
| | S026 | 4 | 1000 | 0.0 | 100.0 | 0.0 |
| | S059 | 4 | 1000 | 5.9 | 94.0 | 0.1 |
| | S013 | 5 | 613 | 18.6 | 81.4 | 0.0 |
| | S132 | 5 | 758 | 22.0 | 71.9 | 6.1 |
| Active | S015 | 7 | 1000 | 94.7 | 5.3 | 0.0 |
| | S203 | 8 | 793 | 48.7 | 51.3 | 0.0 |
| | S010 | 8 | 832 | 29.7 | 70.3 | 0.0 |
| | S031 | 8 | 896 | 79.9 | 20.1 | 0.0 |
| | S004 | 8 | 1000 | 58.4 | 41.6 | 0.0 |
| | S039 | 8 | 1000 | 42.7 | 57.3 | 0.0 |
| | S131 | 8 | 1000 | 23.3 | 76.3 | 0.3 |
| | S147 | 8 | 1000 | 49.2 | 50.8 | 0.0 |
| | S033 | 10 | 1000 | 21.5 | 78.5 | 0.0 |
| | S043 | 10 | 1000 | 1.0 | 98.9 | 0.1 |
| | S027 | 12 | 1000 | 64.5 | 35.5 | 0.0 |
| | S005 | 16 | 1000 | 94.0 | 6.0 | 0.0 |
| | S086 | 18 | 947 | 8.3 | 91.4 | 0.3 |

TABLE 3

Absolute DNA concentration of neat, IgG-bound and non-IgG-bound fractions

| Group | Case no. | SLEDAI | Anti- dsDNA antibody level, IU/mL | Neat Conc.† | IgG-bound Conc.† | IgG-bound Perc.* | Non-IgG-bound Conc.† | Non-IgG-bound Perc.* |
|---|---|---|---|---|---|---|---|---|
| Control | C020 | — | 0 | 1350 | 96 | 8 | 1112 | 92 |
| | C021 | — | 0 | 1714 | 139 | 8 | 1549 | 92 |
| | C073 | — | 0 | 932 | 30 | 4 | 713 | 96 |
| | C074 | — | 0 | 860 | 41 | 5 | 771 | 95 |
| Inactive | S073 | 0 | 0 | 1544 | 92 | 6 | 1344 | 94 |
| SLE | S125 | 0 | 0 | 2379 | 901 | 36 | 1600 | 64 |
| | S124 | 4 | 378 | 1349 | 983 | 70 | 419 | 30 |
| | S081 | 6 | 1000 | 1376 | 634 | 47 | 703 | 53 |
| Active | S203 | 8 | 793 | 515 | 316 | 65 | 168 | 35 |
| SLE | S112 | 8 | 1000 | 368 | 355 | 90 | 39 | 10 |
| | S147 | 8 | 1000 | 6560 | 794 | 14 | 5086 | 86 |
| | S082 | 10 | 1000 | 1042 | 277 | 38 | 459 | 62 |

†Concentration, copies/mL of plasma

*Percentage, %. The percentage calculation was based on the total amount of DNA in the IgG-bound and non-IgG-bound fractions.

TABLE 4

Methylation levels of plasma DNA in neat, IgG-bound and non-IgG-bound fractions

| Group | Case no. | SLEDAI | Anti- dsDNA antibody level, IU/mL | Neat MD† | Neat No. bins* | IgG-bound MD† | IgG-bound No. bins* | non-IgG-bound MD† | non-IgG-bound No. bins* |
|---|---|---|---|---|---|---|---|---|---|
| Control | C073 | — | 0 | 75.8 | 0 | 76.2 | 11 | 75.6 | 3 |
| | C074 | — | 0 | 77.1 | 0 | 78.0 | 0 | 77.2 | 0 |
| Inactive | S125 | 0 | 0 | 74.9 | 1 | 74.1 | 1 | 73.2 | 3 |
| SLE | S124 | 4 | 378 | 74.7 | 82 | 73.5 | 142 | 74.3 | 161 |
| Active | S203 | 8 | 793 | 70.5 | 1033 | 68.6 | 1646 | 71.0 | 766 |
| SLE | S147 | 8 | 1000 | 70.7 | 1345 | 70.1 | 1624 | 72.1 | 896 |

†Genomewide methylation density, %
*Number of bins with significant hypomethylation

IX. REFERENCES

1. Duarte C, Couto M, Ines L, Liang M H. Epidemiology of systemic lupus erythematosus. In: Lahita R G, Tsokos G, Buyon J, Koike T, eds. Systemic lupus erythematosus. 5th ed. London: Elsevier, 2011:673-96.
2. D'Cruz D P, Khamashta M A, Hughes G R. Systemic lupus erythematosus. Lancet 2007, 369:587-596.
3. Kotzin B L. Systemic lupus erythematosus. Cell. 1996; 85: 303-306. Review.
4. Wallace D J. The lupus book: A guide for patients and their families. Revised and expanded Edition. Oxford University Press, 2000.
5. Gladman D D, Urowitz M B. Prognosis, mortality and morbidity in systemic lupus erythematosus. In: Wallace D J, Hahn B H, eds. Dubois' lupus erythematosus. 7th ed. Philadelphia: Lippincott Williams & Wilkins, 2007:1333-53.
6. Pons-Estel G J, Alarcon G S, Scofield L, Reinlib L, Cooper G S. Understanding the epidemiology and progression of systemic lupus erythematosus. Semin Arthritis Rheum 2010; 39:257-268.
7. Isenberg D A, Shoenfeld Y, Walport M, Mackworth-Young C, Dudeney C, Todd-Pokropek A, Brill S, Weinberger A, Pinkas J. Detection of cross-reactive anti-DNA antibody idiotypes in the serum of systemic lupus erythematosus patients and of their relatives. Arthritis Rheum 1985; 28:999-1007.
8. Isenberg D A, Manson J J, Ehrenstein M R, Rahman A. Fifty years of anti-ds DNA antibodies: are we approaching journey's end? Rheumatology (Oxford) 2007; 46:1052-6.
9. Tsokos G C. Systemic lupus erythematosus. N Engl J Med 2011; 365:2110-21. Review.
10. Pisetsky D S, Ullal A J. The blood nucleome in the pathogenesis of SLE. Autoimmun Rev, 10:35-37.
11. Tax W J, Kramers C, van Bruggen M C, Berden J H. Apoptosis, nucleosomes, and nephritis in systemic lupus erythematosus. Kidney Int 1995, 48:666-673.
12. Pisetsky D S. The immune response to cell death in SLE. Autoimmun Rev 2004, 3:500-504.
13. Pisetsky D S, Jiang N. The generation of extracellular DNA in SLE: the role of death and sex. Scand J Immunol 2006, 64:200-204.
14. Su K Y, Pisetsky DS. The role of extracellular DNA in autoimmunity in SLE. Scand J Immunol 2009, 70:175-183.
15. Emlen W, Niebur J, Kadera R. Accelerated in vitro apoptosis of lymphocytes from patients with systemic lupus erythematosus. J Immunol 1994, 152:3685-3692.
16. Shoshan Y, Shapira I, Toubi E, Frolkis I, Yaron M, Mevorach D. Accelerated Fas-mediated apoptosis of monocytes and maturing macrophages from patients with systemic lupus erythematosus: relevance to in vitro impairment of interaction with iC3b-opsonized apoptotic cells. J Immunol 2001, 167:5963-5969.
17. Munoz L E, Gaipl U S, Franz S, Sheriff A, Voll R E, Kalden J R, Herrmann M. SLE—a disease of clearance deficiency? Rheumatology (Oxford) 2005, 44:1101-1107.
18. Sallai K, Nagy E, Derfalvy B, Muzes G, Gergely P. Antinucleosome antibodies and decreased deoxyribonuclease activity in sera of patients with systemic lupus erythematosus. Clin Diagn Lab Immunol 2005, 12:56-59.
19. Martinez Valle F, Balada E, Ordi-Ros J, Vilardell-Tarres M. DNase 1 and systemic lupus erythematosus. Autoimmun Rev 2008, 7:359-363.
20. Tan E M, Kunkel H G. Characteristics of a soluble nuclear antigen precipitating with sera of patients with systemic lupus erythematosus. J Immunol 1966, 96:464-471.
21. Raptis L, Menard H A. Quantitation and characterization of plasma DNA in normals and patients with systemic lupus erythematosus. J Clin Invest 1980, 66:1391-1399.
22. Chen J A, Meister S, Urbonaviciute V, Rodel F, Wilhelm S, Kalden J R, Manger K, Voll RE. Sensitive detection of plasma/serum DNA in patients with systemic lupus erythematosus. Autoimmunity 2007, 40:307-310.
23. Bartoloni E, Ludovini V, Alunno A, Pistola L, Bistoni O, Crino L, Gerli R. Increased levels of circulating DNA in patients with systemic autoimmune diseases: A possible marker of disease activity in Sjogren's syndrome. Lupus, 20:928-935.
24. Papalian M, Lafer E, Wong R, Stollar B D. Reaction of systemic lupus erythematosus antinative DNA antibodies with native DNA fragments from 20 to 1,200 base pairs. J Clin Invest 1980, 65:469-477.
25. Morimoto C, Sano H, Abe T, Homma M, Steinberg A D. Correlation between clinical activity of systemic lupus erythematosus and the amounts of DNA in DNA/anti-DNA antibody immune complexes. J Immunol 1982, 129:1960-1965.
26. Rumore P M, Steinman C R. Endogenous circulating DNA in systemic lupus erythematosus. Occurrence as multimeric complexes bound to histone. J Clin Invest 1990, 86:69-74.

27. Booth M J, Branco M R, Ficz G, Oxley D, Krueger F, Reik W, Balasubramanian S. Quantitative sequencing of 5-methylcytosine and 5-hydroxymethylcytosine at single-base resolution. Science 2012, 336:934-937.
28. Booth M J, Ost T W B, Beraldi D, Bell N M, Branco M R, Reik W, Balasubramanian S. Oxidative bisulfite sequencing of 5-methylcytosine and 5-hydroxymethylcytosine. Nature Protocols 2013, 8:1841-1851.
29. Yu M, Hon G C, Szulwach K E, Song C X, Jin P, Ren B, He C. Tet-assisted bisulfite sequencing of 5-hydroxymethylcytosine. Nature Protocols 2012, 7:2159-2170.
30. Flusberg B A, Webster D R, Lee J H, Travers K J, Olivares E C, Clark T A, Korlach J, Turner SW. Direct detection of DNA methylation during single-molecule, real-time sequencing. Nature Methods 2010, 7:461-465.
31. Shim J, Humphreys G I, Venkatesan B M, Munz J M, Zou X, Sathe C, Schulten K, Kosari F, Nardulli A M, Vasmatzis G, Bashir R. Detection and quantification of methylation in DNA using solid-state nanopores. Scientific Reports 2013, 3:1389.
32. Yee C S, Farewell V T, Isenberg D A, Griffiths B, Teh L-S, Bruce I N, Ahmad Y, Rahman A, Prabu A, Akil M, McHugh N, Edwards C, D'Cruz D, Khamashta M A, Gordon C. The use of Systemic Lupus Erythematosus Disease Activity Index-2000 to define active disease and minimal clinically meaningful change based on data from a large cohort of systemic lupus erythematosus patients. Rheumatology 2011, 50:982-988.
33. Huck S, Deveaud E, Namane A, Zouali M. Abnormal DNA methylation and deoxycytosine-deoxyguanine content in nucleosomes from lymphocytes undergoing apoptosis. FASEB J 1999, 13:1415-22.
34. Wen Z K, Xu W, Xu L, Cao Q H, Wang Y, Chu Y W, Xiong S D. DNA hypomethylation is crucial for apoptotic DNA to induce systemic lupus erythematosus-like autoimmune disease in SLE-non-susceptible mice. Rheumatology (Oxford) 2007, 46:1796-803.
35. Lui Y Y N, Chik K-W, Chiu R W, Ho C-Y, Lam C W K, Lo Y M D. Predominant hematopoietic origin of cell-free DNA in plasma and serum after sex-mismatched bone marrow transplantation. Clin Chem 2002, 48:421-427.
36. Tsui N B Y, Chim S S C, Chiu R W K, Lau T K, Ng E K O, Leung T N, Tong Y K, Chan K C A, Lo Y M D. Systematic micro-array based identification of placental mRNA in maternal plasma: towards non-invasive prenatal gene expression profiling. J Med Genet 2004, 41:461-467.
37. Lo Y M D, Chan K C A, Sun H, Chen E Z, Jiang P, Lun F M F, Zheng Y W, Leung T Y, Lau T K, Cantor C R, Chiu R W K. Maternal plasma DNA sequencing reveals the genome-wide genetic and mutational profile of the fetus. Sci Transl Med 2010, 2:61ra91.
38. Zheng Y W, Chan K C, Sun H, Jiang P, Su X, Chen E Z, Lun F M, Hung E C, Lee V, Wong J, Lai P B, Li C K, Chiu R W, Lo Y M D. Nonhematopoietically derived DNA is shorter than hematopoietically derived DNA in plasma: a transplantation model. Clin Chem 2011, 58:549-58.
39. Chan K C A, Zhang J, Hui A B, Wong N, Lau T K, Leung T N, Lo K W, Huang D W, Lo Y M D. Size distributions of maternal and fetal DNA in maternal plasma. Clin Chem 2004, 50:88-92.
40. Lun F M F, Chiu R W K, Sun K, Leung T Y, Jiang P, Chan K C A, Sun H, Lo Y M D. Noninvasive prenatal methylomic analysis by genomewide bisulfate sequencing of maternal plasma DNA. Clin Chem 2013, 59:1583-1594.
41. Chan K C A, Jiang P, Zheng Y W L, Liao G J W, Sun H, Wong J, Siu S S N, Chan W C, Chan S L, Chan A T C, Lai P B S, Chiu R W K, Lo Y M D. Cancer genome scanning in plasma: detection of tumor-associated copy number aberrations, single-nucleotide variants, and tumoral heterogeneity by massively parallel sequencing. Clin Chem 2013, 59:211-224.
42. Leary R J, Sausen M, Kinde I, Papadopoulos N, Carpten J D, Craig D, O'Shaughnessy J, Kinzler K W, Parmigiani G, Vogelstein B, Diaz Jr. L A, Velculescu V E. Detection of chromosomal alterations in the circulation of cancer patients with whole-genome sequencing. Sci Transl Med 2012, 4:162ra154.
43. Bombardier C, Gladman D D, Urowitz M B, Caron D, Chang C H. Derivation of the SLEDAI. A disease activity index for lupus patients. The Committee on Prognosis Studies in SLE. Arthritis Rheum 1992, 35:630-640.
44. Chiu R W K, Poon L L M, Lau T K, Leung T N, Wong E M, Lo Y M D. Effects of blood-processing protocols on fetal and total DNA quantification in maternal plasma. Clin Chem 2001, 47:1607-1613.
45. Chiu R W K, Akolekar R, Zheng Y W, Leung T Y, Sun H, Chan K C, Lun F M, Go A T, Lau E T, To W W, Leung W C, Tang R Y, Au-Yeung S K, Lam H, Kung Y Y, Zhang X, van Vugt J M, Minekawa R, Tang M R, Wang J, Oudejans C B, Lau T K, Nicolaides K H, Lo Y M D. Non-invasive prenatal assessment of trisomy 21 by multiplexed maternal plasma DNA sequencing: large scale validity study. BMJ 2011, 342:c7401.
46. Lister R, Pelizzola M, Dowen R H, Hawkins R D, Hon G, Tonti-Filippini J, Nery J R, Lee L, Ye Z, Ngo Q M, Edsall L, Antosiewicz-Bourget J, Stewart R, Ruotti V, Millar A H, Thomson J A, Ren B, Ecker J R. Human DNA methylomes at base resolution show widespread epigenomic differences. Nature 2009, 462:315-322.
47. Chiu R W K, Chan K C, Gao Y, Lau V Y, Zheng W, Leung T Y, Foo C H, Xie B, Tsui N B, Lun F M, Zee B C, Lau T K, Cantor C R, Lo Y M D. Noninvasive prenatal diagnosis of fetal chromosomal aneuploidy by massively parallel genomic sequencing of DNA in maternal plasma. Proc Natl Acad Sci USA 2008, 105:20458-20463.
48. Jiang P, Su Xiaoxi, Chen E Z, Sun K, Chiu R W, Lo Y M, Sun H. Methy-Pipe: an integrated bioinformatics data analysis pipeline for whole genome methylome analysis. In: IEEE International Conference on Bioinformatics and Biomedicine Workshops, 2010: pp 585-590.
49. Cervera R, et al. Morbidity and mortality in systemic lupus erythematosus during a 10-year period—A comparison of early and late manifestations in a cohort of 1,000 patients. Medicine 2003, 82:299-308.
50. Rullo O J, Tsao B P. Recent insights into the genetic basis of systemic lupus erythematosus. Ann Rheum Dis 2013, 72:56-61.
51. Strickland F M, Richardson B C. Epigenetics in human autoimmunity. Epigenetics in autoimmunity—DNA methylation in systemic lupus erythematosus and beyond. Autoimmunity 2008, 41:278-286.
52. Richardson B, et al. Evidence for impaired T-cell DNA methylation in systemic lupus erythematosus and rheumatoid arthritis. Arthritis Rheum 1990, 33:1665-1673.
53. Ballestar E, Esteller M, Richardson B C. The epigenetic face of systemic lupus erythematosus. J Immunol 2006, 176:7143-7147.
54. Yang M L, et al. Lupus autoimmunity altered by cellular methylation metabolism. Autoimmunity 2013, 46:21-31.

55. Palomaki G E, et al. DNA sequencing of maternal plasma to detect Down syndrome: An international clinical validation study. Genet Med 2011, 13:913-920.
56. Beck J, Umovitz H B, Mitchell W M, Schutz E. Next generation sequencing of serum circulating nucleic acids from patients with invasive ductal breast cancer reveals differences to healthy and nonmalignant controls. Mol Cancer Res 2010, 8:335-342.
57. Chan K C A, et al. Noninvasive detection of cancer-associated genome-wide hypomethylation and copy number aberrations by plasma DNA bisulfate sequencing. Proc Natl Acad Sci USA 2013, 110:18761-18768.
58. Krzywinski M, et al. Circos: An information aesthetic for comparative genomics. Genome Res 2009, 19:1639-1645.
59. Arbuckle M R, et al. Development of autoantibodies before the clinical onset of systemic lupus erythematosus. New Engl J Med 2003, 349:1526-1533.
60. Winfield J B, Faiferman I, Koffler D. Avidity of anti-DNA antibodies in serum and IgG glomerular eluates from patients with systemic lupus erythematosus. Association of high avidity anti-native DNA antibody with glomerulonephritis. J Clin Invest 1977, 59:90-96.
61. Termaat R M, et al. Anti-DNA antibodies can bind to the glomerulus via two distinct mechanisms. Kidney Int 1992, 42:1363-1371.
62. Uccellini M B, et al. Autoreactive B cells discriminate CpG-rich and CpG-poor DNA and this response is modulated by IFN-alpha. J Immunol 2008, 181:5875-5884.
63. Uccellini M B, Busto P, Debatis M, Marshak-Rothstein A, Viglianti G A. Selective binding of anti-DNA antibodies to native dsDNA fragments of differing sequence. Immunol Lett 2012, 143:85-9.
64. Yu S C Y, et al. Size-based molecular diagnostics using plasma DNA for noninvasive prenatal testing. Proc Natl Acad Sci USA 2014, 111:8583-8588.
65. Kelly T K, et al. Genome-wide mapping of nucleosome positioning and DNA methylation within individual DNA molecules. Genome Res 2012, 22:2497-2506.
66. Anker P, Stroun M, Maurice P A. Spontaneous extracellular synthesis of DNA released by human-blood lymphocytes. Cancer Res 1976, 36:2832-2839.
67. Rogers J C, Valeri C R, Skinner A, Boldt D, Kornfeld S. Excretion of deoxyribonucleic acid by lymphocytes stimulated with phytohemagglutinin or antigen. Proc Natl Acad Sci USA 1972, 69:1685-1689.
68. Lei W, et al. Abnormal DNA methylation in CD4+ T cells from patients with systemic lupus erythematosus, systemic sclerosis, and dermatomyositis. Scand J Rheumatol 2009, 38:369-374.
69. Zhang Y Q, Zhao M, Sawalha A H, Richardson B, Lu Q J. Impaired DNA methylation and its mechanisms in CD4(+)T cells of systemic lupus erythematosus. J Autoimmun 2013, 41:92-99.
70. Tsui N B Y, et al. High resolution size analysis of fetal DNA in the urine of pregnant women by paired-end massively parallel sequencing. PloS one 2012, 7:e48319.
71. Li R Q, et al. SOAP2: an improved ultrafast tool for short read alignment. Bioinformatics 2009, 25:1966-1967.
72. Jiang P, et al. Methy-Pipe: an integrated bioinformatics pipeline for whole genome bisulfate sequencing data analysis. PloS one 2014, 9:e100360.

X. COMPUTER SYSTEM

Figure 49:
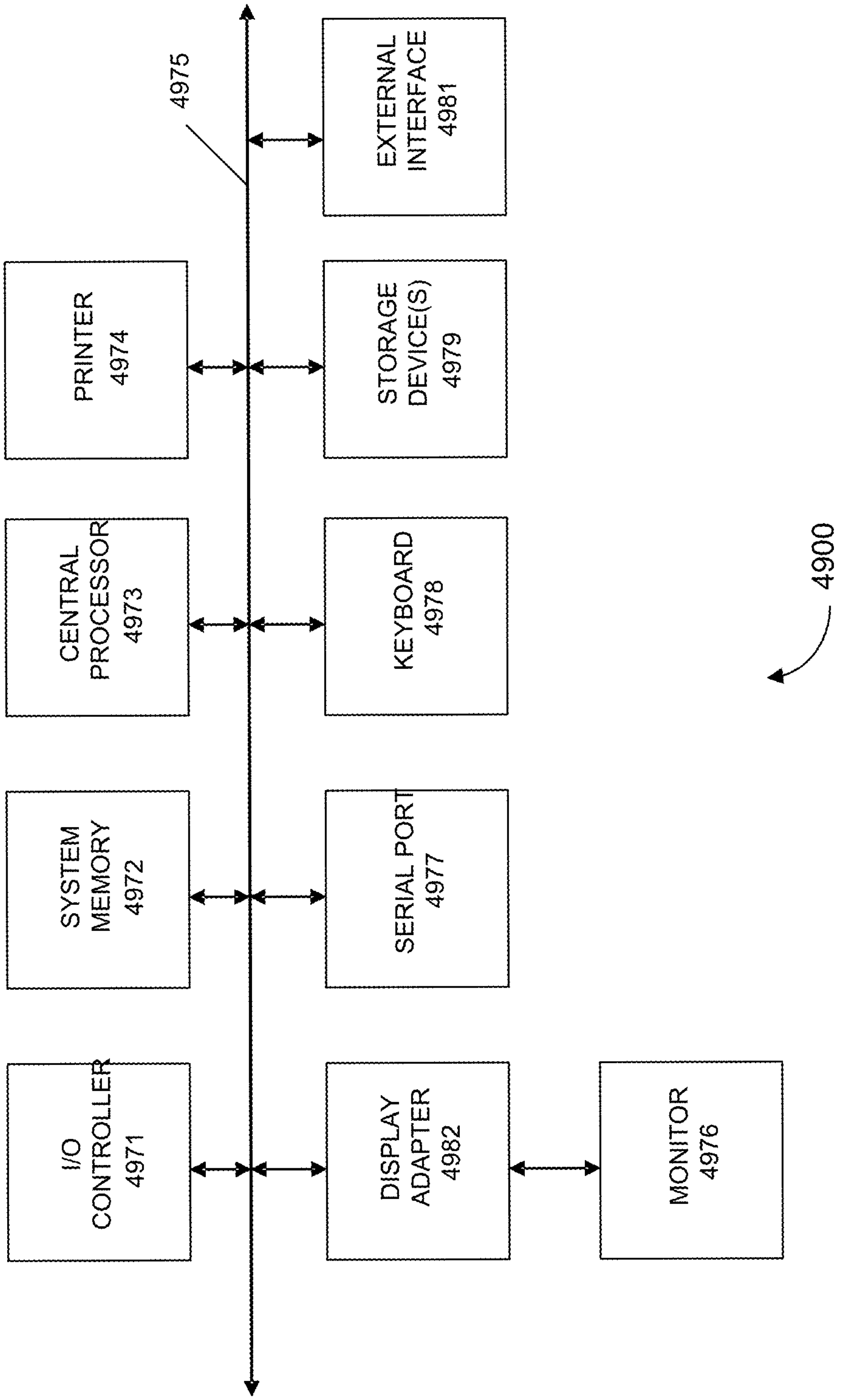
FIG. 49 shows a block diagram of an example computer system 4900 usable with systems and methods according to embodiments of the present invention.

Any of the computer systems mentioned herein may utilize any suitable number of subsystems. Examples of such subsystems are shown in FIG. 49 in computer apparatus 4900. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 49 are interconnected via a system bus 4975. Additional subsystems such as a printer 4974, keyboard 4978, storage device(s) 4979, monitor 4976, which is coupled to display adapter 4982, and others are shown. Peripherals and input/output (I/O) devices, which couple to I/O controller 4971, can be connected to the computer system by any number of means known in the art, such as serial port 4977. For example, serial port 4977 or external interface 4981 (e.g. Ethernet, Wi-Fi, etc.) can be used to connect computer system 4900 to a wide area network such as the Internet, a mouse input device, or a scanner. The interconnection via system bus 4975 allows the central processor 4973 to communicate with each subsystem and to control the execution of instructions from system memory 4972 or the storage device(s) 4979 (e.g., a fixed disk), as well as the exchange of information between subsystems. The system memory 4972 and/or the storage device(s) 4979 may embody a computer readable medium. Any of the values mentioned herein can be output from one component to another component and can be output to the user.

A computer system can include a plurality of the same components or subsystems, e.g., connected together by external interface 4981 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A computer product comprising a non-transitory computer readable medium storing a plurality of instructions that when executed control a computer system to perform a method of analyzing a biological sample of a subject as part of a screening for an auto-immune disease, the biological sample including nucleic acid molecules, wherein at least some of the nucleic acid molecules are cell-free, the method comprising:

analyzing sequence data of a plurality of cell-free DNA molecules from the biological sample of the subject as part of the screening for the auto-immune disease, wherein the auto-immune disease is SLE, wherein the plurality of cell-free DNA molecules comprises at least 15,000 cell-free DNA molecules, and wherein analyzing the sequence data of each cell-free DNA molecule of the plurality of cell-free DNA molecules comprises:

aligning the sequence data of the cell-free DNA molecule to a reference genome, determining a size of the cell-free DNA molecule from the aligned sequence data of the cell-free DNA molecule, and comparing the size of the cell-free DNA molecule with a threshold value;

determining an amount of the plurality of cell-free DNA molecules having sizes below the threshold value; and estimating a first level of the auto-immune disease in the subject based upon the amount, wherein the first level of the auto-immune disease is whether the subject has SLE, an extent of symptoms presented by the subject, or a progress of SLE.

2. The computer product of claim 1, wherein the method further comprises:

enriching the biological sample for cell-free DNA fragments having sizes less than or equal to 115 bp to form an enriched biological sample, wherein the plurality of cell-free DNA molecules is in the enriched biological sample.

3. The computer product of claim 1, wherein estimating the first level of the auto-immune disease in the subject comprises determining the auto-immune disease is present in the subject, the method further comprising:

using the first level of the auto-immune disease in the subject to design a treatment regimen for the subject or determine a dose of a medication.

4. The computer product of claim 1, wherein the auto-immune disease is a first auto-immune disease, and the method further comprises:

designating a first peak size of cell-free DNA molecules, wherein the first peak size is less than the threshold value;

designating a second peak size of cell-free DNA molecules, wherein the second peak size is greater than the threshold value;

determining a first peak number, wherein the first peak number is the number of the cell-free DNA molecules having sizes within a first specified range of the first peak size;

determining a second peak number, wherein the second peak number is the number of the cell-free DNA molecules having sizes within a second specified range of the second peak size;

calculating a ratio of the first peak number to the second peak number; and estimating a second level of a second auto-immune disease in the subject based upon the ratio.

5. The computer product of claim 4, wherein the first peak size is equal to the mean, median, or mode size of the cell-free DNA molecules having sizes less than the threshold value, and the second peak size is equal to the mean, median, or mode size of the cell-free DNA molecules having sizes greater than the threshold value.

6. The computer product of claim 2, wherein the enriched biological sample is an IgG-bound fraction.

7. The computer product of claim 1, wherein:

the sequence data includes a first sequence corresponding to one end of the cell-free DNA molecule and a second sequence corresponding to the other end of the cell-free DNA molecule, aligning the sequence data of the cell-free DNA molecule to the reference genome comprises mapping the first sequence and the second sequence to the reference genome to obtain genomic coordinates of the first sequence and the second sequence, and determining the size of the cell-free DNA molecule comprises subtracting the genomic coordinates of the first sequence from the second sequence.

8. The computer product of claim 1, wherein the method further comprises evaluating a treatment for the auto-immune disease in the subject by performing:

analyzing a pre-treatment biological sample according to claim 1, wherein the pre-treatment biological sample is obtained from the subject prior to treatment, and estimating a pre-treatment level of the auto-immune disease in the subject;

analyzing a post-treatment biological sample according to claim 1, wherein the post-treatment biological sample is obtained from the subject subsequent to treatment, and estimating a post-treatment level of the auto-immune disease in the subject; and comparing the pre-treatment level of the auto-immune disease with the post-treatment level of the auto-immune disease to determine a prognosis of the treatment.

9. The computer product of claim 8, wherein the treatment is determined to be effective if the post-treatment level of the auto-immune disease is lower than the pre-treatment level of the auto-immune disease.

10. The computer product of claim 8, the method further comprising:

determining a change between the pre-treatment level and the post-treatment level; and determining a degree of effectiveness based on the change.

11. The computer product of claim 10, wherein the change is determined by calculating a difference of or a ratio between the pre-treatment level and the post-treatment level.

12. A clinical testing system comprising:

a sequencing system;

a computer product comprising a non-transitory computer readable medium storing a plurality of instructions that when executed control a computer system to perform a method of analyzing a biological sample of a subject as part of a screening for an auto-immune disease, wherein the auto-immune disease is SLE, the biological sample including nucleic acid molecules, wherein at least some of the nucleic acid molecules are cell-free, the method comprising:

controlling the sequencing system to sequence a plurality of cell-free DNA molecules from the biological sample to produce sequence data, analyzing the sequence data, wherein the plurality of cell-free DNA molecules comprises at least 15,000 cell-free DNA molecules, wherein analyzing the sequence data of each cell-free DNA molecule of the plurality of cell-free DNA molecules comprises:

aligning the sequence data of the cell-free DNA molecule to a reference genome, determining a size of the cell-free DNA molecule from the aligned sequence data of the cell-free DNA molecule, and comparing the size of the cell-free DNA molecule with a threshold value;

determining an amount of the plurality of cell-free DNA molecules having sizes below the threshold value, and estimating a first level of the auto-immune disease in the subject based upon the amount, wherein the first level of the auto-immune disease is whether the subject has SLE, an extent of symptoms presented by the subject, or a progress of SLE; and one or more processors for executing the instructions stored on the non-transitory computer readable medium.

13. The clinical testing system of claim 12, wherein the method further comprises enriching the biological sample for cell-free DNA fragments having sizes less than or equal to 115 bp to form an enriched biological sample, wherein the plurality of cell-free DNA molecules is in the enriched biological sample.

14. The clinical testing system of claim 12, further comprising a device configured to obtain the biological sample from the subject.

15. The clinical testing system of claim 12, wherein estimating the first level of the auto-immune disease in the subject comprises determining the auto-immune disease is present in the subject, the method further comprising:

using the first level of the auto-immune disease in the subject to design a treatment regimen for the subject or determine a dose of a medication.

16. The clinical testing system of claim 12, wherein the auto-immune disease is a first auto-immune disease, and the method further comprises:

designating a first peak size of cell-free DNA molecules, wherein the first peak size is less than the threshold value;

designating a second peak size of cell-free DNA molecules, wherein the second peak size is greater than the threshold value;

determining a first peak number, wherein the first peak number is the number of the cell-free DNA molecules having sizes within a first specified range of the first peak size;

determining a second peak number, wherein the second peak number is the number of the cell-free DNA molecules having sizes within a second specified range of the second peak size;

calculating a ratio of the first peak number to the second peak number; and estimating a second level of a second auto-immune disease in the subject based upon the ratio.

17. The clinical testing system of claim 16, wherein the first peak size is equal to the mean, median, or mode size of the cell-free DNA molecules having sizes less than the threshold value, and the second peak size is equal to the mean, median, or mode size of the cell-free DNA molecules having sizes greater than the threshold value.

18. The clinical testing system of claim 12, wherein the biological sample is an IgG-bound fraction, the clinical testing system further comprising:

a device configured to separate the IgG-bound fraction from the non-IgG-bound fraction.

19. The clinical testing system of claim 12, wherein:

the sequence data includes a first sequence corresponding to one end of the cell-free DNA molecule and a second sequence corresponding to the other end of the cell-free DNA molecule, aligning the sequence data of the cell-free DNA molecule to the reference genome comprises mapping the first sequence and the second sequence to the reference genome to obtain genomic coordinates of the first sequence and the second sequence, and determining the size of the cell-free DNA molecule comprises subtracting the genomic coordinates of the first sequence from the second sequence.

20. The clinical testing system of claim 12, wherein the method further comprises evaluating a treatment for the auto-immune disease in the subject by performing:

analyzing a pre-treatment biological sample according to claim 12, wherein the pre-treatment biological sample is obtained from the subject prior to treatment, and estimating a pre-treatment level of the auto-immune disease in the subject;

analyzing a post-treatment biological sample according to claim 12, wherein the post-treatment biological sample is obtained from the subject subsequent to treatment, and estimating a post-treatment level of the auto-immune disease in the subject; and comparing the pre-treatment level of the auto-immune disease with the post-treatment level of the auto-immune disease to determine a prognosis of the treatment.

21. The clinical testing system of claim 20, wherein the treatment is determined to be effective if the post-treatment level of the auto-immune disease is lower than the pre-treatment level of the auto-immune disease.

22. The clinical testing system of claim 20, the method further comprising:

determining a change between the pre-treatment level and the post-treatment level; and determining a degree of effectiveness based on the change.

23. The clinical testing system of claim 22, wherein the change is determined by calculating a difference of or a ratio between the pre-treatment level and the post-treatment level.

* * * * *